US007238856B2

(12) United States Patent
Oswald et al.

(10) Patent No.: US 7,238,856 B2
(45) Date of Patent: Jul. 3, 2007

(54) NUCLEIC ACIDS ENCODING LIPID METABOLIZING PROTEINS FROM SUNFLOWER THAT CAUSE ELEVATION OF FATTY ACID LEVELS

(75) Inventors: Oliver Oswald, Ludwigshafen (DE); Jörg Bauer, Ludwigshafen (DE); Thorsten Zank, Mannheim (DE)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/021,619

(22) Filed: Dec. 23, 2004

(65) Prior Publication Data

US 2005/0155107 A1    Jul. 14, 2005

Related U.S. Application Data

(60) Provisional application No. 60/532,751, filed on Dec. 23, 2003.

(51) Int. Cl.
*C12N 15/82* (2006.01)
*C12N 5/14* (2006.01)
*A01H 5/00* (2006.01)
*C07H 21/04* (2006.01)

(52) U.S. Cl. ............... 800/281; 800/298; 536/23.2; 536/23.6; 435/419; 435/468; 435/320.1

(58) Field of Classification Search ............ None
See application file for complete search history.

(56) References Cited

U.S. PATENT DOCUMENTS

| 5,702,933 | A | * | 12/1997 | Klee et al. .............. 800/283 |
| 5,777,201 | A | | 7/1998 | Poutre et al. |
| 5,955,650 | A | | 9/1999 | Hitz |
| 6,084,164 | A | | 7/2000 | Bidney et al. |
| 7,135,618 | B2 | | 11/2006 | Mittendorf et al. |

FOREIGN PATENT DOCUMENTS

| EP | 1 033 405 A2 | 9/2000 |
| WO | WO 03/000898 A1 | 1/2003 |
| WO | WO 03/014376 A2 | 2/2003 |
| WO | WO 2005/063995 A2 | 7/2005 |
| WO | WO 2005/063995 A3 | 7/2005 |

OTHER PUBLICATIONS

Suesslin et al. An Arabidopsis mutant defective in UV-B light-mediated responses. (2003) The Plant Journal, vol. 33, pp. 591-601.*
Elomaa et al. Transformation of antisense constructs of the chalcone synthase gene superfamily into *Gerbera hybrida*: differential effect on the expression of family members. (1996) Molecular Breeding, vol. 2, pp. 41-50.*
Colliver et al. Differential modification of flavonoid and isoflavonoid biosynthesis with an antisense chalcone synthase construct in transgenic *Lotus corniculatus*. (1997) PMB, vol. 35, pp. 509-522.*
Voelker. Plant acyl-ACP thioesterases: chain-length determining enzymes in plant fatty acid biosynthesis. (1996) Genetic Engineering, ed. Jane K. Setlow, 18:111-133.*
Lazar et al. Transforming Growth Factor alpha: Mutation of Aspartic Acid 47 and Leucine 48 Results in Different Biological Activities. (1988) Molecular and Cellular Biology, vol. 8, pp. 1247-1252.*
Hill et al. Functional analysis of conserved histidines in ADP-glucose pyrophosphorylase from *Escherichia coli*. (1998) Biochemical and Biophysical Research Communications, vol. 244, pp. 573-577.*
Guo et al. Protein tolerance to random amino acid change. (2004) PNAS, vol. 101, pp. 9205-9210.*
Kozik et al. Lettuce and Sunflower ESTs from the Composite Genome Project. (2002) GenBank Accession BQ968164., pp. 1-2.*
The Arabidopsis Genome Initiative 2000 Analysis of the genome sequence of the flowering plant *Arabidopsis thaliana*. Nature 408:796-844.
Arenas-Huertero et al., 2000, "Analysis of *Arabidopsis* glucose insensitive mutants, gin5 and gin6, reveals a central role of the plant hormone ABA in the regulation of plant vegetative development by sugar", Genes Dev. 14:2085-2096.
Beisson et al., 1997, "An esterase neosynthesized post-germinated sunflower seeds is related to a new family of lipolytic enzymes," Plant Physiol. Biochem 35(10):761-65.
Beaudoin et al., 2000, "Interactions between Abscisic Acid and Ethylene Signaling Cascades", Plant Cell 2000:1103-15. Brenner, 1997, "Regulatory function of Δ6 desaturase—key enzyme of polyunsaturated fatty acid synthesis", Adv. Exp. Med. Biol., 83: 85-101.
Browse et al., 1986, "Fluxes through the prokaryotic and eukaryotic pathways of lipid synthesis in the '16:3' plant *Arabidopsis thaliana*", Biochemical Journal, 235:25-31.
Buhr et al., 2002, "Ribozyme termination of RNA transcripts down-regulate seed fatty acid genes in transgenic soybean", The Plant Journal 30(2):155-63.
Cahoon et al., 1992, "Expression of a coriander desaturase results in petroselinic acid production in transgenic tobacco", Proc. Natl. Acad. Sci. USA 89:11184-88.
Cohen, 1992, "Signal integration at the level of protein kinases, protein phosphatases and their substrates", Trends Biochem. Sci. 17:408-413.
Colon-Carmona, et al., 2000, "Aux/IAA Proteins Are Phosphorylated by Phytochrome in Vitro" Plant Physiol. 124:1728-38.

(Continued)

*Primary Examiner*—Anne Kubelik
*Assistant Examiner*—Cathy Kingdon Worley
(74) *Attorney, Agent, or Firm*—Connolly Bove Lodge & Hutz LLP

(57) ABSTRACT

Isolated nucleic acids and proteins associated with lipid and sugar metabolism regulation are provided. In particular, the present invention provides lipid metabolism proteins (LMP) and encoding nucleic acids originating from *Helianthus annuus*. The sunflower LMP nucleic acids and proteins are used in methods of producing transgenic plants and modulating levels of total fatty acids in seeds of the transgenic plants transformed with an expression cassette designed to express the sunflower LMP.

20 Claims, 1 Drawing Sheet

OTHER PUBLICATIONS

Eccleston and Ohlrogge, 1998, "Expression of Lauroyl-Acyl Carrier Protein Thioesterase in *Brassica napus* Seeds Induces Pathways for Both Fatty Acid Oxidation and Biosynthesis and Implies a Set Point for Triacylglycerol Accumulation", The Plant Cell, 10:613-21.

Focks & Benning, 1998, "wrinkled1: A Novel, Low-Seed-Oil Mutant of Arabidopsis with a Deficiency in the Seed-Specific Regulation of Carbohydrate Metabolism", Plant Physiol., 118:91-101.

Frentzen, 1998, "Acyltransferases from basic science to modified seed oils", Lipid, 100:161-66.

Härtel et al., 2000, "DGD1—independent biosynthesis of extraplastidic galactolipids after phosphate deprivation in *Arabidopsis*" Proc. Natl. Acad. Sci. USA, 97 (19):10649-10654.

Hatje et al., 1989, "World Importance of Oil Crops and Their Products", Oil Crops of the World-Their Breeding and Utilization, eds. Röbbelen, Downey, and Ashri, pp. 1-21.

Herzog et al., "*Arabidopsis thaliana* clone PAP322 GAST1 protein homolog mRNA, complete cds." GenBank Accession No. U11764, Aug. 21, 1996.

Höfgen and Willmitzer, 1990, "Biochemical and Genetic Analysis of Different Patatin Isoforms Expressed in Various Organs of Potato (Solanum Tuberosum)", Plant Sci. 66:221-230.

Holvoet et al., 2000, "The Arg123-Tyr166 Central Domain of Human ApoAI Is Critical for Lecithin:Cholesterol Acyltransferase-Induced Hyperalphalipoproteinemia and HDL Remodeling in Transgenic Mice," Arteriosclerosis Thrombosis Vascular Biology, 459-466.

Hurry et al., 2000, "The role of inorganic phosphate in the development of freezing tolerance and the acclimatization of photosynthesis to low temperature is revealed by the *pho* mutants of *Arabidopsis thaliana*", The Plant Journal, 27(3)383-396.

Kang & Rawsthorne, "Starch and fatty acid synthesis in plastids from developing embryos of oilseed rape (*Brassica napus* L.)", 1994, Plant J., vol. 6, 795-805.

Kim et al., "*Arabidopsis thaliana* Atlg54020/F15I1_10 mRNA complete cds", EMBL Accession No. AY132004, Aug. 12, 2002.

Kinney et al., 1994, "Genetic Modification of the Storage Lipids of Plants," Current Opin. in Biotech. 5:144-151.

Kuo et al. 1996, "Okadaic Acid, a Protein Phosphatase Inhibitor; Blocks Calcium Changes, Gene Expression, and Cell Death Induced by Gibberellin in Wheat Aleurone Cells", Plant Cell. 8:259-269.

Mahmoud and Croteau, 2001, "Metabolic Engineering of Essential Oil Yield and Composition in Mint by Altering Expression of Deoxyxylulose Phosphate Reductoismerase and Menthofuran Synthase," Proc. Natl. Acad. Sci. USA 98(15):8915-20.

Merlot et al., "The ABI1 and ABI2 protein phosphatases 2C act in a negative feedback regulatory loop of the abscisic acid signaling pathway", The Plant Journal, 15(3):295-303.

Metz et al., 2000, "Purification of a Jojoba Embryo Fatty Acyl-Coenzyme A Reductase and Expression of Its cDNA in High Erucic Acid Rapeseed," Plant Physiology 122:635-644.

Meyer et al., 1994, "A protein phosphatase 2C involved in ABA signal transduction in *Arabidopsis thaliana*", Science 264:1452-55.

Millar et al., 2000, "All fatty acids are not equal: discrimination in plant membrane lipids", Trends Plant Sci. 5:95-101.

Mitsukawa et al., 1997. "Overexpression of an *Arabidopsis thaliana* high-affinity phosphate transporter gene in tobacco cultured cells enhances cell growth under phophate-limited conditions", Proc. Natl. Acad. Sci. USA, 94 (13):7098-7102.

Mueller et al., 2000, "Lipid Phosphorylation in Chloroplast Envelopes", The Journal of Biological Chemistry, 275 (26):19475-19481.

Ogas et al., 1997, "Cellular Differentiation Regulated by Gibberellin in the *Arabidopsis thaliana* pickle Mutant", Science 277:91-94.

Ogas, et al. 1999, "PICKLE is a CHD3 chromatin-remodeling factor that regulates the transition from embryonic to vegetative development in *Arabidopsis*", Proc. Natl. Acad. Sci. USA 96:13839-13844.

Ohlrogge & Browse, 1995, "Lipid Biosynthesis", Plant Cell, 7:957-70.

Ohlrogge et al., 2000, "Fatty acid synthesis: from $CO_2$ to functional genomics", Biochem. Sci., Trans. 28(6):567-73.

Parveez, et al., 1000, "Transgenic Oil Palm: Production and Projection," Biochem. Soc. Trans. 28(6):969.

Plaxton, 1996, "The organization and regulation of plant glycolysis", Annu. Rev. Plant Physiol. Plant Mol. Biol., 47:185-214.

Ritchie & Gilroy, 1998, "Calcium-Dependent Protein Phosphorylation May Mediate the Gibberellic Acid Response in Barley Aleurone", Plant Physiol., 116:765-76.

Savage & Ohlrogge, 1999, "Phosphorylation of pea chloroplast acetyl-CoA carboxylase", The Plant Journal, 18(5):521-527.

Shanklin & Cahoon, 1998, "Desaturation and related modifications of fatty acids", Annu. Rev. Plant Physiol. Plant Mol. Biol., 49:611-641.

Southwick et al., "*Arabidopsis thaliana* lipase/acylhydroise: myrosinase-associated protein (MAG2.21) mRNA, complete cds." EMBL Accession No. AY062690, Nov. 27, 2001.

Taipalensuu et al., 1997, "Regulation of the wound-induced myrosinase-associated protein transcript in *Brassica napus* plants", Eur. J. Biochem,. 247,963-971.

Taipalensuu et al., 1996, "A Wound- and Methyl Jasmonate-Inducible Transcript Coding for a Myrosinase-Associated Protein with Similarities to an Early Nodulin", Plant Physiol. 110:483-491.

Taipalensuu et al., "*B.napus* for myrosinase-associated protein, clone library iMyAP12". EMBL Accession No. Y10156, Jan. 8, 1997.

Taipalensuu et al., "*B.napus* for myrosinase-associated protein, clone library iMyAP9". EMBL Accession No. Y10155, Jan. 8, 1997.

Taipalensee et al., "*Brassica napus* myrosinase-associated protein mRNA, partial cds". EMBL Accession No. U39319, Mar. 8, 1996.

Theologis, "Sequence of BAC F15I1 from *Arabidopsis thaliana* chromosome 1, complete sequence". EMBL Accession No. AC006577, Mar. 25, 1999.

Töpfer et al., 1995, "Modification of Plant Lipid Synthesis", Science 268:681-686.

Van De Loo et al., "An oleate 12-hydroxylase from *Ricinus communis* L. is a fatty acyl desaturase homolog", 1995, Proc. Natl. Acad. Sci. USA, 92:6743-47.

Van De Loo et al., 1993, "Unusual Fatty Acids in Lipid Metabolism in Plants", pp. 91-126, editor TS Moore Jr. CRC Press.

Voelker, 1996, "Plant acyl-ACP thioesterases: chain-length determining enzymes in plant fatty acid biosynthesis" in Genetic Engineering, ed. Jane K. Setlow, 18:111-33.

White et al., 2000, "A New Set of *Arabidopsis* Expressed Sequence Tags from Developing Seeds. The Metabolic Pathway from Carbohydrates to Seed Oil," Plant Physiol., 124:1582-1594.

Yamada et al., "*Arabidopsis thaliana* clone C00205 (e) putative myrosinase-associated protein (Atlg54020) mRNA, complete cds." EMBL Accession No. AF348585, Mar. 9, 2001.

Zhou, et al. 1998, "Glucose and ethylene signal transduction crosstalk revealed by an *Arabidopsis* glucose-insensitive mutant", Proc. Natl. Acad. Sci. USA 95:10297-10299.

Zou et al., 1997, "Modification of Seed Oil Content and Acyl Composition Brassicaceae By Expression of a Yeast sn-2 Acyltransferase Gene," Plant Cell 9:909-23.

\* cited by examiner

NUCLEIC ACIDS ENCODING LIPID METABOLIZING PROTEINS FROM SUNFLOWER THAT CAUSE ELEVATION OF FATTY ACID LEVELS

CROSS REFERENCE TO RELATED APPLICATIONS

This application claims the priority benefit of U.S. Provisional Application Ser. No. 60/532,751 filed Dec. 23, 2003, the entire contents of which are hereby incorporated by reference.

BACKGROUND OF THE INVENTION

1. Field of the Invention

This invention relates generally to nucleic acid sequences encoding proteins that are related to the presence of seed storage compounds in plants. More specifically, the present invention relates to nucleic acid sequences encoding sugar, protein, and lipid metabolism enzymes and regulator proteins and the use of these sequences in transgenic plants. The invention further relates to methods of applying these novel plant polypeptides to the identification and stimulation of plant growth and/or to the increase of yield of seed storage compounds.

2. Background Art

The study and genetic manipulation of plants has a long history that began even before the famed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al., 1995, Science 268: 681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164), rapeseed (Töpfer et al., 1995, Science 268: 681-686), and non-traditional oil seed plants such as tobacco (Cahoon et al., 1992, Proc. Natl. Acad. Sci. USA 89: 11184-11188).

Plant seed oils comprise both neutral and polar lipids (See Table 1). The neutral lipids contain primarily triacylglycerol, which is the main storage lipid that accumulates in oil bodies in seeds. The polar lipids are mainly found in the various membranes of the seed cells, e.g. the microsomal, plastidial, and mitochondrial membranes, and the cell membrane. The neutral and polar lipids contain several common fatty acids (See Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al., 1993, Unusual Fatty Acids in Lipid Metabolism in Plants pp. 91-126, editor T S Moore Jr. CRC Press; Millar et al., 2000, Trends Plant Sci. 5:95-101).

TABLE 1

| Plant Lipid Classes | |
| --- | --- |
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

| Common Plant Fatty Acids | |
| --- | --- |
| 16:0 | Palmitic acid |
| 16:1 | Palmitoleic acid |
| 16:3 | Hiragonic acid |
| 18:0 | Stearic acid |
| 18:1 | Oleic acid |
| 18:2 | Linoleic acid |
| 18:3 | Linolenic acid |
| γ-18:3 | Gamma-linolenic acid* |
| 20:0 | Arachidic acid |
| 20:1 | Eicosenoic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

In Table 2, the fatty acids denoted with an asterisk do not normally occur in plant seed oils, but their production in transgenic plant seed oil is of importance in plant biotechnology.

The primary sites of fatty acid biosynthesis in plants are the plastids. Fatty acid biosynthesis begins with the conversion of acetyl-CoA to malonyl-CoA by acetyl-CoA carboxylase (ACCase). The malonyl moiety is then transferred to an acyl carrier protein (ACP) by the malonyl-CoA:ACP transacylase. The enzyme beta-keto-acyl-ACP-synthase III (KAS III) catalyzes the initial condensation reaction of fatty acid biosynthesis, in which after decarboxylation of malonyl-ACP, the resulting carbanion is transferred to acetyl-CoA by a nucleophilic attack of the carbonyl-carbon, resulting in the formation of 3-ketobutyryl-ACP. The reaction cycle is completed by a reduction, a dehydration and again a reduction yielding butyric acid. This reaction cycle is repeated (with KAS I or KAS II catalyzing the condensation reaction) until the acyl-group reach a chain length of usually 16 to 18 carbon atoms. These acyl-ACPs can be desaturated by the stearoyl-ACP desaturase, used as substrates for plastidial acyltransferases in the formation of lipids through what has been referred to as the prokaryotic pathway, or exported to the cytosol after cleavage from ACP through the action of thioesterases. In the cytosol they enter the acyl-CoA pool and can be used for the synthesis of lipids through what has been referred to as the eukaryotic pathway in the endoplasmic reticulum.

Lipid synthesis through both the prokaryotic and eukaryotic pathways occurs through the successive acylation of glycerol-3-phosphate, catalyzed by glycerol-3-phosphate acyltransferases (GPAT) and lysophosphatidic acid acyltransfersas (LPAAT) (Browse et al., 1986, Biochemical J. 235:25-31; Ohlrogge & Browse, 1995, Plant Cell 7:957-

970). The resulting phosphatidic acid (PA) is the precursor for other polar membrane lipids such as monogalactosyldiacylglycerol (MGD), digalactosyldiacylglycerol (DGD), phosphatidylglycerol (PG) and sulfoquinovosyldiacylglycerol (SQD) in the plastid and phosphatidylcholine (PC), phosphatidylethanolamine (PE), phosphatidylinositol (PI) and phosphatidylserine (PS) in the endoplasmic reticulum. The polar lipids are also the sites of further modification of the acyl-chain such as desaturation, acetylenation, and hydroxylation. In the endoplasmic reticulum, PA is also the intermediate in the biosynthesis of triacylglycerol (TAG), the major component of neutral lipids and hence of seed oil. Furthermore, alternative pathways for the biosynthesis of TAGs can exists (i.e. transacylation through the action of phosphatidylcholine:diacylglycerol acyltransferase) (Voelker, 1996, Genetic Engineering ed.:Setlow 18:111-113; Shanklin & Cahoon, 1998, Annu. Rev. Plant Physiol. Plant Mol. Biol. 49:611-641; Frentzen, 1998, Lipids 100:161-166; Millar et al., 2000, Trends Plant Sci. 5:95-101). The reverse reaction, the breakdown of triacylglycerol to diacylglycerol and fatty acids is catalyzed by lipases. Such a breakdown can be seen toward the end of seed development resulting in a certain reduction in seed oil. (Buchanan et al., 2000).

Storage lipids in seeds are synthesized from carbohydrate-derived precursors. Plants have a complete glycolytic pathway in the cytosol (Plaxton, 1996, Annu. Rev. Plant Physiol. Plant Mol. Biol. 47:185-214), and it has been shown that a complete pathway also exists in the plastids of rapeseeds (Kang & Rawsthorne, 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions, and the exact contribution of each reaction is still being debated (Ohlrogge & Browse, 1995, Plant Cell 7:957-970). It is accepted, however, that a large part of the acetyl-CoA is derived from glucose-6-phospate and pyruvate that are imported from the cytoplasm into the plastids. Sucrose is produced in the source organs (leaves, or anywhere that photosynthesis occurs) and is transported to the developing seeds that are also termed sink organs. In the developing seeds, the sucrose is the precursor for all the storage compounds, i.e. starch, lipids, and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (See, e.g., Töpfer et al., 1995, Science 268:681-686). For example, introduction of a $\Delta^{12}$-hydroxylase nucleic acid sequence into transgenic tobacco resulted in the formation of a novel fatty acid, ricinoleic acid, into the tobacco seed oil (Van de Loo et al., 1995, Proc. Natl. Acad. Sci USA 92: 6743-6747). Tobacco plants have also been engineered to produce low levels of petroselinic acid by the introduction and expression of an acyl-ACP desaturase from coriander (Cahoon et al., 1992, Proc. Natl. Acad. Sci USA 89:11184-11188).

The modification of seed oil content in plants has significant medical, nutritional, and economic ramifications. With regard to the medical ramifications, the long chain fatty acids (C18 and longer) found in many seed oils have been linked to reductions in hypercholesterolemia and other clinical disorders related to coronary heart disease (Brenner, 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as *Brassica*, soybean, carrot, pine, and *Arabidopsis thaliana* have also been cloned and determined to encode proteins associated with the phospholipid monolayer membrane of oil bodies in those plants.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses nucleic acid sequences from *Arabidopsis thaliana, Brassica napus*, and *Helianthus annuus*. These nucleic acid sequences can be used to alter or increase the levels of seed storage compounds such as proteins, sugars, and oils, in plants, including transgenic plants, such as rapeseed, canola, linseed, soybean, sunflower maize, oat, rye, barley, wheat, pepper, tagetes, cotton, oil palm, coconut palm, flax, castor and peanut, which are oilseed plants containing high amounts of lipid compounds.

SUMMARY OF THE INVENTION

The present invention provides novel isolated nucleic acid and amino acid sequences associated with the metabolism of seed storage compounds in plants.

The present invention also provides isolated nucleic acids from *Arabidopsis thaliana, Brassica napus*, and *Helianthus annuus* encoding Lipid Metabolism Proteins (LMPs), or portions thereof. These sequences may be used to modify or increase lipids and fatty acids, cofactors, sugars, and enzymes in microorganisms and plants.

*Arabidopsis* plants are known to produce considerable amounts of fatty acids such as linoleic and linolenic acid (See, e.g., Table 2) and for their close similarity in many aspects (gene homology, etc.) to the oil crop plant *Brassica*. Therefore, nucleic acid molecules originating from a plant like *Arabidopsis thaliana* are especially suited to modify the lipid and fatty acid metabolism in a host, especially in microorganisms and plants. Furthermore, nucleic acids from the plants *Arabidopsis thaliana* can be used to identify those DNA sequences and enzymes in other species which are useful to modify the biosynthesis of precursor molecules of fatty acids in the respective organisms.

The present invention also provides isolated nucleic acids comprising a fragment of at least 60 nucleotides of an *Arabidopsis thaliana, Brassica napus*, or *Helianthus annuus*

LMP nucleic acid disclosed herein. The present invention further provides isolated nucleic acids having at least 70% sequence identity with a full-length *Arabidopsis thaliana*, *Brassica napus*, or *Helianthus annuus* LMP nucleic acid disclosed herein. The present invention also provides isolated nucleic aicds having at least 90% sequence identity with a full-length *Arabidopsis thaliana, Brassica napus*, or *Helianthus annuus* LMP nucleic acid disclosed herein. The present invention further provides isolated nucleic acids that hybridize under stringent conditions to an *Arabidopsis thaliana, Brassica napus*, or *Helianthus annuus* LMP nucleic acid disclosed herein.

Also provided by the present invention are polypeptides encoded by the nucleic acids, heterologous polypeptides comprising polypeptides encoded by the nucleic acids, and antibodies to those polypeptides. The present invention further provides isolated polypeptides having at least 70% sequence identity with a full-length *Arabidopsis thaliana*, *Brassica napus*, or *Helianthus annuus* LMP polypeptide disclosed herein. The present invention also provides isolated polypeptides having at least 90% sequence identity with a full-length *Arabidopsis thaliana, Brassica napus*, or *Helianthus annuus* LMP polypeptide disclosed herein. Accordingly, the present invention provides novel isolated LMP nucleic acids and isolated LMP polypeptides from *Arabidopsis thaliana, Brassica napus*, or *Helianthus annuus*, as well as active fragments, analogs, and orthologs thereof.

Additionally, the present invention relates to and provides the use of LMP nucleic acids in the production of transgenic plants having a modified level of a seed storage compound. A method of producing a transgenic plant with a modified level of a seed storage compound includes the steps of transforming a plant cell with an expression vector comprising an LMP nucleic acid, and generating a plant with a modified level of the seed storage compound from the plant cell. In a preferred embodiment, the plant is an oil producing species or oilseed species selected from the group consisting of rapeseed, canola, linseed, soybean, sunflower, maize, oat, rye, barley, wheat, pepper, tagetes, cotton, oil palm, coconut palm, flax, castor, and peanut, for example.

According to the present invention, the compositions and methods described herein can be used to increase or decrease the level of an LMP in a transgenic plant comprising increasing or decreasing the expression of the LMP nucleic acid in the plant. Increased or decreased expression of the LMP nucleic acid can be achieved through in vivo mutagenesis of the LMP nucleic acid. The present invention can also be used to increase or decrease the level of a lipid in a seed oil, to increase or decrease the level of a fatty acid in a seed oil, or to increase or decrease the level of a starch in a seed or plant.

Also included herein is a seed produced by a transgenic plant transformed by an LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, or to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing an LMP nucleic acid from *Arabidopsis thaliana, Brassica napus*, or *Helianthus annuus* in the transgenic plant, wherein the transgenic plant is *Arabidopsis thaliana, Brassica napus*, or *Helianthus annuus*, or a species different from *Arabidopsis thaliana, Brassica napus*, or *Helianthus annuus*. Also included herein are compositions and methods of the modification of the efficiency of production of a seed storage compound.

The present invention also provides transgenic plants having modified levels of seed storage compounds, and in particular, modified levels of a protein, a lipid, a fatty acid, or a sugar.

The polynucleotides and polypeptides of the present invention, including agonists and/or fragments thereof, also have uses that include modulating plant growth, and potentially plant yield, preferably increasing plant growth under adverse conditions (drought, cold, light, UV). In addition, antagonists of the present invention may have uses that include modulating plant growth and/or yield, preferably through increasing plant growth and yield. In yet another embodiment, overexpression of the polypeptides of the present invention using a constitutive promoter (e.g., 35S or other promoters) may be useful for increasing plant yield under stress conditions (drought, light, cold, UV) by modulating light utilization efficiency.

The present invention also provides methods for producing such aforementioned transgenic plants. The present invention further provides seeds and seed oils from such aforementioned transgenic plants.

These and other embodiments, features, and advantages of the present invention will become apparent after a review of the following detailed description.

DETAILED DESCRIPTION OF THE INVENTION

Figure 1:
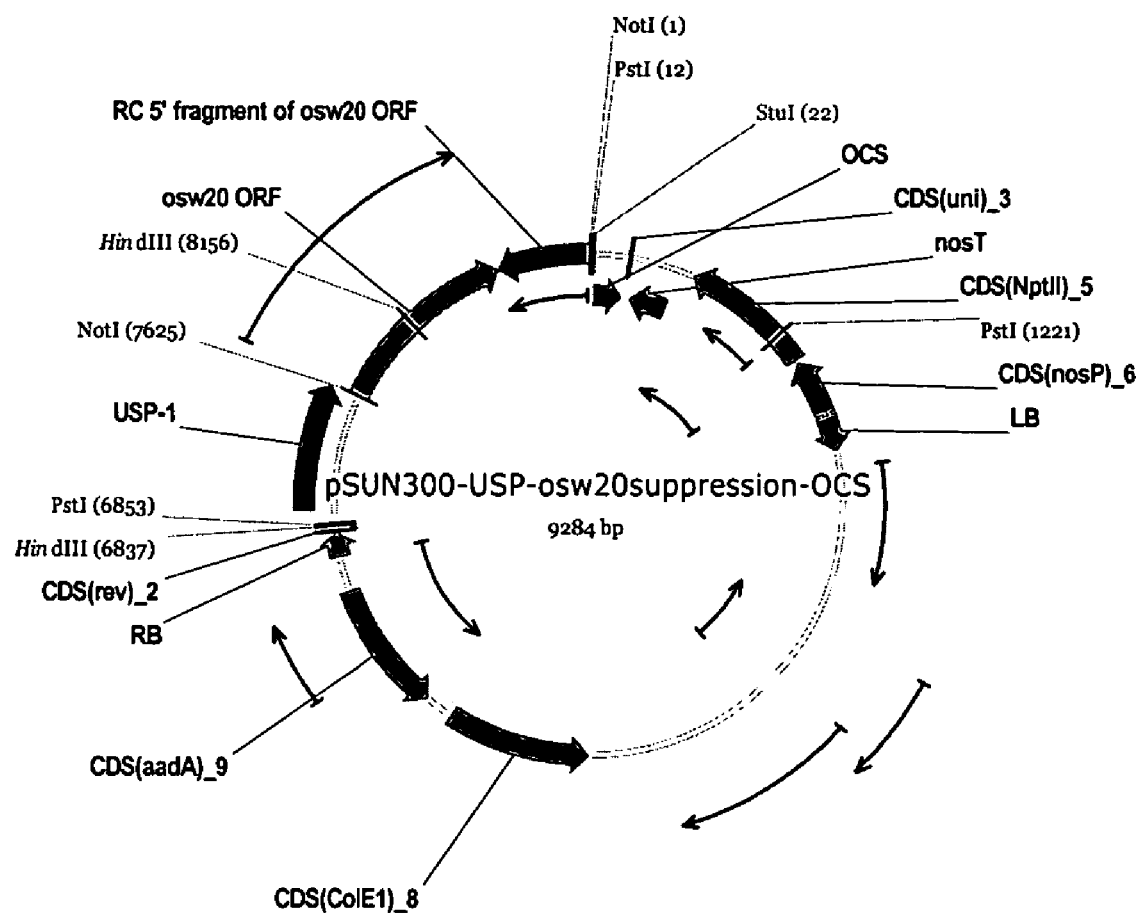
FIG. 1 is a schematic representation of the binary vector carrying the osw20 suppression construct.

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

In accordance with the purpose(s) of this invention, as embodied and broadly described herein, this invention, in one aspect, provides an" isolated nucleic acid from a plant (*Arabidopsis thaliana, Brassica napus*, and *Helianthus annuus*) encoding a Lipid Metabolism Protein (LMP), or a portion thereof. As used herein, the phrase "*Arabidopsis thaliana, Brassica napus*, and *Helianthus annuus*" is intended to mean *Arabidopsis thaliana* and/or *Brassica napus* and/or *Helianthus annuus*.

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the terms "nucleic acid molecule" and "polynucleotide sequence" are used interchangeably and are intended to include DNA molecules (e.g., cDNA or genomic DNA) and RNA molecules (e.g., mRNA), and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences, which naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., an *Arabidopsis thaliana, Brassica napus*, or *Helianthus annuus* cell). Moreover, an "isolated" nucleic acid molecule, such as a cDNA molecule, can be substantially free of other cellular material, or culture medium when produced by recombinant techniques, or chemical precursors, or other chemicals when chemically synthesized.

A nucleic acid molecule of the present invention, e.g., a nucleic acid molecule having a polynucleotide sequence as shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123, or a portion thereof, can be isolated using standard molecular biology techniques and the sequence information provided herein. For example, an *Arabidopsis thaliana, Brassica napus*, or *Helianthus annuus* LMP cDNA can be isolated from an *Arabidopsis thaliana, Brassica napus*, or *Helianthus annuus* library using all or portion of one of the disclosed polynucleotide sequences as a hybridization probe and standard hybridization techniques (e.g., as described in Sambrook et al., 1989, Molecular Cloning: A Laboratory Manual. 2nd, ed., Cold Spring Harbor Laboratory, Cold Spring Harbor Laboratory Press, Cold Spring Harbor, N.Y.). Moreover, a nucleic acid molecule encompassing all or a portion of one of the disclosed sequences can be isolated by the polymerase chain reaction using oligonucleotide primers designed based upon this sequence (e.g., a nucleic acid molecule encompassing all or a portion of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123 can be isolated by the polymerase chain reaction using oligonucleotide primers designed based upon this same sequence. For example, mRNA can be isolated from plant cells (e.g., by the guanidinium-thiocyanate extraction procedure of Chirgwin et al., 1979, Biochemistry 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the polynucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an LMP nucleotide sequence can be prepared by standard synthetic techniques, e.g., using an automated DNA synthesizer.

In a preferred embodiment, an isolated nucleic acid of the invention comprises one of the polynucleotide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123. These polynucleotides correspond to the *Arabidopsis thaliana, Brassica napus*, and *Helianthus annuus* LMP cDNAs of the invention. These cDNAs comprise sequences encoding LMPs (i.e., the "coding region" or open reading frame (ORF)). Alternatively, the nucleic acid molecules also may comprise 5' untranslated sequences and 3' untranslated sequences of the polynucleotide sequences described herein or can contain whole genomic fragments isolated from genomic DNA. The particular polynucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123 have been given an identifying entry number (e.g. Osw14). These sequences represent the coding region or open reading frame, and the putative functions of the encoded polypeptides are indicated in Table 3.

TABLE 3

Putative LMP Functions

| Sequence code | Function | ORF position |
|---|---|---|
| osw14 | RNA binding factor | 1–2976 |
| osw15 | Regulator of proteasomes and transcription factors | 1–1014 |
| osw16 | γ-COP/Adaptin | 1–2661 |
| osw17 | Strictosidine synthase | 1–1131 |
| osw18 | Strictosidine synthase | 1–1113 |
| osw20 | GDSL-like lipase | 1–1119 |
| osw21 | Retinaldehyde binding prot. | 1–447 |
| osw22 | Lipid binding protein | 1–1134 |
| osw23 | Lipocalin and fattay acid binding protein | 1–594 |
| osw24 | Diacylglycerol binding protein | 1–780 |
| osw26 | Beta-hydroxysteroid dehydrogenase | 1–915 |
| JB69 | Aspartate protease | 1–1521 |
| JB70 | Aspartate protease | 1–1542 |
| JB71 | Aspartate protease | 1–1527 |

TABLE 3-continued

Putative LMP Functions

| Sequence code | Function | ORF position |
|---|---|---|
| JB080 | Palmitoyl-protein thioesterase precursor-like | 1–951 |
| JB082 | Laccase (diphenol oxidase) | 1–1473 |
| JB084 | Alanine aminotransferase, putative | 1–1470 |
| JB085 | Peptidylprolyl isomerase | 1–519 |
| JB088 | Cysteine proteinase-like protein | 1–1095 |
| JB089 | Plant invertase/pectin methylesterase inhibitor | 1–516 |
| JB090 | Gamma interferon inducible lysosomal thiol reductase | 1–702 |
| JB091 | Blue copper binding-like protein | 1–591 |
| JB093 | Embryonic abundant protein | 1–459 |
| ToZ001 | Glycerinaldehyde-3-phosphate dehydrogenase | 1–1191 |
| ToZ002 | Glycerol kinase | 1–1569 |
| ToZ003 | Phosphomannomutase | 1–741 |
| ToZ004 | Choline/ethanolamine phosphotransferase | 1–1170 |
| ToZ005 | Choline/ethanolamine kinase | 1–2019 |
| ToZ011 | Fatty acid elongase ELO-like | 1–897 |
| ToZ012 | Fatty acid elongase ELO-like | 1–837 |

TABLE 4

Grouping of LMPs Based on Functional Protein Domains

| Functional category | SEQ ID: | SEQ Code: | Functional domain | Domain position (aa) |
|---|---|---|---|---|
| Fatty acid metabolism | 29 | JB80 | Palmitoyl protein thioesterase (PFAM) | 21–297 |
|  | 57 | ToZ11 | GNS1/SUR4 family (PFAM) | 1–277 |
|  | 59 | ToZ12 | GNS1/SUR4 family (PFAM) | 1–277 |
| Intracellular transport | 5 | Osw16 | Adaptin N (PFAM) | 25–527 |
|  | 51 | ToZ03 | Eukaryotic phosphomannomutase (PFAM) | 29–246 11–234 |
| Lipid metabolism | 11 | Osw20 | GDSL-like Lipase/Acylhydrolase (PFAM) | 37–333 |
|  | 13 | Osw21 | (acyl-carrier-protein) S-malonyltransferase (COG) Cellular retinaldehyde-binding protein (BLOCKS) | 3–147 111–118 |
|  | 15 | Osw22 | *Arabidopsis* protein of unknown function (PFAM) Cellular retinaldehyde-binding protein (BLOCKS) Sterol regulatory element binding protein site (BLOCKS) | 125–236 15–29 165–177 |
|  | 19 | Osw24 | Phorbol esters/diacylglycerol binding domain (BLOCKS) | 22–34 |
|  | 21 | Osw26 | 3-Beta hydroxysteroid dehydrogenase (BLOCKS) | 65–95 |
|  | 53 | ToZ04 | CDP-alcohol phosphatidyltransferase (PFAM) | 86–224 |
|  | 55 | ToZ05 | Choline/ethanolamine kinase (PFAM) | 397–655 |
| Oxidoreductases | 41 | JB90 | Gamma interferon inducible lysosomal thiol reductase (PFAM) | 32–136 |
|  | 31 | JB82 | Multicopper oxidase (PFAM) | 72–230 309–472 |
|  | 43 | JB91 | Type-1 copper (blue) domain (BLOCKS) Plastocyanin-like domain (PFAM) | 105–123 33–117 |
| Precuror supply | 33 | JB84 | Aminotransferase class I and II (PFAM) | 140–480 |

TABLE 4-continued

Grouping of LMPs Based on Functional Protein Domains

| Functional category | SEQ ID: | SEQ Code: | Functional domain | Domain position (aa) |
|---|---|---|---|---|
| | 39 | JB89 | Plant invertase/pectin methylesterase inhibitor (PFAM) | 19–167 |
| | 47 | ToZ01 | Glyceraldehyde 3-phosphate dehydrogenase (PFAM) | 61–213<br>213–374 |
| | 49 | ToZ02 | FGGY family of carbohydrate kinases (PFAM) | 7–262<br>265–501 |
| Proteases | 23 | JB69 | Eukaryotic aspartyl protease (PFAM) | 30–505 |
| | 25 | JB70 | Eukaryotic aspartyl protease (PFAM) | 44–521 |
| | 27 | JB71 | Eukaryotic aspartyl protease (PFAM) | 41–516 |
| | 37 | JB88 | Papain family cysteine protease (PFAM) | 137–352 |
| Protein stability | 45 | JB93 | Small hydrophilic plant seed protein (PFAM) | 1–90<br>92–152 |
| Protein synthesis | 35 | JB85 | Cyclophilin type peptidyl-prolyl cis-trans isomerase (PFAM) | 5–172 |
| RNA-binding proteins | 1 | Osw14 | TUDOR (PFAM) | 733–806 |
| RNA-binding proteins/Lipid signal transduction | 17 | Osw23 | Pumilio-family RNA binding repeat (PFAM)<br>Lipocalin and cytosolic fatty-acid binding protein (Blocks) | 4–153<br>127–137 |
| Signal Transduction | 3 | Osw15 | Mov34 (PFAM) | 20–128 |
| Alkaloid biosynthesis | 7 | Osw17 | Strictosidine synthase (PFAM) | 10–365 |
| | 9 | Osw18 | Strictosidine synthase (PFAM) | 5–364 |

In another preferred embodiment, an isolated nucleic acid molecule of the present invention encodes a polypeptide that is able to participate in the metabolism of seed storage compounds such as lipids, starch, and seed storage proteins, and/or that contains a DNA-binding (or transcription factor) domain, or an RNA-binding domain. Examples of isolated nucleic acids that encode LMPs containing such domains can be found in Table 4. Examples of nucleic acids encoding an LMP with an RNA-binding domain are SEQ ID NO:1 and SEQ ID NO:17. An example of a nucleic acid encoding an LMP with a signal transduction domain includes SEQ ID NO:3. Examples of nucleic acids encoding LMPs containing a protease domain include those shown in SEQ ID NO:23, SEQ ID NO:25, SEQ ID NO:27, and SEQ ID NO:37. Examples of nucleic acids encoding LMPs containing a lipid metabolism domain include those shown in SEQ ID NO:11, SEQ ID NO:13, SEQ ID NO:15, SEQ ID NO:19, SEQ ID NO:21, SEQ ID NO:53, SEQ ID NO:55, and SEQ ID NO:121. Examples of nucleic acids encoding LMPs containing a oxidoreductase domain include those shown in SEQ ID NO:31, SEQ ID NO:41, and SEQ ID NO:43. Examples of nucleic acids encoding LMPs containing a fatty acid metabolism domain include those shown in SEQ ID NO:29, SEQ ID NO:57, and SEQ ID NO:59. Examples of nucleic acids encoding LMPs containing a protein synthesis domain include those shown in SEQ ID NO:35 and SEQ ID NO:45. Examples of nucleic acids encoding LMPs containing an alkaloid biosynthesis domain include those shown in SEQ ID NO:7 and SEQ ID NO:9. Examples of nucleic acids encoding LMPs containing a biosynthesis precursur supply domain include those shown in SEQ ID NO:33, SEQ ID NO:39, SEQ ID NO:47, and SEQ ID NO:49. Examples of nucleic acids encoding LMPs containing an intracellular transport domain include those shown in SEQ ID NO:5 and SEQ ID NO:51.

In another preferred embodiment, an isolated nucleic acid molecule of the invention comprises a nucleic acid molecule, which is a complement of one of the polynucleotide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123, or a portion thereof. A nucleic acid molecule which is complementary to one of the disclosed polynucleotide sequences is one which is sufficiently complementary to one of the disclosed polynucleotide sequences such that it can hybridize to one of the disclosed polynucleotide sequences, thereby forming a stable duplex.

In another preferred embodiment, an isolated nucleic acid of the invention comprises a polynucleotide sequence encoding a polypeptide selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:122.

In still another preferred embodiment, an isolated nucleic acid molecule of the invention comprises a polynucleotide sequence which is at least about 50-60%, preferably at least about 60-70%, more preferably at least about 70-80%, 80-90%, or 90-95%, and even more preferably at least about 95%, 96%, 97%, 98%, 99%, or more homologous to a full-length polynucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123, or a portion thereof. In an additional preferred embodiment, an isolated nucleic acid molecule of the invention comprises a polynucleotide sequence which hybridizes, e.g., hybridizes under stringent conditions, to one of these disclosed polynucleotide sequences, or a portion thereof. These stringent conditions include washing with a solution having a salt concentration of about 0.02M at pH 7 and about 60° C. In another embodiment, the stringent conditions comprise hybridization in a 6× sodium chloride/sodium citrate (6×SSC) solution at 45° C. In yet another embodiment, the stringent conditions comprise hybridization in a 6× sodium chloride/sodium citrate (6×SSC) solution at 65° C.

Moreover, the nucleic acid molecule of the invention can comprise only a portion of the coding region of one of the disclosed sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123, for example, a fragment which can be used as a probe or primer or a fragment encoding a biologically active portion of a LMP. The polynucleotide sequences determined from the cloning of the LMP genes from *Arabidopsis thaliana*, *Brassica napus*, and *Helianthus annuus* allows for the generation of probes and primers designed for use in identifying and/or cloning LMP homologues in other cell types and organisms, as well as LMP homologues from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123, an anti-sense sequence of one of these sequences, or naturally occurring mutants thereof. Primers based on one of these polynucleotide sequences can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a LMP, such as by measuring a level of a LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid sequence encoded by one of the disclosed polynucleotide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:121 such that the protein or portion thereof maintains the same or a similar function as the wild-type protein. As used herein, the language "sufficiently homologous" refers to proteins or portions thereof which have amino acid sequences which include a minimum number of identical or equivalent amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. As used herein, an "equivalent" amino acid residue is, for example, an amino acid residue which has a similar side chain as a particular amino acid residue that is encoded by one of these disclosed polynucleotide sequences. Regulatory proteins, such as RNA binding proteins, protein stability and breakdown proteins, signal transduction proteins, or protein members of metabolic pathways such as the lipid, starch, and protein biosynthetic pathways as well as pathways for the precursor supply of these pathways, or membrane transport systems, may play a role in the biosynthesis of seed storage compounds. Examples of such activities are described herein (see putative annotations in Table 3). Examples of LMP-encoding nucleic acid sequences are SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 121, or SEQ ID NO: 123.

As altered or increased sugar and/or fatty acid production is a general trait wished to be inherited into a wide variety of plants like maize, wheat, rye, oat, triticale, rice, barley, soybean, peanut, cotton, rapeseed, canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for genetic engineering as one further embodiment of the present invention. As used herein, the term "forage crop" includes, but is not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover. In a preferred embodiment, the plant is an oil producing species or oilseed species selected from the group consisting of rapeseed, canola, linseed, soybean, sunflower, maize, oat, rye, barley, wheat, pepper, tagetes, cotton, oil palm, coconut palm, flax, castor, and peanut, for example. See, e.g., Kinney et al. (1994, Current Opin. in Biotech. 5: 144-151), Töpfer et al. (1995, Science 268:681-686), and Oil Crops of the World-Their Breeding and Utilization (1989, eds. Röbbelen, Downey, and Ashri).

Portions of proteins encoded by the LMP nucleic acid molecules of the invention are preferably biologically active portions of one of the LMPs. As used herein, the term "biologically active portion of an LMP" is intended to include a portion, e.g., a domain/motif, of an LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether an LMP or a biologically active portion thereof can participate in the metabolism of compounds necessary for the production of seed storage compounds and cellular membranes, an assay of enzymatic activity may be performed. Such assay methods are well known to those skilled in the art, and specific references are cited in Example 15 herein.

Biologically active portions of an LMP include peptides comprising amino acid sequences derived from the amino acid sequence of an LMP (e.g., an amino acid sequence encoded by a nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123) or the amino acid sequence of a protein homologous to an LMP, which include fewer amino acids than a full length LMP or the full length protein which is homologous to an LMP and exhibits at least one activity of an LMP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an LMP. Moreover, other biologically active portions, in which other regions of the protein are deleted, can be prepared by recombinant techniques and evaluated for one or more of the activities described herein. Preferably, the biologically active portions of an LMP include one or more selected domains/motifs or portions thereof having biological activity.

Additional nucleic acid fragments encoding biologically active portions of an LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123, and portions thereof, due to degeneracy of the genetic code and thus encode the same LMP as that encoded by the disclosed polynucleotide sequences. In a further embodiment, the nucleic acid molecule of the invention encodes a full length polypeptide which is substantially homologous to an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, or SEQ ID NO:122. In one embodiment, the full-length nucleic acid or protein or fragment of the nucleic acid or protein is from *Arabidopsis thaliana*, *Brassica napus*, and *Helianthus annuus*.

In addition to the *Arabidopsis thaliana*, *Brassica napus*, and *Helianthus annuus* LMP polynucleotide sequences described herein, it will be appreciated by those skilled in the art that DNA sequence polymorphisms that lead to changes in the amino acid sequences of LMPs may exist within a population (e.g., the *Arabidopsis thaliana*, *Brassica napus*, and *Helianthus annuus* population). Such genetic polymorphism in the LMP gene may exist among individuals within a population due to natural variation. As used herein, the terms "gene" and "recombinant gene" refer to nucleic acid molecules comprising an open reading frame encoding an LMP, preferably an *Arabidopsis thaliana*, *Brassica napus*, and *Helianthus annuus* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana*, non-*Brassica napus*, or non-*Helianthus annuus* orthologs of the *Arabidopsis thaliana*, *Brassica napus*, and *Helianthus annuus* LMP cDNA of the invention can be isolated based on their homology to the *Arabidopsis thaliana*, *Brassica napus*, and *Helianthus annuus* LMP nucleic acids disclosed herein using the *Arabidopsis thaliana*, *Brassica napus*, or *Helianthus annuus* cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising one of the polynucleotide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123. In other embodiments, the nucleic acid is at least 30, 50, 60, 100, 250, or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75%, or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. In another embodiment, the stringent conditions comprise hybridization in a 6× sodium chloride/sodium citrate (6×SSC) solution at 45° C. In yet another embodiment, the stringent conditions comprise hybridization in a 6×SSC solution at 65° C. Preferably, an isolated nucleic acid molecule of the invention that hybridizes under stringent conditions to one of the disclosed polynucleotide sequences corresponds to a naturally occurring nucleic acid molecule. As used herein, a "naturally-occurring" nucleic acid molecule refers to an RNA or DNA molecule having a polynucleotide sequence that occurs in nature (e.g., encodes a natural protein). In one embodiment, the nucleic acid encodes a natural *Arabidopsis thaliana, Brassica napus*, or *Helianthus annuus* LMP.

In addition to naturally-occurring variants of the LMP sequence that may exist in the population, the skilled artisan will further appreciate that changes can be introduced by mutation into one of the disclosed polynucleotide sequences, thereby leading to changes in the amino acid sequence of the encoded LMP, without altering the functional ability of the LMP. For example, nucleotide substitutions leading to amino acid substitutions at "non-essential" amino acid residues can be made in one of the disclosed polynucleotide sequences. A "non-essential" amino acid residue is a residue that can be altered from the wild-type sequence of one of the disclosed LMPs (SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, or SEQ ID NO:122) without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment, the isolated nucleic acid molecule comprises a nucleotide sequence encoding a protein, wherein the protein comprises an amino acid sequence at least about 50% homologous to an amino acid sequence encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123 and is capable of participation in the metabolism of compounds necessary for the production of seed storage compounds in *Arabidopsis thaliana, Brassica napus*, and *Helianthus annuus*, or cellular membranes, or has one or more activities set forth in Table 3. Preferably, the protein encoded by the nucleic acid molecule is at least about 50-60% homologous to one of the sequences encoded by one of the disclosed nucleic acids, more preferably at least about 60-70% homologous to one of the sequences encoded by one of the disclosed nucleic acids, even more preferably at least about 70-80%, 80-90%, or 90-95% homologous to one of the sequences encoded by one of the disclosed nucleic acids, and most preferably at least about 96%, 97%, 98%, or 99% homologous to one of the sequences encoded by one of the disclosed nucleic acids.

To determine the percent homology of two amino acid sequences (e.g., one of the sequences encoded by a nucleic acid disclosed herein and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences encoded by the disclosed nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123) is occupied by the same amino acid residue or nucleotide as the corresponding position in the other sequence (e.g., a mutant form of the sequence encoded by the disclosed nucleic acid), then the molecules are homologous at that position. As used herein, amino acid or nucleic acid "homology" is equivalent to amino acid or nucleic acid "identity." The percent homology between the two sequences is a function of the number of identical positions shared by the sequences (i.e., % homology=numbers of identical positions/total numbers of positions×100).

An isolated nucleic acid molecule encoding an LMP homologous to a protein sequence encoded by a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:121, or SEQ ID NO:123 can be created by introducing one or more nucleotide substitutions, additions, or deletions into the disclosed polynucleotide sequence such that one or more amino acid substitutions, additions, or deletions are introduced into the encoded protein. Mutations can be introduced into one of the disclosed polynucleotide sequences by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted non-essential amino acid residue in an LMP is preferably replaced with another amino acid residue from the same side chain family. Alternatively, in another embodiment, mutations can be introduced randomly along all or part of an LMP coding sequence, such as by saturation mutagenesis, and the resultant mutants can be screened for an LMP activity described herein to identify mutants that retain LMP activity. Following mutagenesis of one of the disclosed polynucleotide sequences, the encoded protein can be expressed recombinantly and the activity of the protein can be determined using, for example, assays described herein (See, e.g., Examples 15-16 below).

LMPs are preferably produced by recombinant DNA techniques. For example, a nucleic acid molecule encoding the protein is cloned into an expression vector (as described herein), the expression vector is introduced into a host cell (as described herein), and the LMP is expressed in the host cell. The LMP can then be isolated from the cells by an appropriate purification scheme using standard protein purification techniques. Alternative to recombinant expression, an LMP or peptide thereof can be synthesized chemically using standard peptide synthesis techniques. Moreover, native LMP can be isolated from cells, for example, using an anti-LMP antibody which can be produced by standard techniques utilizing an LMP or fragment thereof of this invention.

The invention also provides LMP chimeric or fusion proteins. As used herein, an LMP "chimeric protein" or "fusion protein" comprises an LMP polypeptide operatively linked to a non-LMP polypeptide. An "LMP polypeptide" refers to a polypeptide having an amino acid sequence corresponding to an LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. As used herein with respect to the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is an LMP containing a heterologous signal sequence at its N-terminus. In certain host cells (e.g., mammalian host cells), expression and/or secretion of an LMP can be increased through use of a heterologous signal sequence.

Preferably, an LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (See, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding an LMP. The term "coding region" refers to the region of the nucleotide sequence comprising codons, which are translated into amino acid residues. In another embodiment, the antisense nucleic acid molecule is antisense to a "noncoding region" of the coding strand of a nucleotide sequence encoding LMP. The term "noncoding region" refers to 5' and 3' sequences which flank the coding region that are not translated into amino acids (i.e., also referred to as 5' and 3' untranslated regions).

Given the coding strand sequences encoding LMP disclosed herein (e.g., the full-length polynucleotide sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:121), antisense nucleic acids of the invention can be designed according to the rules of Watson and Crick base pairing. The antisense nucleic acid molecule can be complementary to the entire coding region of the LMP mRNA, but more preferably is an oligonucleotide which is antisense to only a portion of the coding or noncoding region of the LMP mRNA. For example, the antisense oligonucleotide can be complementary to the region surrounding the translation start site of the LMP mRNA. An antisense oligonucleotide can be, for example, about 5, 10, 15, 20, 25, 30, 35, 40, 45, or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydro-uracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methyl-cytosine, N-6-adenine, 7-methylguanine, 5-methylaminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct.

The antisense nucleic acid molecules of the invention are typically administered to a cell or generated in situ such that they hybridize with or bind to cellular mRNA and/or genomic DNA encoding an LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an anomeric nucleic acid molecule. An anomeric nucleic acid molecule forms specific double-stranded hybrids with complementary RNA in which, contrary to the usual units, the strands run parallel to each other (Gaultier et al., 1987, Nucleic Acids Res. 15:6625-6641). The antisense nucleic acid molecule can also comprise a 2'-o-methyl-ribonucleotide (Inoue et al., 1987, Nucleic Acids Res. 15:6131-6148) or a chimeric RNA-DNA analogue (Inoue et al., 1987, FEBS Lett. 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff & Gerlach, 1988, Nature 334:585-591)) can be used to catalytically cleave LMP mRNA transcripts to thereby inhibit translation of LMP mRNA. A ribozyme having specificity for an LMP-encoding nucleic acid can be designed based upon the nucleotide sequence of an LMP cDNA disclosed herein or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in an LMP-encoding mRNA (See, e.g., U.S. Pat. Nos. 4,987,071 and 5,116,742 to Cech et al.). Alternatively, LMP mRNA can be used to select a catalytic RNA having a specific ribonuclease activity from a pool of RNA molecules (See, e.g., Bartel, D. & Szostak J. W. 1993, Science 261:1411-1418).

Alternatively, LMP gene expression can be inhibited by targeting nucleotide sequences complementary to the regulatory region of an LMP nucleotide sequence (e.g., an LMP promoter and/or enhancers) to form triple helical structures that prevent transcription of an LMP gene in target cells (See generally, Helene C., 1991, Anticancer Drug Des. 6:569-84; Helene C. et al., 1992, Ann. N.Y. Acad. Sci. 660:27-36; and Maher, L. J., 1992, Bioassays 14:807-15).

Another aspect of the invention pertains to vectors, preferably expression vectors, containing a nucleic acid encoding an LMP (or a portion thereof). As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990) and Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those, which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovirus expression vectors), yeast and other fungal cells (See Romanos M. A. et al., 1992, Foreign gene expression in yeast: a review, Yeast 8:423-488; van den Hondel, C.A.M.J.J. et al., 1991, Heterologous gene expression in filamentous fungi, in: More Gene Manipulations in Fungi, Bennet & Lasure, eds., p. 396-428:Academic Press: an Diego; and van den Hondel & Punt, 1991, Gene transfer systems and vector development for filamentous fungi, in: Applied Molecular Genetics of Fungi, Peberdy et al., eds., p. 1-28, Cambridge University Press: Cambridge), algae (Falciatore et al., 1999, Marine Biotechnology 1:239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia*, especially of the genus *Stylonychia lemnae* with vectors following a transformation method as described in WO 98/01572, and multicellular plant cells (See Schmidt & Willmitzer, 1988, High efficiency *Agrobacterium tumefaciens*-mediated transformation of *Arabidopsis thaliana* leaf and cotyledon plants, Plant Cell Rep.: 583-586; Plant Molecular Biology and Biotechnology, C Press, Boca Raton, Fla., chapter 6/7, S. 71-119 (1993); White, Jenes et al., Techniques for Gene Transfer, in: Transgenic Plants, Vol. 1, Engineering and Utilization, eds.: Kung and Wu, Academic Press 1993, 128-43; Potrykus, 1991, Annu. Rev. Plant Physiol. Plant Mol. Biol. 42:205-225 (and references cited therein)), or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

Typical fusion expression vectors include pGEX (Pharmacia Biotech Inc; Smith & Johnson, 1988, Gene 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al., 1988, Gene 69:301-315) and pET 11d (Studier et al., 1990, Gene Expression Technology:Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S., 1990, Gene Expression Technology:Methods in Enzymology 185: 119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al., 1992, Nucleic Acids Res. 20: 2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al., 1987, Embo J. 6:229-234), pMFa (Kurdjan & Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt, 1991, "Gene transfer systems and vector development for filamentous fungi, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al., 1983, Mol. Cell Biol. 3:2156-2165) and the pVL series (Lucklow & Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, Fritsh and Maniatis, Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the LMPs of the invention may be expressed in uni-cellular plant cells (such as algae, see Falciatore et al., 1999, Marine Biotechnology 1:239-251 and references therein) and plant cells from higher plants (e.g., the spermatophytes, such as crop plants). Examples of plant expression vectors include those detailed in: Becker, Kemper, Schell and Masterson (1992, Plant Mol. Biol. 20:1195-1197) and Bevan (1984, "Binary *Agrobacterium* vectors for plant transformation, Nucleic Acids Res. 12:8711-8721; Vectors for Gene Transfer in Higher Plants; in: Transgenic Plants, Vol. 1, Engineering and Utilization, eds.: Kung und R. Wu, Academic Press, 1993, S. 15-38).

A plant expression cassette preferably contains regulatory sequences capable to drive gene expression in plant cells and which are operatively linked so that each sequence can fulfil its function such as termination of transcription, including polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3:835) or functional equivalents thereof but also all other terminators functionally active in plants are suitable.

As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the protein per RNA ratio (Gallie et al. 1987, Nucleic Acids Res. 15:8693-8711).

Plant gene expression has to be operatively linked to an appropriate promoter conferring gene expression in a timely, cell or tissue specific manner. Preferred are promoters driving constitutive expression (Benfey et al. 1989, EMBO J. 8:2195-2202) like those derived from plant viruses like the 35S CAMV (Franck et al. 1980, Cell 21:285-294), the 19S CaMV (see also U.S. Pat. No. 5,352,605 and WO 84/02913), or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include, but are not limited to, the napin-gene promoter from rapeseed (U.S. Pat. No. 5,608,152), the USP-promoter from *Vicia faba* (Baeumlein et al. 1991, Mol. Gen. Genetics 225: 459-67), the oleosin-promoter from *Arabidopsis* (WO 98/45461), the phaseolin-promoter from *Phaseolus vulgaris* (U.S. Pat. No. 5,504, 200), the Bce4-promoter from *Brassica* (WO9113980) or the legumin B4 promoter (LeB4; Baeumlein et al. 1992, Plant J. 2:233-239) as well as promoters conferring seed specific expression in monocot plants like maize, barley, wheat, rye, rice, etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the Sorghum kasirin-gene, and the rye secalin gene).

Plant gene expression can also be facilitated via an inducible promoter (for review, see Gatz 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404), and an ethanol inducible promoter (WO 93/21334).

Promoters responding to biotic or abiotic stress conditions are also suitable promoters such as the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (WO 96/12814), and the wound-inducible pinII-promoter (EP 375091).

Other preferred sequences for use in plant gene expression cassettes are targeting-sequences necessary to direct the gene-product in its appropriate cell compartment (for review, see Kermode 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes, and other compartments of plant cells. Also especially suited are promoters that confer plastid-specific gene expression, as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an LMP can be expressed in bacterial cells, insect cells, fungal cells, mammalian cells (such as Chinese hamster ovary cells (CHO) or COS cells), algae, ciliates or plant cells. Other suitable host cells are known to those skilled in the art.

Vector DNA can be introduced into prokaryotic or eukaryotic cells via conventional transformation or transfection techniques. As used herein, the terms "transformation" and "transfection," "conjugation," and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, Molecular Cloning: A Laboratory Manual. 2nd, ed., Cold Spring Harbor Laboratory, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycin, and methotrexate, or in plants that confer resistance towards an herbicide such as glyphosate or glufosinate. A nucleic acid encoding a selectable marker can be introduced into a host cell on the same vector as that encoding an LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of an LMP gene into which a deletion, addition or substitution has been introduced to thereby alter, e.g., functionally disrupt, the LMP gene. Preferably, this LMP gene is an *Arabidopsis thaliana, Brassica napus*, and *Helianthus annuus* LMP gene, but it can be a homolog from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al., 1999, Nucleic Acids Res. 27:1323-1330 and Kmiec 1999, American Scientist 87:240-247). Homologous recombination procedures in *Arabidopsis thaliana* are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flanking LMP nucleic acid is of sufficient length for successful homologous recombination with the endogenous gene. Typically, several hundreds of base pairs up to kilobases of flanking DNA (both at the 5' and 3' ends) are included in the vector (see, e.g., Thomas & Capecchi, 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems which allow for regulated expression of the introduced gene. For example, inclusion of an LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) an LMP. Accordingly, the invention further provides methods for producing LMPs using the host cells of the invention. In one embodiment, the method comprises culturing a host cell of the invention (into which a recombinant expression vector encoding an LMP has been introduced, or which contains a wild-type or altered LMP gene in its genome) in a suitable medium until the LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals which are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana*, *Brassica napus*, or *Helianthus annuus* LMP in plants other than *Arabidopsis thaliana*, *Brassica napus*, or *Helianthus annuus*, or microorganisms, algae, or fungi.

An isolated LMP or a portion thereof of the invention can participate in the metabolism of compounds necessary for the production of seed storage compounds in *Arabidopsis thaliana*, *Brassica napus*, or *Helianthus annuus*, or of cellular membranes, or has one or more of the activities set forth in Table 3. In preferred embodiments, the protein or portion thereof comprises an amino acid sequence which is sufficiently homologous to an amino acid sequence encoded by one of the disclosed nucleic acids shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:121, such that the protein or portion thereof maintains the ability to participate in the metabolism of compounds necessary for the construction of cellular membranes in *Arabidopsis thaliana*, *Brassica napus*, or *Helianthus annuus*, or in the transport of molecules across these membranes. The portion of the protein is preferably a biologically active portion as described herein. In another preferred embodiment, an LMP of the invention has an amino acid sequence encoded by one of these disclosed nucleic acids. In yet another preferred embodiment, the LMP has an amino acid sequence which is encoded by a polynucleotide sequence which hybridizes, e.g., hybridizes under stringent conditions, to one of these disclosed nucleic acids. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99% or more homologous to an amino acid sequence encoded by one of these disclosed nucleic acids. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to one of the disclosed nucleic acids, and which can participate in the metabolism of compounds necessary for the construction of cellular membranes in *Arabidopsis thaliana*, *Brassica napus*, or *Helianthus annuus*, or in the transport of molecules across these membranes, or which has one or more of the activities set forth in Table 3.

In other embodiments, the LMP is substantially homologous to an amino acid sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:121 and retains the functional activity of the protein encoded by that sequence yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence and which has at least one of the LMP activities described herein. In another embodiment, the invention pertains to a full-length *Arabidopsis thaliana*, *Brassica napus*, or *Helianthus annuus* protein which is substantially homologous to an entire amino acid sequence encoded by a nucleic acid shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:121.

Dominant negative mutations or trans-dominant suppression can be used to reduce the activity of an LMP in transgenics seeds in order to change the levels of seed storage compounds. To achieve this, a mutation that abolishes the activity of the LMP is created and the inactive non-functional LMP gene is overexpressed in the transgenic plant. The inactive trans-dominant LMP protein competes with the active endogenous LMP protein for substrate or interactions with other proteins and dilutes out the activity of the active LMP. In this way the biological activity of the LMP is reduced without actually modifying the expression of the endogenous LMP gene. This strategy was used by Pontier et al. to modulate the activity of plant transcription factors (Pontier et al., 2001, Plant J. 27(6): 529-38).

Homologs of the LMP can be generated by mutagenesis, e.g., discrete point mutation or truncation of the LMP. As used herein, the term "homolog" refers to a variant form of the LMP which acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP by, for example, competitively binding to a downstream or upstream member of the cell membrane component metabolic cascade which includes the LMP, or by binding to an LMP which mediates transport of compounds across such membranes, thereby preventing translocation from taking place.

In an alternative embodiment, homologs of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods which can be used to produce libraries of potential LMP homologs from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (see, e.g., Narang, 1983, Tetrahedron 39:3; Itakura et al., 1984, Annu. Rev. Biochem. 53:323; Itakura et al., 1984, Science 198:1056; Ike et al., 1983, Nucleic Acids Res. 11:477).

In addition, libraries of fragments of the LMP coding sequences can be used to generate a variegated population of LMP fragments for screening and subsequent selection of homologs of an LMP. In one embodiment, a library of coding sequence fragments can be generated by treating a double stranded PCR fragment of an LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LMP homologs (Arkin & Yourvan, 1992, Proc. Natl. Acad. Sci. USA 89:7811-7815; Delgrave et al., 1993, Protein Engineering 6:327-331).

In another embodiment, cell based assays can be exploited to analyze a variegated LMP library, using methods well known in the art.

The nucleic acid molecules, proteins, protein homologs, fusion proteins, primers, vectors, and host cells described herein can be used in one or more of the following methods: identification of *Arabidopsis thaliana, Brassica napus, Helianthus annuus*, and related organisms; mapping of genomes of organisms related to *Arabidopsis thaliana, Brassica napus*, or *Helianthus annuus*; identification and localization of *Arabidopsis thaliana, Brassica napus*, or *Helianthus annuus* sequences of interest; evolutionary studies; determination of LMP regions required for function; modulation of an LMP activity; modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as *Brassica napus, Helianthus annuus*, and soybean, which require light to drive photosynthesis and growth. Plants like *Arabidopsis thaliana* and *Brassica napus* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, they may be used to identify an organism as being *Arabidopsis thaliana, Brassica napus*, or *Helianthus annuus*, or a close relative thereof. Also, they may be used to identify the presence of *Arabidopsis thaliana, Brassica napus, Helianthus annuus*, or a relative thereof in a mixed population of microorganisms. The invention provides the nucleic acid sequences of a number of *Arabidopsis thaliana, Brassica napus*, and *Helianthus annuus* genes; by probing the extracted genomic DNA of a culture of a unique or mixed population of microorganisms under stringent conditions with a probe spanning a region of an *Arabidopsis thaliana, Brassica napus*, or *Helianthus annuus* gene which is unique to this organism, one can ascertain whether this organism is present.

Further, the nucleic acid and protein molecules of the invention may serve as markers for specific regions of the genome. This has utility not only in the mapping of the genome, but also for functional studies of *Arabidopsis thaliana, Brassica napus*, and *Helianthus annuus* proteins. For example, to identify the region of the genome to which a particular *Arabidopsis thaliana, Brassica napus*, or *Helianthus annuus* DNA-binding protein binds, the *Arabidopsis thaliana, Brassica napus*, or *Helianthus annuus* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana, Brassica napus*, or *Helianthus annuus*, and when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants. Similarly, binding to mRNA sequences by *Arabidopsis thaliana, Brassica napus* and *Helianthus annuus* RNA binding proteins of the invention can be determined. In another example of functional studies *Arabidopsis thaliana, Brassica napus*, and *Helianthus annuus* proteins of the invention involved in proteolysis and protein stability can be used to identify partners in protein-protein interaction assays, for example, in blue native gels or yeast two hybrid screens.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of an LMP of the invention may directly affect the accumulation of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where overexpression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al., 2000, Plant J. 24:383-396) and the lipid composition in leaves and roots (Härtel et al., 2000, Proc. Natl. Acad. Sci. USA 97:10649-10654). Likewise, the activity of the plant ACCase has been demonstrated to be regulated by phosphorylation (Savage & Ohlrogge, 1999, Plant J. 18:521-527) and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/or membrane protein regulation occur in envelopes (see, e.g., Müller et al., 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al., 2001, Plant J. 25:295-303). For more examples, see also the "Background of the Invention" section above.

The present invention also provides antibodies which specifically bind to an LMP polypeptide, or a portion thereof, as encoded by a nucleic acid disclosed herein or as described herein.

Antibodies can be made by many well-known methods (see, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (see, for example, Kelly et al., 1992, Bio/Technology 10:163-167; Bebbington et al., 1992, Bio/Technology 10:169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, N.Y. (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, N.Y., 1988).

Throughout this application, various publications are referenced. The disclosures of all of these publications and those references cited within those publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics," Cold Spring Harbor Laboratory Press: ISBN 0-87969-451-3).

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg), and Sigma (Deisenhofen). Solutions were prepared using purified, pyrogen-free water, designated as $H_2O$ in the following text, from a MILLI-Q water system water purification plant (Millipore, Eschborn). Restriction endonucleases, DNA-modifying enzymes, and molecular biology kits were obtained from the companies AGS (Heidelberg), Armersham (Braunschweig), Biometra (Göttingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden), and Stratagene (Amsterdam, Netherlands). They were used, if not mentioned otherwise, according to the manufacturer's instructions.

c) Plant Material:

*Arabidopsis thaliana*

Seeds were obtained from the *Arabidopsis* stock center. The ecotypes Columbia 0 and Landsberg erecta were used to analyse developing seeds and siliques of early to mid stage (1 to 8 days after flowering) to late stage seeds and siliques (8 to 15 days after flowering).

*Brassica napus* Variety Westar

*Brassica napus* cv. Westar plants were used for this study to isolate developing seeds. Seeds were collected from developing seed pods 3-5 weeks after flowering.

*Brassica napus* AC Excel and Cresor Varieties

*Brassica napus* varieties AC Excel and Cresor were used for this study to create cDNA libraries. Seed, seed pod, flower, leaf, stem, and root tissues were collected from plants that were in some cases dark-, salt-, heat-, or drought-treated. However, this study focused on the use of seed and seed pod tissues for cDNA libraries.

*Helianthus annuus* Variety Sigma

*Helianthus annuus* cv. Sigma plants were used for this study to create cDNA libraries from developing seeds.

d) Plant Growth:

*Arabidopsis thaliana*

Plants were grown on soil under standard conditions as described in Focks & Benning (1998, Plant Physiol. 118: 91-101).

*Brassica napus* Variety Westar

Plants were either grown in the field or in Metromix (Scotts, Marysville, Ohio) in the greenhouse with supplementary lighting.

*Brassica napus* AC Excel and Cresor Varieties

Plants (AC Excel, except where mentioned) were grown in Metromix (Scotts, Marysville, Ohio) at 22° C. under a 14/10 light/dark cycle. Six seed and seed pod tissues of interest in this study were collected to create the following cDNA libraries: immature seeds, mature seeds, immature seed pods, mature seed pods, night-harvested seed pods, and Cresor variety (high erucic acid) seeds. Tissue samples were collected within specified time points for each developing tissue, and multiple samples within a time frame pooled together for eventual extraction of total RNA. Samples from immature seeds were taken between 1-25 days after anthesis (daa), mature seeds between 25-50 daa, immature seed pods between 1-15 daa, mature seed pods between 15-50 daa, night-harvested seed pods between 1-50 daa, and Cresor seeds 5-25 daa.

*Helianthus annuus*

Plants were grown in Metromix (Scotts, Marysville, Ohio) at 25° C. in the greenhouse with supplementary lighting under a 14/10 light/dark cycle. Developing seeds were carefully removed with tweezers from the sunflowers 6-8 days, 13-16 days and 24-26 days after flowering of the first flowers on the outermost rim of the sunflower.

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4M NaCl; 20 mM EDTA. N-Laurylsarcosine buffer:10% (w/v) N-laurylsarcosine; 100 mM Tris HCl pH 8.0; 20 mM EDTA.

The plant material was triturated under liquid nitrogen in a mortar to give a fine powder and transferred to 2 ml EPPENDORF vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two EPPENDORF vessels (2 ml) and extracted twice by shaking with the same volume of chloroform/isoamyl alcohol (24:1). For phase separation, centrifligation was carried out at 8000 g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H2O +RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and Poly-(A)+ RNA from Plants

*Arabidopsis thaliana*

For the investigation of transcripts, both total RNA and poly-(A)+ RNA were isolated. RNA was isolated from siliques of *Arabidopsis* plants according to the following procedure:

RNA Preparation from *Arabidopsis* Seeds—"hot" Extraction:

Buffers, Enzymes, and Solutions:
  2M KCl
  Proteinase K
  Phenol (for RNA)
  Chloroform:Isoamylalcohol
  (Phenol:choloroform 1:1; pH adjusted for RNA)
  4M LiCl, DEPC-treated
  DEPC-treated water
  3M NaOAc, pH 5, DEPC-treated
  Isopropanol
  70% ethanol (made up with DEPC-treated water)
  Resuspension buffer:0.5% SDS, 10 mM Tris pH 7.5, 1 mM EDTA made up with DEPC-treated water as this solution can not be DEPC-treated
  Extraction Buffer:
  0.2M Na Borate
  30 mM EDTA
  30 mM EGTA
  1% SDS (250 µl of 10% SDS-solution for 2.5 ml buffer)
  1% Deoxycholate (25 mg for 2,5 ml buffer)
  2% PVPP (insoluble—50 mg for 2.5 ml buffer)
  2% PVP 40K (50 mg for 2.5 ml buffer)
  10 mM DTT
  100 mM β-Mercaptoethanol (fresh, handle under fume hood—use 35 µl of 14.3M solution for 5 ml buffer)

Extraction

Extraction buffer was heated up to 80° C. Tissues were ground in liquid nitrogen-cooled mortar, and the tissue powder was transferred to a 1.5 ml tube. Tissues should be kept frozen until buffer is added; the sample should be transferred with a pre-cooled spatula; and the tube should be kept in liquid nitrogen at all times. Then 350 µl preheated extraction buffer was added (For 100 mg tissue, buffer volume can be as much as 500 µl for bigger samples) to tube; samples were vortexed; and the tube was heated to 80° C. for approximately 1 minute and then kept on ice. The samples were vortexed and ground additionally with electric mortar.

Digestion

Proteinase K (0.15 mg/100 mg tissue) was added, and the mixture was vortexed and then kept at 37° C. for one hour.

First Purification

For purification, 27 µl 2M KCl was added to the samples. The samples were chilled on ice for 10 minutes and then centrifuged at 12,000 rpm for 10 minutes at room temperature. The supernatant was transferred to a fresh, RNAase-free tube, and one phenol extraction was conducted, followed by a choloroform:isoamylalcohol extraction. One volume isopropanol to was added to the supernatant, and the mixture was chilled on ice for 10 minutes. RNA was pelleted by centrifugation (7000 rpm for 10 minutes at room temperature). Pellets were dissolved in 1 ml 4M LiCl solution by vortexing the mixture 10 to 15 minutes. RNA was pelleted by a 5 minute centrifugation.

Second Purification

The pellet was resuspended in 500 µl Resuspension buffer. Then 500 µl of phenol was added, and the mixture was vortexed. Then, 250 µl chloroform:isoamylalcohol was added; the mixture was vortexed and then centrifuged for 5 minutes. The supernatant was transferred to a fresh tube. The choloform:isoamylalcohol extraction was repeated until the interface was clear. The supernatant was transferred to a fresh tube and $\frac{1}{10}$ volume 3M NaOAc, pH 5 and 600 µl isopropanol were added. The mixture was kept at −20 for 20 minutes or longer. The RNA was pelleted by 10 minutes of centrifugation, and then the pellet was washed once with 70% ethanol. All remaining alcohol was removed before dissolving the pellet in 15 to 20 µl DEPC-treated water. The quantity and quality of the RNA was determined by measuring the absorbance of a 1:200 dilution at 260 nm and 280 nm. (40 µg RNA/ml=1 $OD_{260}$).

The mRNA was prepared from total RNA, using the Amersham Pharmacia Biotech mRNA purification kit, which utilizes oligo(dT)-cellulose columns.

Isolation of Poly-(A)+ RNA was isolated using Dyna Beads® (Dynal, Oslo, Norway) following the instructions of the manufacturer's protocol. After determination of the concentration of the RNA or of the poly(A)+ RNA, the RNA was precipitated by addition of $\frac{1}{10}$ volume of 3M sodium acetate pH 4.6 and 2 volumes of ethanol and stored at −70° C.

*Brassica napus*

Seeds were separated from pods to create homogeneous materials for seed and seed pod cDNA libraries. Tissues were ground into fine powder under liquid nitrogen using a mortar and pestle and transferred to a 50 ml tube. Tissue samples were stored at −80° C. until extractions could be performed. Total RNA was extracted from tissues using an RNEASY RNA extraction Maxi kit (Qiagen) according to the manufacturer's protocol, and mRNA was processed from total RNA using an OLIGOTIEX mRNA Purification System kit (Qiagen), also according to the manufacturer's protocol. The mRNA was sent to Hyseq Phamaceuticals Incorporated (Sunnyville, Calif.) for further processing of RNA from each tissue type into cDNA libraries and for use in their proprietary processes in which similar inserts in plasmids are clustered based on hybridization patterns.

*Helianthus annuus*

Seeds were ground into fine powder under liquid nitrogen using a mortar and pestle and transferred to a 50 ml tube. Tissue samples were stored at −80° C. until extractions could be performed. Total RNA was extracted from tissues using an RNEASY RNA extraction Maxi kit (Qiagen) according to the manufacturer's protocol, and mRNA was processed from total RNA using an OLIGOTEX mRNA Purification System kit (Qiagen), also according to the manufacturer's protocol. The mRNA was sent to Hyseq Pharmaceuticals Incorporated (Sunnyville, Calif.) for further processing of mRNA from each seed development stage into cDNA libraries and for use in their proprietary processes in which similar inserts in plasmids are clustered based on hybridization patterns.

Example 4 cDNA Library Construction

For cDNA library construction, first strand synthesis was achieved using Murine Leukemia Virus reverse transcriptase (Roche, Mamuheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and SEPLIADEX G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on ELUTIP-D columns (Schlcicher and Schuell, Dassel, Germany) and were ligated to vector arms and packed into lambda ZAPII phages or lambda ZAP-Express phages using the GIGAPACK Gold Kit (Stratagene, Amsterdam, Netherlands) using the material and following the instructions of the manufacturer.

*Brassica* and sunflower cDNA libraries were generated at Hyseq Pharmaceuticals Incorporated (Sunnyville, Calif.). No amplification steps were used in the library production to retain expression information. Hyseq's genomic approach involves grouping the genes into clusters and then sequencing representative members from each cluster. The cDNA libraries were generated from oligo dT column purified mRNA. Colonies from transformation of the cDNA library into *E. coli* were randomly picked and the cDNA inserts were amplified by PCR and spotted on nylon membranes. A set of $^{33}$P radiolabeled oligonucleotides were hybridized to the clones, and the resulting hybridization pattern determined to which cluster a particular clone belonged. The cDNA clones and their DNA sequences were obtained for use in overexpression in transgenic plants and in other molecular biology processes described herein.

Example 5

Identification of LMP Genes of Interest

*Arabidopsis thaliana*

To identify potential gene targets from *Arabidopsis*, the MEGASORT and MPSS technologies of Lynx Therapeutics Inc. were used. MEGASORT is a micro-bead technology that allows both the simultaneous collection of millions of clones on as many micro-beads (See Brenner et al., 1999, Proc. Nati. Acad. Sci. USA 97:1665-1670). Genes were identified based on their differential expression in different developmental stages of Arabidopsis seeds and siliques. RNA and mRNA were isolated from wild-type and mutant roots using standard procedures. The MEGASORT technology enabled the identification of over- and under-expressed clones in two mRNA samples without prior knowledge of the genes and was thus useful to discover differentially expressed genes that encode LMP proteins. The MPSS technology enabled the quantitation of the abundance of mRNA transcripts in the mRNA samples (see, e.g., Brenner et al., Nat. Biotechnol. 18:630-4) and was used to obtain expression profiles of different developmental seed stages.

*Brassica napus*

RNA expression profile data were obtained from the Hyseq clustering process. Clones showing 75% or greater expression in seed libraries compared to the other tissue libraries were selected as LMP candidate genes. The *Brassica napus* clones were selected based on their expression profile. Homologous sequences from *Arabidopsis* were identified using BLAST and FASTA searches and the corresponding LMPs (SEQ ID NO:47, SEQ ID NO:49, SEQ ID NO:51, SEQ ID NO:53, SEQ ID NO:55, SEQ ID NO:57, and SEQ ID NO:59) were isolated from *Arabidopsis* cDNA (See Examples 7 and 10 below).

*Helianthus annuus*

RNA expression profile data were obtained from the Hyseq clustering process. The *Helianthus annuus* clones were selected for overexpression in *Arabidopsis* based on their predicted motifs and domains following PFAM and BLOCKS analysis of the sequences.

Example 6

Identification of Proteins Associated with Oil Bodies and Microsomes in Developing *Arabidopsis* and Canola Seed Isolation of Oil Bodies and Microsomes from Developing Oil Seeds Buffers and Solutions:
1. Extraction Buffer
   150 mM Tris pH 7.5
   10 mM KCl
   1.5 mM EDTA
   0.1 mM MgCl$_2$
   15% w/v sucrose
2. Centrifugation Buffer
   50 mM Tris pH7.5
   10 mM KCl
   1.5 mM EDTA
   0.1 mM MgCl$_2$
   10% w/v sucrose
3. Gradient Buffers (10, 19, 38 or 52)
   50 mM Tris pH7.5
   10 mM KCl
   1.5 mM EDTA
   0.1 mM MgCl$_2$
   plus either of the following:
   10% w/v sucrose or
   19% w/v sucrose or
   38% w/v sucrose or
   52% w/v sucrose Totally green siliques of *Arabidopsis thaliana* or *Brassica napus* were opened on ice using razor blades and all developing seeds of bright green color removed carefully and placed in the pre-cooled extraction buffer. Only seeds of bright green color without brown or yellow spots, and solid consistency (in contrast to the youngest seeds) were used. The seeds were homogenized using a standard household homogenizer, razor blades, a chopping block and a glass homogenizer. The procedure was carried out on ice in the cold with frequent stops to prevent warming of the homogenate. For the smaller *Arabidopsis* seeds, a glass homogenizer was used immediately.

The homogenate was filtered through 2 layers of Miracloth (Calbiochem, Calif., USA) using precooled equipment. The filtered homogenate was then transferred into centrifuge tubes for an SW28 rotor, tarred, and centrifuged for 45 minutes at 8,000 rpm in a Beckman Ultrafuge (Beckman Coulter, Fullerton, Calif., USA) at 4° C. The pellet was discarded; all the liquid and the oil body layer from the top were homogenised again, transferred into new centrifuge tubes, and spun in the same ultracentrifuge for 1 hour at 4° C. and 25,000 rpm.

The resulting layer of lipid bodies was removed from the top, resuspended in centrifugation buffer, homogenized with a glass homogenizer and centrifuged again at 25,000 rpm for 1 hour at 4° C. This procedure was repeated until the oil bodies had a creamy white color. They were then removed and frozen until lipid extraction.

The pellet resulting from the first centrifugation at 25,000 rpm was kept, and resuspended in 4 ml gradient buffer containing 52% sucrose. The suspension was transferred to the bottom of a centrifuge tube for an SW28 rotor. A 10 ml gradient buffer containing 38% sucrose was carefully layered on the suspension and then topped by a layer of gradient buffer containing 19% sucrose, which was topped by a layer of gradient buffer containing 10% sucrose. An ultracentrifugation at 4° C. and 25,000 rpm was performed overnight. The centrifugation was stopped without a brake to avoid disturbances of the interfaces and layers. At the interface of the different layers, white to cream colored layers of microsomes and proteins were removed with a syringe, diluted with centrifugation buffer, and pelleted by centrifugation. The pellets were either used immediately or frozen until lipid extraction.

Lipid Extraction from Oil Bodies and Microsomes

Solutions:

100 mM Tris saturated Phenol (Aquaphenol) pH 8.0

100 mM Tris buffer pH 8.0

0.1M $NH_4$ Acetat in MeOH

Equal volumes of the Tris buffer pH 8 and the phenol (Tris saturated, pH 8) were mixed. Immediately before the lipid extraction, 5% (v/v) mercaptoethanol was added to the Tris-phenol mix. Per 100 mg of frozen or fresh sample (oil bodies or microsomes, 1 ml of mercaptoethanol-Tris-phenol was added to the sample, and the samples mixed well for 1 hour (stirrer, rotary shaker) at 4° C. An equal volume of Tris pH 8.0 buffer was added and mixed again for 30 minutes at 4° C. Then the mix was centrifuged at approximately 1,000 g at 4° C. for 15 minutes. The bottom layer (i.e. the Phenol layer) was transferred into a new 50 ml vessel without taking anything of the interface, using a syringe or pipette. Then 4 volumes of ammonium acetate in methanol was added, and the sample was precipitated by freezing at 20° C. overnight. After precipitation, the sample was centrifuged (4° C., approx 1,000 g, 30 minutes) and the pellet was kept. The pellet was washed two times with 20 ml ammonium acetate in methanol (centrifugation as before). For oil bodies, the resulting pellet was extracted with Tris-phenol-mercaptoethanol a second time; for microsomes, the pellet was directly washed 3 times with 10 ml methanol (centrifugation as before). The resulting pellet was stored with a little methanol at 4° C. until the determination of protein amount and 2D gel electrophoresis.

Determination of Protein Amount

The amount of protein was determined using the Protein Assay Kit (Sigma). According to the manufacturer's protocol, the protein samples were precipitated with TCA.

Isoelectric focussing (IEF)—1st Dimension

For the rehydration of the IEF-strips (e.g. IMMOBILINE DryStrip pH 4-7, 24 cm, from Amersham), freshly prepared buffer is used:

Rehydration buffer:

14.41 g(8M) urea 4.57 g (2M) Thiourea 92.52 mg (20 mM) Dithiothreitol (DTT)

300 mg (1 %) CHAPS detergent

156 µl Ampholine (Amersham) pH 3.5-10 fill up to 30 ml with ddH2O

Typically 400-1500 µg protein were used for a preparative 2D gel with Coomassie staining. The required amount of protein in solution was diluted with the rehydration buffer to a total volume of 600 µl and vortexed well. The solution was spread along the groove of the IMMOBILINE Dry Strip Reswelling Trays (Amersham). The protective cover of the IEF strip was removed, and the strip placed carefully into the tray with the gel side down, making sure that the strip had good contact with the sample solution and no air bubbles were trapped between the solution and the strip. When loading of the strips was complete, the chamber was sealed (to protect from evaporation) and left at ambient temperature for 24 hours.

After 24 hours, the strips were taken from the chamber, padded slightly dry with wet WHATMAN filter paper No. 3 and placed into the "IMMOBILINE strip tray" of the MULTIPHOR chamber (Pharmacia) with the gel side up. Then, 90 to 100 ml cover fluid (DryStrip Cover Fluid, Amersham) was added. Two electrode strips were being soaked with dH2O, and the surplus water was removed with a paper tissue. On the cathode as well as on the anode side of the strips, one of the electrode strips was placed across the gel strips. The electrode chamber was closed with the electrode in place, and the focusing was performed according to the procedure given in Table 5.

TABLE 5

| Parameter for the isoelectric focusing | | | | |
|---|---|---|---|---|
| voltage (V) | current (mA) | power (W) | pattern | Voltage hours (Vh) |
| 500 | 1 | 5 | Gradient | 500 |
| 500 | 1 | 5 | Gradient | 2500 |
| 3500 | 1 | 5 | Gradient | 10.000 |
| 3500 | 1 | 5 | Gradient | 45.000 |

At the end of the focusing, the current was interrupted, the chamber was opened, and the gel strips were padded slightly on wetted tissue to remove cover fluid. The gel strips could be used immediately, or if necessary, the gel strips could be stored at −80° C. until further use.

SDS-Polyaerylamide Gel Electrophoresis (PAGE)—2nd Dimension

Preparation of the ETTAN DALT-II electrophoresis Chamber

The eleetrophoresis chamber was first filled with 7.5 1 of dH2O. The control unit and the pump were switched on, and 75 ml of the concentrated anode buffer was added (ETTAN DALT II Buffer Kit, Amersham). The 2D gels (pre-cast ETTAN DALT II Gel (12.5%), Amersham) and 2 ml gel buffer were loaded into the gel frame; the surplus gel buffer was removed with a common wallpaper roller; and the frame was closed. Surplus buffer was removed by tilting the frame. The left and right side of the frame were sealed with agarose melted at 85° C. The bottom end of the frame was wetted with dH2O and the frame was inserted into the ETTAN DALT chamber. The cathode buffer (ETTAN DALT II Buffer Kit, Amersham), diluted 1:10, was used to fill the chamber up to the mark.

Equilibration of the Gel Strips

Equilibration Stock Buffer:
  36 g (6M) urea
  30 g (30%) glycerol
  2 g (2%) SDS
  3.3 ml Tris-HCl-buffer pH 8.8 (18.2 g (1.5M) Tris/HCl, 0.4 g (0.4%) SDS, pH 8.8 ad 100 ml with dH2O)
  ad 100 ml with dH2O DTT Equilibration Buffer (Per Gel Strip):
  4 ml Equilibration stock buffer
  20 µl Bromphenolblue solution (30 mg Bromphenoiblue in 10 ml Tris/HCl-buffer pH 8.8)
  200 µl DTT stock solution (200 mg DTT+1 ml dH2O)

Jodacetamicle Equilibration Buffer (Per Gel Strip):
  4 ml Equilibration stock buffer
  20 µl Bromphenoiblue solution
  192 mg (260 mM) Jodacetamid The gel strip was placed into the equilibration tray with the gel side up. First, 4 ml of the DTT equilibration buffer was added, and the tray was shaken for 15 minutes on a rotary shaker. The buffer was discarded, and the strip was shaken for 15 minutes with the Jodacetamide equilibration buffer. The buffer was again removed by decanting, and the surplus equilibration buffer was removed by patting the gel strips on wetted tissue.

Electrophoresis

The gel strips were orientated with the support side toward the glass slide of the gel, and inserted into the groove between the glass slide of the gel frame and the support of the gel. After moving the strip down and into contact with the gel, the strip was pressed slightly against the gel. If necessary, air bubbles were removed. The chamber was closed, and the electrophoretic run was performed according to the parameters given in table 6:

TABLE 6

Parameter for the SDS-PAGE in the ETTAN-Dalt-chamber

| step | pump | Power per gel (W) | Temp. (° C.) | time (min) | comments |
|---|---|---|---|---|---|
| 1 | Auto | 4 | 25 | 75 | const. Power |
| 2 | Auto | 14 | 25 | 360 | const. Power |

When the dye front reached the bottom end of the chamber, the current was broken and the chamber opened. The gels were removed from the gel frames and stored in the fixing solution (see staining of the gel) under constant shaking for a period of no less then 2 hours, usually overnight.

Coomassie Staining of the Gels

Per gel, 500 ml of the reagent solution was needed. The gels were shaken on a rotary shaker at 40 rpm. Table 7 summarizes the steps involved:

Staining Solution:
  20 ml (2%, v/v) phosphoric acid (85%)
  100 g (10%, w/v) Ammonium sulphate
  200 ml (20%, v/v) Methanol
  1 g (0.1%) SERVA Blue G, (Serva, Germany) add dH$_2$O to 1000 ml

TABLE 7

Coomassie-staining of the proteins after the 2D-PAGE

| Step | Solution | Incubation period |
|---|---|---|
| Fixation | 40% (v/v) Methanol<br>10% (v/v) acetic acid<br>50% (v/v) deionisedH$_2$O | >2 h |
| Washing | Deionized H$_2$O—H$_2$O | 20 minutes |
| Washing | Deionized H$_2$O—H$_2$O | 20 minutes |
| Washing | Deionized H$_2$O—H$_2$O | 20 minutes |
| Aequilibration | 2% (v/v) Phosphoric acid<br>10% (v/v) Methanol | 2 hours |
| staining | Satining solution (see below) | 12–24 hours |
| washing | Deionized H$_2$O—H$_2$O | 30 minutes |

Identification of Proteins Separated by 2D gel Electrophoresis.

Protein spots were excised from Coomassie blue-stained gels, washed with MeOH/H$_2$O and CAN, and digested with trypsin (Roche, Mannheim) overnight at 37° C. For nano-HPLC/MS/MS analysis, the peptides were separated using reverse phase chromatography (RP18-3, 100 Å, 15 cm, 75 µm i.d., from LC-Packings). Peptide analysis was performed on a LCQ ion trap mass spectrometer (ThermoFinnigan, San Jose). A mass spectrum in full-scan mode was followed by two MS/MS spectra of the most abundant peptide ions. Peptide tandem mass spectra were analysed using the MASCOT software package (Matrix Science, Ltd, London, UK), and peptides matched to publicly available databases of *Arabidopsis* proteins. Proteins identified in this manner were analyzed for domains possibly involved in regulation of metabolic processes. For selected proteins (SEQ ID NO:2, SEQ ID NO:4, SEQ ID NO:6, SEQ ID NO:8, SEQ ID NO:10, and SEQ ID NO:12), the full-length cDNA (SEQ ID NO:1, SEQ ID NO:3, SEQ ID NO:5, SEQ ID NO:7, SEQ ID NO:9, and SEQ ID NO:11) was cloned as described above.

Example 7

Cloning of Full-Length cDNAs and Orthologs of Identified LMP Genes

*Arabidopsis thaliana*

Full-length sequences of the *Arabidopsis thaliana* partial cDNAs (ESTs) that were identified from MECASORT and MPSS EST sequencing were isolated by RACE PCR using the SMART RACE cDNA amplification kit from Clontech allowing both 5' and 3' rapid amplification of cDNA ends (RACE). The isolation of cDNAs and the RACE PCR protocol used were based on the manufacturer's conditions. The RACE product fragments were extracted from agarose gels with a OIAQUICK Gel Extraction Kit (Qiagen) and ligated into the TOPO pCR 2.1 vector (Invitrogen) following manufacturer's instructions. Recombinant vectors were transformed into TOP10 cells (Invitrogen) using standard conditions (Sambrook et al., 1989). Transformed cells were grown overnight at 37° C. on LB agar containing 50 µg/ml kanamycin and spread with 40 µl of a 40 mg/ml stock solution of X-gal in dimethylformamide for blue-white selection. Single white colonies were selected and used to inoculate 3 ml of liquid LB containing 50 µg/ml kanamycin and grown overnight at 37° C. Plasmid DNA was extracted using the QIAPREP Spin Miniprep Kit (Qiagen) following manufacturer's instructions. Subsequent analyses of clones and restriction mapping was performed according to standard molecular biology techniques (Sambrook et al., 1989).

Gene sequences can be used to identify homologous or heterologous genes (orthologs, the same LMP gene from another plant) from cDNA or genomic libraries. This can be done by designing PCR primers to conserved sequences identified by multiple sequence alignments. Orthologs are often identified by designing degenerate primers to full-length or partial sequences of genes of interest. Homologous genes (e.g. full-length cDNA clones) can be isolated via nucleic acid hybridization using, for example, cDNA libraries: Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. Aqueous solution hybridization and washing is performed at an ionic strength of 1M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous genes that are related but not identical can be identified in a procedure analogous to the above-described procedure using low stringency hybridization and washing conditions. For aqueous hybridization, the ionic strength is normally kept at 1M NaCl while the temperature is progressively lowered from 68 to 42° C.

Isolation of gene sequences with homology (or sequence identity/similarity) only in a distinct domain (for example, 10-20 amino acids) can be carried out by using synthetic radiolabeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:
6×SSC
0.01M sodium phosphate
1 mM EDTA (pH 8)
0.5% SDS
100 μg/ml denaturated salmon sperm DNA
0.1% nonfat dried milk During hybridization, temperature is lowered stepwise to 5-10° C. below the estimated oligonucleotide $T_m$ or down to room temperature followed by washing steps and autoradiography. Washing is performed with low stringency such as three washing steps using 4×SSC. Further details are described by Sambrook et al. (1989, "Molecular Cloning: A Laboratory Manual", Cold Spring Harbor Laboratory Press) or Ausubel et al. (1994, "Current Protocols in Molecular Biology," John Wiley & Sons).

*Helianthus annuus*

Clones of *Heliandus annuus* genes obtained from Hyseq were sequenced at using a ABI 377 slab gel sequencer and BIGDYE Terminator Ready Reaction kits (PE Biosystems, Foster City, Calif.). The isolation of eDNAs and the RACE PCR protocol used were based on the manufacturer's conditions. The RACE product fragments were extracted from agarose gels with a QIAQUICK Gel Extraction Kit (Qiagen) and ligated into the TOPO pCR 2.1 vector (Invitrogen) following manufacturer's instructions. Recombinant vectors were transformed into TOP10 cells (Invitrogen) using standard conditions (Sambrook et al., 1989). Transformed cells were grown overnight at 37° C. on LB agar containing 50 μg/ml kanamycin and spread with 40 μl of a 40 mg/ml stock solution of X-gal in dimethylformamide for blue-white selection. Single white colonies were selected and used to inoculate 3 ml of liquid LB containing 50 μg/ml kanamycin and grown overnight at 37° C. Plasmid DNA was extracted using the QIAPREP Spin Miniprep Kit (Qiagen) following manufacturer's instructions. Subsequent analyses of clones and restriction mapping were performed according to standard molecular biology techniques (Sambrook et al., 1989).

RT-PCR and Cloning of *Arabidopsis thaliana* and *Helianthus annus* LMP Genes

Full-length LMP cDNAs were isolated by RT-PCR from *Arabidopsis thaliana* or *Helianthus annuus* RNA. The synthesis of the first strand cDNA was achieved using AMV Reverse Transcriptase (Roche, Mannheim, Germany). The resulting single-stranded cDNA was amplified via Polymerase Chain Reaction (PCR) utilizing two gene-specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C., and 1.5 minutes at 72° C. This was followed by thirty cycles of 40 seconds at 94° C., 40 seconds at 65° C., and 1.5 minutes at 72° C. The fragments generated under these RT-PCR conditions were analyzed by agarose gel electrophoresis to make sure that PCR products of the expected length had been obtained.

Full-length LMP cDNAs were isolated by using synthetic oligonucleotide primers (MWG-Biotech) designed based on the LMP gene specific DNA sequence that was determined by EST sequencing and by sequencing of RACE PCR products. The 5' PCR primers ("forward primer," F) SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:97, SEQ ID NO:99, SEQ ID NO:101, SEQ ID NO:103, SEQ ID NO:105, SEQ ID NO:107, SEQ ID NO:109, SEQ ID NO:11, SEQ ID NO:113, SEQ ID NO:115, SEQ ID NO:117, and SEQ ID NO:119 (for amplification of SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:1, SEQ ID NO:3, SEQ ID NO:5, SEQ ID NO:7, SEQ ID NO:9, SEQ ID NO:13, SEQ ID NO:15, SEQ ID NO:17, SEQ ID NO:19, SEQ ID NO:21 or SEQ ID NO:121, SEQ ID NO:47, SEQ ID NO:49, SEQ ID NO:51, SEQ ID NO:53, SEQ ID NO:55, SEQ ID NO:57, and SEQ ID NO:59, respectively) contained an NotI restriction site 5' upstream of the ATG start codon. The 5' PCR primer ("forward primer," F) SEQ ID NO:95 for amplification of SEQ ID NO:11 contained PstI and NotI restriction sites 5' upstream of the ATG start codon. The 3' PCR primers ("reverse primer," R) SEQ ID NO:62 and SEQ ID NO:92 (for amplification of SEQ ID NO:23 and SEQ ID NO:7, respectively) contained an EcoRV restriction site 3' downstream of the stop codon. The 3' PCR primer ("reverse primer," R) SEQ ID NO:64 for amplification of SEQ ID NO:25 contained a SmaI restriction site 3' downstream of the stop codon. The 3' PCR primers ("reverse primer," R) SEQ ID NO:66, SEQ ID NO:86, SEQ ID NO:88, SEQ ID NO:90, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, and SEQ ID NO:120 (for amplification of SEQ ID NO:27, SEQ ID NO:1, SEQ ID NO:3, SEQ ID NO:5, SEQ ID NO:9, SEQ ID NO:11, SEQ ID NO:13, SEQ ID NO:15, SEQ ID NO:17, SEQ ID NO:19, SEQ ID NO:21 or SEQ ID NO:121, SEQ ID NO:47, SEQ ID NO:49, SEQ ID NO:51, SEQ ID NO:53, SEQ ID NO:55, SEQ ID NO:57, and SEQ ID NO:59, respectively) contained a StuI restriction site 3' downstream of the stop codon. The 3' PCR primers ("reverse primer," R) SEQ ID NO:68, SEQ ID NO:70, SEQ ID NO:72, SEQ ID NO:74, SEQ ID NO:76, SEQ ID NO:78, SEQ ID NO:80, SEQ ID NO:82, and SEQ ID NO:84 (for amplification of SEQ ID NO:29, SEQ ID NO:31, SEQ ID NO:33, SEQ ID NO:35, SEQ ID NO:37, SEQ ID NO:39, SEQ ID NO:41, SEQ ID NO:43, and SEQ ID NO:45, respectively) contained a NotI restriction site 3' downstream of the stop codon.

The restriction sites were added so that the RT-PCR amplification products could be cloned into the restriction sites located in the multiple cloning site of the binary vector. The following "forward" (F) and "reverse" (R) primers were used to amplify the full-length *Arabidopsis thaliana* or *Helianthus annuus* cDNAs by RT-PCR using RNA from *Arabidopsis thaliana* or *Helianthus annuus* as original template:

```
For amplification of SEQ ID NO: 1:
Osw14F
(5'-GCGGCCGCCATGGCAACGGGGGCTGAGAACC-3')         (SEQ ID NO: 85)

Osw14R
(5'-AGGCCTTTACCGGCGACCACCAGCAGG-3')             (SEQ ID NO: 86)

For amplification of SEQ ID NO: 3:
Osw15F
(5'-GCGGCCGCCATGGCAACCATGGCTAGGTCG-3')          (SEQ ID NO: 87)

Osw15R
(5'-AGGCCTTCAGTTGTCGTGCAATGCTTTG-3')            (SEQ ID NO: 88)

For amplification of SEQ ID NO: 5:
Osw16F
(5'-GCGGCCGCCATGGCGCAACCCCTCGTGAAG-3')          (SEQ ID NO: 89)

Osw16R
(5'-AGGCCTTTAGCCGCTGGCAACAATCTC-3')             (SEQ ID NO: 90)

For amplification of SEQ ID NO: 7:
Osw17F
(5'-GCGGCCGCCATGCCGATTAGCCGGAGAGTTC-3')         (SEQ ID NO: 91)

Osw17R
(5'-GATATCTCATATGGAATCATAAACCG-3')              (SEQ ID NO: 92)

For amplification of SEQ ID NO: 9:
Osw18F
(5'-GCGGCCGCCATGCCCATTAATCAGAAAATTC-3')         (SEQ ID NO: 93)

Osw18R
(5'-AGGCCTTCATTTGCGATCAAGAACC-3')               (SEQ ID NO: 94)

For amplification of SEQ ID NO: 11:
Osw20F
(5'-CTGCAGGCGGCCGCCATGGAGTGTAGTTCAGTGAGTG-3')   (SEQ ID NO: 95)

Osw20R
(5'-AGGCCTCTAGTATTGGACTAACGATAAC-3')            (SEQ ID NO: 96)

For amplification of SEQ ID NO: 13:
Osw21F
(5'-GCGGCCGCATGGTTGAAACCTTGTTTGAAG-3')          (SEQ ID NO: 97)

Osw21R
(5'-AGGCCTCTAGGCCTTATCCACCTTCC-3')              (SEQ ID NO: 98)

For amplification of SEQ ID NO: 15:
Osw22F
(5'-GCGGCCGCATGGGCAAAAAAGACATGCCTA-3')          (SEQ ID NO: 99)

Osw22R
(5'-AGGCCTTCATATJTGTCGTGTAACGAGGG-3')           (SEQ ID NO: 100)

For amplification of SEQ ID NO: 17:
Osw23F
(5'-GGGGCCGCATGATATTATCGTTTCGTGGAC-3')          (SEQ ID NO: 101)

Osw23R
(5'-AGGCCTCTATACAGATTTGCCATCGGTG-3')            (SEQ ID NO: 102)
```

-continued

For amplification of SEQ ID NO: 19:
Osw24F
(5'-GCGGCCGCATGAACCGGATGATCGAAGCG-3')         (SEQ ID NO: 103)

Osw24R
(5'-AGGCCTTCATATTTGGTGCACCTCGGC-3')           (SEQ ID NO: 104)

For amplification of
SEQ ID NO: 21 or SEQ ID NO: 121:
Osw26F
(5'-GCGGCCGCATGCAGACCGTTTCTCGGAG-3')          (SEQ ID NO: 105)

Osw26R
(5'-AGGCCTTCAAGGATAAGACTCTGGAG-3')            (SEQ ID NO: 106)

For amplification of SEQ ID NO: 23:
JB69F
(5'-GCGGCCGCCATGAAGATATACTCTAGAACG-3')        (SEQ ID NO: 61)

JB69R
(5'-GATATCTTAGGCTGCCTCTGCAAACCC-3')           (SEQ ID NO: 62)

For amplification of SEQ ID NO: 25:
JB70F
(5'-GCGGCCGCCATGGGAGTATACTCGAGAGCG-3')        (SEQ ID NO: 63)

JB70R
(5'-CCCGGGTCACACGGCTTCTGCGAAGCC-3')           (SEQ ID NO: 64)

For amplification of SEQ ID NO: 27:
JB71F
(5'-GCGGCCGCCATGGGAACTAGGTTCCAATCA-3')        (SEQ ID NO: 65)

JB71R
(5'-AGGCCTTTAAGCAGCTTTGGCGAATCC-3')           (SEQ ID NO: 66)

For amplification of SEQ ID NO: 29:
JB80F
(5'-GAGCGGCCGCCATGGAGAAAGGTTTGACGAT-3')       (SEQ ID NO: 67)

JB80R
(5'-GAGCGGCCGCCTTAAGGATGCAAGGGCTCCT-3')       (SEQ ID NO: 68)

For amplification of SEQ ID NO: 31:
JB82F
(5'-GAGCGGCCGCCATGCATTGGCATGGTGTAGAGCAG-3')   (SEQ ID NO: 69)

JB82R
(5'-GAGCGGCCGCCTTATTCATAGCAAGGCGGCA-3')       (SEQ ID NO: 70)

For amplification of SEQ ID NO: 33:
JB84F
(5'-GAGCGGCCGCCATGTCTGCTTCTGATTCCTCT-3')      (SEQ ID NO: 71)

JB84R
(5'-GAGCGGCCGCCTTAGTCGCGGAACTCGTCCA-3')       (SEQ ID NO: 72)

For amplification of SEQ ID NO: 35:
JB85F
(5'-GAGCGGCCGCCATGGCGTTCCCTAAGGTATACTT-3')    (SEQ ID NO: 73)

JB85R
(5'-GAGCGGCCGCCCTAAGAGAGCTGACCACAAT-3')       (SEQ ID NO: 74)

For amplification of SEQ ID NO: 37:
JB88F
(5'-GAGCGGCCGCCATGGGTAGTGCAAAATCAGC-3')       (SEQ ID NO: 75)

JB88R
(5'-GAGCGGCCGCCTTAGGCGATGGAGCTTTTAT-3')       (SEQ ID NO: 76)

For amplification of SEQ ID NO: 39:
JB89F
(5'-GAGCGGCCGCCATGACTAATCCCATGATCAT-3')       (SEQ ID NO: 77)

JB89R
(5'-GAGCGGCCGCCCTAGAGACGGTGGATCAACG-3')       (SEQ ID NO: 78)

For amplification of SEQ ID NO: 41:
JB90F

-continued
(5'-GAGCGGCCGCCATGGTTTCTTCTTCTTTAAC-3')        (SEQ ID NO: 79)

JB90R
(5'-GAGCGGCCGCCTTAATAATTGGTAGCTTTAT-3')        (SEQ ID NO: 80)

For amplification of SEQ ID NO: 43:
JB91F
(5'-GAGCGGCCGCCATGGCCGGAGTTTTCAAAAC-3')        (SEQ ID NO: 81)

JB91R
(5'-GAGCGGCCGCCTCAAAAGAGAGCAACAACAG-3')        (SEQ ID NO: 82)

For amplification of SEQ ID NO: 45:
JB93F
(5'-GAGCGGCCGCCATGGCGTCAAAGCAACTGAG-3')        (SEQ ID NO: 83)

JB93R
(5'-GAGCGGCCGCCTCACTTGTTGGTGAACTTTG-3')        (SEQ ID NO: 84)

For amplification of SEQ ID NO: 47:
ToZ01F
(5'-GCGGCCGCATGGCTTCGGTTACTTTCTCT-3')          (SEQ ID NO: 107)

ToZ01R
(5'-AGGCCTTCACTTCCAGTTGTTGGCAA-3')             (SEQ ID NO: 108)

For amplification of SEQ ID NO: 49:
ToZ02F
(5'-GCGGCCGCATGGCAAAAGAAAATGGATT-3')           (SEQ ID NO: 109)

ToZ02R
(5'-AGGCCTTTAGATAGAGAGGTCAGCGA-3')             (SEQ ID NO: 110)

For amplification of SEQ ID NO: 51:
ToZ03F
(5'-GCGGCCGCATGGCGGCGAAAATTCCCGG-3')           (SEQ ID NO: 111)

ToZ03R
(5'-AGGCCTTCAAGACATGAACAGAGCCT-3')             (SEQ ID NO: 112)

For amplification of SEQ ID NO: 53:
ToZ04F
(5'-GCGGCCGCATGGGTTACATAGGAGCTCAT-3')          (SEQ ID NO: 113)

ToZ04R
(5'-AGGCCTTCAAGCTTCTTTACGCGTGA-3')             (SEQ ID NO: 114)

For amplification of SEQ ID NO: 55:
ToZ05F
(5'-GCGGCCGCATGTCTCCTTCTCACTCCATCA-3')         (SEQ ID NO: 115)

ToZ05R
(5'-AGGCCTTCATTTGGTGTTTGAAATAT-3')             (SEQ ID NO: 116)

For amplification of SEQ ID NO: 57:
ToZ11F
(5'-GCGGCCGCATGGCATCTGTTTACTCCACCCTA-3')       (SEQ ID NO: 117)

ToZ11R
(5'-AGGCCTTTAATCGTTTTTCTTGGAAA-3')             (SEQ ID NO: 118)

For amplification of SEQ ID NO: 59:
ToZ12F
(5'-GCGGCCGCATGGCATCAATTTACTCCTCTTT-3')        (SEQ ID NO: 119)

ToZ12R
(5'-AGGCCTCTAATCGCTTTTTTTGCCAT-3')             (SEQ ID NO: 120)

Example 8

Identification of Genes of Interest by Screening Expression Libraries with Antibodies The cDNA clones can be used to produce recombinant protein, for example, in *E. coli* (e.g. Qiagen OIAEXPRESS pQE system). Recombinant proteins are then nonnally affinity purified via Ni-NTA affinity chromatography (Qiagen). Recombinant proteins can be used to produce specific antibodies, for example, by using standard techniques for rabbit immunization. Antibodies are affinity purified using a Ni-NTA column saturated with the recombinant antigen as described by Gu et al. (1994, BioTechniques 17:257-262). The antibody can then be used to screen expression cDNA libraries to identify homologous or heterologous genes via an immunological screening (Sambrook et al., 1989, Molecular Cloning: A Laboratory Manual", Cold Spring Harbor Laboratory Press; or Ausubel et al. 1994, "Current Protocols in Molecular Biology", John Wiley & Sons).

Example 9

Northern-Hybridization

For RNA hybridization, 20 μg of total RNA or 1 μg of poly-(A)+ RNA was separated by gel electrophoresis in 1.25% strength agarose gels using formaldehyde as described in Amasino (1986, Anal. Biochem. 152:304), transferred by capillary attraction using 10×SSC to positively charged nylon membranes (HYBOND N+, Amersham, Braunschweig), immobilized by UV light, and pre-hybridized for 3 hours at 68° C. using hybridization buffer (10% dextran sulfate w/v, 1M NaCl, 1% SDS, 100 μg/ml of herring sperm DNA). The labeling of the DNA probe with the Highprime DNA labeling kit (Roche, Mannheim, Germany) was carried out during the pre-hybridization using $\alpha$-$^{32}$P dCTP (Amersham, Braunschweig, Germany). Hybridization was carried out after addition of the labeled DNA probe in the same buffer at 68° C. overnight. The washing steps were carried out twice for 15 minutes using 2×SSC and twice for 30 minutes using 1×SSC, 1% SDS at 68° C. The exposure of the sealed filters was carried out at −70° C. for a period of 1 day to 14 days.

Example 10

Computational Functional Analysis

Sequences were processed using the software packages GENOMAX and VECTOR NTI both commercially provided by Informax, Frederick, Maryland, USA) and annotated using the software packages GENOMAX and PEDANT-PRO commercially provided by Bio-Max (Munich, Germany). The programs incorporate practically all bioinformatics methods important for functional and structural characterization of protein sequences. For reference, see http://www.informaxinc.com/ and hip://pedant.mips.biochem.mpg.de.

The most important algorithms incorporated in GENOMAX and P PEDANT-PRO are: FASTA: Very sensitive protein sequence database searches with estimates of statistical significance (Pearson W. R., 1990, Rapid and sensitive sequence comparison with FASTP and FASTA. Methods Enzymol. 183:63-98); BLAST: Very sensitive protein sequence database searches with estimates of statistical significance (Altschul S.F. et al., Basic local alignment search tool. J. MoL Biol, 215:403-410); PREDATOR: High-accuracy secondary structure prediction from single and multiple sequences (Frishman & Argos 1997, 75% accuracy in protein secondary structure prediction. Proteins 27:329-335); CLUSTALW: Multiple sequence alignment (Thompson, J. D. et al., 1994, CLUSTAL W: improving the sensitivity of progressive multiple sequence alignment through sequence weighting, positions-specific gap penalties and weight matrix choice, Nucleic Acids Res. 22:4673-4680); TMAP: Transmembrane region prediction from multiply aligned sequences (Persson B. & Argos P. 1994, Prediction of transmembrane segments in proteins utilizing multiple sequence alignments, J. Mol. Biol. 237:1 82-192); ALOM2: Transmembrane region prediction from single sequences (Klein P., Kanehisa M., and DeLisi C. 1984, Prediction of protein function from sequence properties: A discriminant analysis of a database. Biochim. Biophys. Acta 787:221-226. Version 2 by Dr. K. Nakai); PROSEARCH: Detection of PROSITE protein sequence patterns (Kolakowski L. F. Jr. et al., 1992, ProSearch: fast searching of protein sequences with regular expression patterns related to protein structure and function. Biotechniques 13:919-921); BLIMPS: Similarity searches against a database of ungapped blocks (Wallace & Henikoff 1992, PATMAT: A searching and extraction program for sequence, pattern and block queries and databases, CABIOS 8:249-254. Written by Bill Alford); PFAM and BLOCKS searches of protein motifs and domains.

Example 11

Plasmids for Plant Transformation

For plant transformation, various binary vectors such as a pSUN2 and pSUN300 plant binary vector were used. Construction of the plant binary vectors was performed by ligation of the cDNA in sense or antisense orientation into the vector. In such vectors, a plant promoter was located 5' to the cDNA, where it activated transcription of the cDNA; and a polyadenylation sequence was located 3' to the cDNA. Various plant promoters were used, such as a constitutive promoter (Superpromoter), a seed-specific promoter, and a root-specific promoter. Tissue-specific expression was achieved by using a tissue-specific promoter. For example, in some instances, seed-specific expression was achieved by cloning the napin or LeB4 or USP promoter 5-prime to the cDNA. Also, any other seed specific promoter element can be used, and such promoters are well known to one of ordinary skill in the art. For constitutive expression within the whole plant, in some instances, the Superpromoter or the CaMV 35S promoter was used. The expressed protein also can be targeted to a cellular compartment using a signal peptide, for example for plastids, mitochondria, or endoplasmic reticulum (Kermode, 1996, Crit. Rev. Plant Sci. 15:285-423). The signal peptide is cloned 5' in frame to the cDNA to achieve subcellular localization of the fusion protein.

The plant binary vectors comprised a selectable marker gene driven under the control of one of various plant promoters, such as the AtAct2-I promoter and the Nos-promoter; the LMP candidate eDNA under the control of a root-specific promoter, a seed-specific promoter, a non-tissue specific promoter, or a constitutive promoter; and a terminator. Partial or full-length LMP cDNA was cloned into the plant binary vector in sense or antisense orientation behind the desired promoter. The recombinant vector containing the gene of interest was transformed into Top10 cells (Invitrogen) using standard conditions. Transformed cells were selected for on LB agar containing the selective agent, and cells were grown overnight at 37° C. Plasmid DNA was extracted using the QIAPREP Spin Miniprep Kit (Qiagen) following manufacturer's instructions. Analysis of subsequent clones and restriction mapping was performed according to standard molecular biology techniques (Sambrook et al., 1989, Molecular Cloning, A Laboratory Manual. $2^{nd}$ Edition. Cold Spring Harbor Laboratory Press. Cold Spring Harbor, N.Y.).

Example 12

*Agrobacterium* Mediated Plant Transformation

*Agrobacterium* mediated plant transformation with the LMP nucleic acids described herein can be performed using standard transformation and regeneration techniques (Gelvin, Stanton B. & Schilperoort R. A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993). For example, Agrobacterium mediated transformation can be performed using the GV3 (pMP90) (Koncz & Schell, 1986, Mol. Gen. Genet. 204:383-396) or LBA4404 (Clontech) Agrobacterium tumefaciens strain.

Arabidopsis thaliana can be grown and transformed according to standard conditions (Bechtold, 1993, Acad. Sci. Paris. 316:1194-1199; Bent et al., 1994, Science 265:1856-1860). Additionally, rapeseed can be transformed with the LMP nucleic acids of the present invention via cotyledon or hypocotyl transformation (Moloney et al., 1989, Plant Cell Report 8:238-242; De Block et al., 1989, Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Additionally, Agrobacterium mediated gene transfer to flax can be performed using, for example, a technique described by Mlynarova et al. (1994, Plant Cell Report 13:282-285).

Transformation of soybean can be performed using, for example, a technique described in EP 0424 047, U.S. Pat. No. 5,322,783 (Pioneer Hi-Bred International) or in EP 0397 687, U.S. Pat. No. 5,376,543 or 5,169,770 (University Toledo). Soybean seeds are surface sterilized with 70% ethanol for 4 minutes at room temperature with continuous shaking, followed by 20% (v/v) Clorox supplemented with 0.05% (v/v) Tween for 20 minutes with continuous shaking. Then the seeds are rinsed four times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

This method of plant transformation is also applicable to Brassica and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

Agrobacterium tumefaciens culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige & Skoog, 1962, Physiol. Plant. 15:473-497) medium supplemented with 100 mM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced Agrobacterium suspension culture. (The imbibition of dry embryos with a culture of Agrobacterium is also applicable to maize embryo axes).

The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 µmol m$^{-2}$s$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol m$^{-2}$s$^{-1}$ light intensity and 12 hour photoperiod for about 80 days.

Samples of the primary transgenic plants ($T_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR as recommended by the manufacturer.

Example 13

In Vivo Mutagenesis

In vivo mutagenesis of microorganisms can be performed by incorporation and passage of the plasmid (or other vector) DNA through E. coli or other microorganisms (e.g. Bacillus spp. or yeasts such as Saccharomyces cerevisiae) which are impaired in their capabilities to maintain the integrity of their genetic information. Typical mutator strains have mutations in the genes for the DNA repair system (e.g., mutHLS, mutD, mutT, etc.; for reference, see Rupp W. D. 1996, DNA repair mechanisms, in: Escherichia coli and Salmonella, p. 2277-2294, ASM: Washington.). Such strains are well known to those skilled in the art. The use of such strains is illustrated, for example, in Greener and Callahan, 1994, Strategies 7:32-34. Transfer of mutated DNA molecules into plants is preferably done after selection and testing in microorganisms. Transgenic plants are generated according to various examples throughout this document.

Example 14

Assessment of the mRNA Expression and Activity of a Recombinant Gene Product in the Transformed Organism The activity of a recombinant gene product in the transformed host organism can be measured on the transcriptional level or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (See, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al., 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 15

In Vitro Analysis of the Function of *Arabidopsis thaliana*, *Brassica napus*, and *Helianthus annuus* Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M. & Webb, E. C., 1979, Enzymes. Longmans: London; Fersht, 1985, Enzyme Structure and Mechanism. Freeman: New York; Walsh, 1979, Enzymatic Reaction Mechanisms. Freeman:San Francisco; Price, N.C., Stevens, L., 1982, Fundamentals of Enzymology. Oxford Univ. Press: Oxford; Boyer, P. D., ed. (1983) The Enzymes, 3rd ed. Academic Press: New York; Bisswanger, H., 1994, Enzymkinetik, 2nd ed. VCH:Weinheim (ISBN 3527300325); Bergmeyer, H. U., Bergmeyer, J., Graβl, M., eds. (1983-1986) Methods of Enzymatic Analysis, 3rd ed., vol. I-XII, Verlag Chemie: Weinheim; and Ullmann's Encyclopedia of Industrial Chemistry (1987) vol. A9, Enzymes. VCH:Weinheim, p. 352-363.

Example 16

Analysis of the Impact of Recombinant LMPs on the Production of a Desired Seed Storage Compound: Fatty Acid Production The total fatty acid content of *Arabidopsis* seeds was determined by conventional gas-liquid chromatography (GLC) analyses after conversion to methyl esters (Schulte & Weber, 1989, Fat Sci. Technol. 91:181). For this, total fatty acids were extracted with methyl tertiary-butyl ether (MTBE) and derivatized to their corresponding fatty acid methyl esters (FAMEs) with trimethylsulfonium hydroxide (TMSH). The separation of the FAMEs was performed on a capillary column (DB Wax 10 m×0.1 mm×0.2 µm) in an Agilent Technology 6890N Network GC System equipped with a flame ionisation detector (FID) using hydrogen as carrier gas. Determination of the fatty acid content was performed by adding an internal standard of known concentration. The total fatty acid contents of seeds of transgenic plants and plants containing the pBPS empty vector construct (without an LMP gene of interest) were measured. Bulked seeds (usually 5 mg seed weight) of a single plant were used; all extractions were performed in duplicate or triplicate. The controls indicated in the tables below have been grown side by side with the transgenic lines. Differences in the total values of the controls are explained either by differences in the growth conditions, which were found to be very sensitive to small variations in the plant cultivation, or by differences in the standards added to quantify the fatty acid content. Because of the seed bulking, all values obtained with T2 seeds, and in part also with T3 seeds, are the result of a mixture of homozygous (for the gene of interest) and heterozygous events, implying that these data underestimate the LMP gene effect.

TABLE 8

Determination of the T2 seeds of total fatty acid content of transgenic lines of OSW14 (containing SEQ ID NO: 1). Shown are the means (± standard deviation) of 4 individual control plants and 6 individual plants per line.

| Genotype | g total fatty acids/g seed weight |
| --- | --- |
| Col-0 empty vector control | 0.253 ± 0.009 |
| OSW14 transgenic seeds | 0.270 ± 0.006 |

TABLE 9

Determination of the T2 seeds of total fatty acid content of transgenic lines of OSW15 (containing SEQ ID NO: 3). Shown are the means (± standard deviation) of 3 individual control plants and 18 individual plants per line

| Genotype | g total fatty acids/g seed weight |
| --- | --- |
| Col-0 empty vector control | 0.259 ± 0.008 |
| OSW15 transgenic seeds | 0.300 ± 0.010 |

TABLE 10

Determination of the T2 seeds of total fatty acid content of transgenic lines of OSW16 (containing SEQ ID NO: 5). Shown are the means (± standard deviation) of 3 individual control plants and 10 individual plants per line

| Genotype | g total fatty acids/g seed weight |
|---|---|
| Col-0 empty vector control | 0.296 ± 0.024 |
| OSW16 transgenic seeds | 0.318 ± 0.002 |

TABLE 11

Determination of the T2 seeds of total fatty acid content of transgenic lines of OSW17 (containing SEQ ID NO: 7). Shown are the means (± standard deviation) of 3 individual control plants and 5 individual plants per line

| Genotype | g total fatty acids/g seed weight |
|---|---|
| Col-0 empty vector control | 0.292 ± 0.008 |
| OSW17 transgenic seeds | 0.315 ± 0.004 |

TABLE 12

Determination of the T2 seeds of total fatty acid content of transgenic lines of OSW18 (containing SEQ ID NO: 9). Shown are the means (± standard deviation) of 3 individual control plants and 14 individual plants per line

| Genotype | g total fatty acids/g seed weight |
|---|---|
| Col-0 empty vector control | 0.282 ± 0.002 |
| OSW18 transgenic seeds | 0.309 ± 0.007 |

TABLE 13

Determination of the T2 seeds of total fatty acid content of transgenic lines of OSW21 (containing SEQ ID NO: 13). Shown are the means (± standard deviation) of 4 individual control plants and 22 individual plants per line

| Genotype | g total fatty acids/g seed weight |
|---|---|
| Col-0 empty vector control | 0.242 ± 0.025 |
| OSW21 transgenic seeds | 0.283 ± 0.016 |

TABLE 14

Determination of the T2 seeds of total fatty acid content of transgenic lines of Jb069 (containing SEQ ID NO: 23). Shown are the means (± standard deviation) of 4 individual control plants and 8 individual plants per line

| Genotype | g total fatty acids/g seed weight |
|---|---|
| Col-0 empty vector control | 0.193 ± 0.016 |
| JB069 transgenic sedes | 0.211 ± 0.005 |

TABLE 15

Determination of the T2 seeds of total fatty acid content of transgenic lines of Jb070 (containing SEQ ID NO: 25). Shown are the means (± standard deviation) of 4 individual control plants and 7 individual plants per line

| Genotype | g total fatty acids/g seed weight |
|---|---|
| Col-0 empty vector control | 0.193 ± 0.016 |
| JB070 transgenic sedes | 0.218 ± 0.003 |

TABLE 16

Determination of the T2 seeds of total fatty acid content of transgenic lines of Jb071 (containing SEQ ID NO: 27). Shown are the means (± standard deviation) of 4 individual control plants and 13 individual plants per line

| Genotype | g total fatty acids/g seed weight |
|---|---|
| Col-0 empty vector control | 0.246 ± 0.009 |
| JB071 transgenic sedes | 0.278 ± 0.007 |

TABLE 17

Determination of the T2 seeds of total fatty acid content of transgenic lines of Jb080 (containing SEQ ID NO: 29). Shown are the means (± standard deviation) of 4 individual control plants and 19 individual plants per line

| Genotype | g total fatty acids/g seed weight |
|---|---|
| Col-0 empty vector control | 0.240 ± 0.017 |
| JB080 transgenic sedes | 0.268 ± 0.006 |

TABLE 18

Determination of the T2 seeds of total fatty acid content of transgenic lines of Jb082 (containing SEQ ID NO: 31). Shown are the means (± standard deviation) of 4 individual control plants and 8 individual plants per line

| Genotype | g total fatty acids/g seed weight |
|---|---|
| Col-0 empty vector control | 0.240 ± 0.014 |
| JB082 transgenic seeds | 0.264 ± 0.007 |

TABLE 19

Determination of the T2 seeds of total fatty acid content of transgenic lines of Jb084 (containing SEQ ID NO: 33). Shown are the means (± standard deviation) of 3 individual control plants and 8 individual plants per line

| Genotype | g total fatty acids/g seed weight |
|---|---|
| Col-0 empty vector control | 0.379 ± 0.025 |
| JB084 transgenic seeds | 0.426 ± 0.004 |

TABLE 20

Determination of the T2 seeds of total fatty acid content of transgenic lines of Jb085 (containing SEQ ID NO: 35). Shown are the means (± standard deviation) of 4 individual control plants and 8 individual plants per line

| Genotype | g total fatty acids/g seed weight |
|---|---|
| Col-0 empty vector control | 0.231 ± 0.004 |
| JB085 transgenic seeds | 0.263 ± 0.009 |

TABLE 21

Determination of the T2 seeds of total fatty acid content of transgenic lines of Jb088 (containing SEQ ID NO: 37). Shown are the means (± standard deviation) of 4 individual control plants and 7 individual plants per line

| Genotype | g total fatty acids/g seed weight |
|---|---|
| Col-0 empty vector control | 0.353 ± 0.024 |
| JB088 transgenic seeds | 0.392 ± 0.016 |

TABLE 22

Determination of the T2 seeds of total fatty acid content of transgenic lines of Jb089 (containing SEQ ID NO: 39). Shown are the means (± standard deviation) of 4 individual control plants and 4 individual plants per line

| Genotype | g total fatty acids/g seed weight |
|---|---|
| Col-0 empty vector control | 0.314 ± 0.007 |
| JB089 transgenic seeds | 0.332 ± 0.006 |

TABLE 23

Determination of the T2 seeds of total fatty acid content of transgenic lines of Jb090 (containing SEQ ID NO: 41). Shown are the means (± standard deviation) of 4 individual control plants and 4 individual plants per line

| Genotype | g total fatty acids/g seed weight |
|---|---|
| Col-0 empty vector control | 0.321 ± 0.011 |
| JB090 transgenic seeds | 0.271 ± 0.020 |

TABLE 24

Determination of the T2 seeds of total fatty acid content of transgenic lines of Jb091 (containing SEQ ID NO: 43). Shown are the means (± standard deviation) of 4 individual control plants and 4 individual plants per line

| Genotype | g total fatty acids/g seed weight |
|---|---|
| Col-0 empty vector control | 0.279 ± 0.015 |
| JB091 transgenic seeds | 0.307 ± 0.004 |

TABLE 25

Determination of the T2 seeds of total fatty acid content of transgenic lines of Jb093 (containing SEQ ID NO: 45). Shown are the means (± standard deviation) of 4 individual control plants and 12 individual plants per line

| Genotype | g total fatty acids/g seed weight |
|---|---|
| Col-0 empty vector control | 0.353 ± 0.024 |
| JB093 transgenic seeds | 0.258 ± 0.024 |

TABLE 26

Determination of the T2 seeds of total fatty acid content of transgenic lines of OSW22 (containing SEQ ID NO: 15). Shown are the means (± standard deviation) of 4 individual control plants and 5 individual plants per line

| Genotype | g total fatty acids/g seed weight |
|---|---|
| Col-0 empty vector control | 0.272 ± 0.025 |
| OSW22 transgenic seeds | 0.291 ± 0.006 |

TABLE 27

Determination of the T2 seeds of total fatty acid content of transgenic lines of OSW23 (containing SEQ ID NO: 17). Shown are the means (± standard deviation) of 4 individual control plants and 3 individual plants per line

| Genotype | g total fatty acids/g seed weight |
|---|---|
| Col-0 empty vector control | 0.285 ± 0.022 |
| OSW23 transgenic seeds | 0.317 ± 0.008 |

TABLE 28

Determination of the T2 seeds of total fatty acid content of transgenic lines of OSW24 (containing SEQ ID NO: 19). Shown are the means (± standard deviation) of 4 individual control plants and 6 individual plants per line

| Genotype | g total fatty acids/g seed weight |
|---|---|
| Col-0 empty vector control | 0.267 ± 0.029 |
| OSW24 transgenic seeds | 0.307 ± 0.009 |

TABLE 29

Determination of the T2 seeds of total fatty acid content of transgenic lines of OSW26 (containing SEQ ID NO: 21). Shown are the means (± standard deviation) of 4 individual control plants and 5 individual plants per line

| Genotype | g total fatty acids/g seed weight |
|---|---|
| Col-0 empty vector control | 0.259 ± 0.012 |
| OSW26 transgenic seeds | 0.287 ± 0.014 |

TABLE 30

Determination of the T2 seeds of total fatty acid content of transgenic lines of ToZ01 (containing SEQ ID NO: 47). Shown are the means (± standard deviation) of 4 individual control plants and 7 individual plants per line

| Genotype | g total fatty acids/g seed weight |
|---|---|
| Col-0 empty vector control | 0.280 ± 0.011 |
| ToZ01 transgenic seeds | 0.298 ± 0.003 |

TABLE 31

Determination of the T2 seeds of total fatty acid content of transgenic lines of ToZ02 (containing SEQ ID NO: 49). Shown are the means (± standard deviation) of 4 individual control plants and 7 individual plants per line

| Genotype | g total fatty acids/g seed weight |
|---|---|
| Col-0 empty vector control | 0.247 ± 0.011 |
| ToZ02 transgenic seeds | 0.278 ± 0.019 |

TABLE 32

Determination of the T2 seeds of total fatty acid content of transgenic lines of ToZ03 (containing SEQ ID NO: 51). Shown are the means (± standard deviation) of 4 individual control plants and 2 individual plants per line

| Genotype | g total fatty acids/g seed weight |
|---|---|
| Col-0 empty vector control | 0.276 ± 0.011 |
| ToZ03 transgenic seeds | 0.312 ± 0.027 |

TABLE 33

Determination of the T2 seeds of total fatty acid content of transgenic lines of osw20 suppression (containing SEQ ID NO: X). Shown are the means (± standard deviation) of 4 individual control plants and 14 individual plants per line

| Genotype | g total fatty acids/g seed weight |
|---|---|
| Col-0 empty vector control | 0.338 ± 0.022 |
| Osw20 suppression transgenic seeds | 0.379 ± 0.012 |

Example 17

Analysis of the Impact of Recombinant Proteins on the Production of a Desired Seed Storage Compound The effect of the genetic modification in plants on a desired seed storage compound (such as a sugar, lipid, or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (See, for example, Ullman, 1985, Encyclopedia of Industrial Chemistry, vol. A2, pp. 89-90 and 443-613, VCH: Weinheim; Fallon, A. et al., 1987, Applications of HPLC in Biochemistry in: Laboratory Techniques in Biochemistry and Molecular Biology, vol. 17; Rehm et al., 1993, Product recovery and purification, Biotechnology, vol. 3, Chapter III, pp. 469-714, VCH: Weinheim; Belter, P. A. et al., 1988, Bioseparations: downstream processing for biotechnology, John Wiley & Sons; Kennedy J. F. & Cabral J. M. S., 1992, Recovery processes for biological materials, John Wiley and Sons; Shaeiwitz J. A. & Henry J. D., 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland:Oily Press, 1989 Repr. 1992.—IX,307 S.—Oily Press Lipid Library; and Progress in Lipid Research, Oxford: Pergamon Press, 1 (1952)—16 (1977) Progress in the Chemistry of Fats and Other Lipids CODEN).

Unequivocal proof of the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240) and for seeds by Focks & Benning (1998, Plant Physiol. 118:91-101).

Positional analysis of the fatty acid composition at the C-1, C-2, or C-3 positions of the glycerol backbone is determined by lipase digestion (See, e.g., Siebertz & Heinz 1977, Z. Naturforsch. 32c:193-205, and Christie, 1987, Lipid Analysis $2^{nd}$ Edition, Pergamon Press, Exeter, ISBN 0-08-023791-6).

A typical way to gather information regarding the influence of increased or decreased protein activities on lipid and sugar biosynthetic pathways is for example via analyzing the carbon fluxes by labeling studies with leaves or seeds using $^{14}C$-acetate or $^{14}C$-pyruvate (See, e.g. Focks & Benning, 1998, Plant Physiol. 118:91-101; Eccleston & Ohlrogge, 1998, Plant Cell 10:613-621). The distribution of $^{14}C$ into lipids and aqueous soluble components can be determined by liquid scintillation counting after the respective separation (for example on TLC plates) including standards like $^{14}C$-sucrose and $^{14}C$-malate (Eccleston & Ohlrogge, 1998, Plant Cell 10:613-621).

Material to be analyzed can be disintegrated via sonification, glass milling, liquid nitrogen and grinding, or via other applicable methods. The material has to be centrifuged after disintegration. The sediment is resuspended in distilled water, heated for 10 minutes at 100° C., cooled on ice and centrifuged again, followed by extraction in 0.5M sulfuric acid in methanol containing 2% dimethoxypropane for 1 hour at 90° C., leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 minutes at 240° C. The identity of resulting fatty acid methylesters is defined by the use of standards available from commercial sources (e.g., Sigma).

In the case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves," Methods Enzymol. 174:518-552; for other methods, see also Härtel et al., 1998, Plant Physiol. Biochem. 36:407-417 and Focks & Benning, 1998, Plant Physiol. 118:91-101).

For the extraction of soluble sugars and starch, 50 seeds are homogenized in 500 μl of 80% (v/v) ethanol in a 1.5-ml polypropylene test tube and incubated at 70° C. for 90 minutes. Following centrifugation at 16,000 g for 5 minutes, the supernatant is transferred to a new test tube. The pellet is extracted twice with 500 μl of 80% ethanol. The solvent of the combined supernatants is evaporated at room temperature under a vacuum. The residue is dissolved in 50 μl of water, representing the soluble carbohydrate fraction. The pellet left from the ethanol extraction, which contains the insoluble carbohydrates including starch, is homogenized in 200 μl of 0.2N KOH, and the suspension is incubated at 95° C. for 1 hour to dissolve the starch. Following the addition of 35 μl of 1N acetic acid and centrifugation for 5 minutes at 16,000 g, the supernatant is used for starch quantification.

To quantify soluble sugars, 10 μl of the sugar extract is added to 990 μl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose, and sucrose, 4.5 units of hexokinase, 1 unit of phosphoglucoisomerase, and 2 μl of a saturated fructosidase solution are added in succession. The production of NADPH is photometrically monitored at a wavelength of 340 nm. Similarly, starch is assayed in 30 μl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding," Anal. Biochem. 72:248-254). For quantification of total seed protein, 15-20 seeds are homogenized in 250 μl of acetone in a 1.5-ml polypropylene test tube. Following centrifugation at 16,000 g, the supernatant is discarded and the vacuum-dried pellet is resuspended in 250 μl of extraction buffer containing 50 mM Tris-HCl, pH 8.0, 250 mM NaCl, 1 mM EDTA, and 1% (w/v) SDS. Following incubation for 2 hours at 25° C., the homogenate is centrifuged at 16,000 g for 5 minutes, and 200 ml of the supernatant will be used for protein measurements. In the assay, γ-globulin is used for calibration. For protein measurements, Lowry D C protein assay (Bio-Rad) or Bradford-assay (Bio-Rad) are used.

Enzymatic assays of hexokinase and fructokinase are performed spectropho-tometrically according to Renz et al. (1993, Planta 190:156-165); enzymatic assays of phosphogluco-isomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase and pyruvate kinase are performed according to Burrell et al. (1994, Planta 194:95-101); and enzymatic assays of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Härtel et al. (1998, Plant Physiol. Biochem. 36:407-417), and metabolites are measured as described in Jelitto et al. (1992, Planta 188:238-244).

In addition to the measurement of the final seed storage compound (i.e., lipid, starch or storage protein), it is also possible to analyze other components of the metabolic pathways utilized for the production of a desired seed storage compound, such as intermediates and side-products, to determine the overall efficiency of production of the compound (Fiehn et al., 2000, Nature Biotech. 18:1447-1161).

For example, yeast expression vectors comprising the nucleic acids disclosed herein, or fragments thereof, can be constructed and transformed into *Saccharomyces cerevisiae* using standard protocols. The resulting transgenic cells can then be assayed for alterations in sugar, oil, lipid, or fatty acid contents.

Similarly, plant expression vectors comprising the nucleic acids disclosed herein, or fragments thereof, can be constructed and transformed into an appropriate plant cell such as *Arabidopsis*, soybean, rape, maize, wheat, *Medicago truncatula*, etc., using standard protocols. The resulting transgenic cells and/or plants derived therefrom can then be assayed for alterations in sugar, oil, lipid, or fatty acid contents.

Additionally, the sequences disclosed herein, or fragments thereof, can be used to generate knockout mutations in the genomes of various organisms, such as bacteria, mammalian cells, yeast cells, and plant cells (Girke at al., 1998, Plant J. 15:39-48). The resultant knockout cells can then be evaluated for their composition and content in seed storage compounds, and the effect on the phenotype and/or genotype of the mutation. For other methods of gene inactivation include U.S. Pat. No. 6,004,804 and Puttaraju et al., 1999, Nature Biotech. 17:246-252).

Example 18

Purification of the Desired Product from Transformed Organisms

An LMP can be recovered from plant material by various methods well known in the art. Organs of plants can be separated mechanically from other tissue or organs prior to isolation of the seed storage compound from the plant organ. Following homogenization of the tissue, cellular debris is removed by centrifugation and the supernatant fraction containing the soluble proteins is retained for further purification of the desired compound. If the product is secreted from cells grown in culture, then the cells are removed from the culture by low-speed centrifugation, and the supernatant fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey J. E. & Ollis D. F., 1986, Biochemical Engineering Fundamentals, McGraw-Hill:New York.

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzynatic assay, or microbiologically. Such analysis methods are reviewed in: Patek et al. (1994, Appl. Environ. Microbiol. 60:133-140), Malakhova et al. (1996, Biotekhnologiya 11:27-32), Schmidt et al. Bioprocess Engineer 19:67-70), Ulmann's Encyclopedia of Industrial Chemistry (1996, Vol. A27, VCH: Weinheim, p. 89-90, p. 521-540, p. 540-547, p. 559-566, 575-581 and p. 581-587) and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

Example 19

Screening for Increased Stress Tolerance and Plant Growth

The transgenic plants are screened for their improved stress tolerance demonstrating that transgene expression confers stress tolerance. The transgenic plants are further screened for their growth rate demonstrating that transgene expression confers increased growth rates and/or increased seed yield.

Classification of the proteins was done by Blasting against the BLOCKS database (S. Henikoff & J. G. Henikoff, Genomics 19:97-107 (1994)).

Those skilled in the art will recognize, or will be able to ascertain using no more than routine experimentation, many equivalents to the specific embodiments of the invention described herein. Such equivalents are intended to be encompasses by the claims to the invention disclosed and claimed herein.

Example 20

Construction of a Binary Construct for Suppression of Translation of osw20

The sequence of osw 20 (SEQ ID NO:11) was cloned using the forward and reverse primers (SEQ ID NOS:95 and 96) as described above. A construct for suppression of osw20 by mRNA interference was constructed as follows. The plasmid pGEM-Te carrying SEQ ID NO:11 (amplified with SEQ ID NOS:95 and 96) was digested with the restriction enzyme StuI, making use of the restriction site introduced by the reverse primer. After ethanol precipitation, the plasmid was digested with the restriction enzyme PstI making use of the PstI site introduced by the forward primer. The resulting liberated nucleotide was purified from an agarose gel using standard methods and digested with the restriction enzymes HindIII and NdeI simultenously. HindIII cut the sequence in two fragments of the same size, and NdeI cleaved the rear half of the original nucleotide into two smaller fragments. The front half of the osw20 sequence (approx 530 bp, between the restriction sites of Pst I and Hind III) was purified from an agarose gel and the nucleotide overhangs filled up to blunt ends using the large fragment of the Klenow polymerase.

The plasmid pGEM-Te carrying the osw20 sequence was digested with StuI, and the blunted osw20 fragment was ligated behind the osw20 sequence. The resulting clones were screened for one with a reverse orientation of the inserted fragment behind the open reading frame of osw20. This construct was called osw20 suppression (SEQ ID NO:123). It was liberated from the pGEM-Te vector by a digestion with NotI and gel purification, and ligated into the binary vector pSUN300 under control of the seed specific USP promoter (See FIG. 1).

Appendix

```
Nucleic Acid Sequence of Osw26
ATGCAGACCGTTTCTCGGAGATTAGCTGGTGAAAATTTGAGCTCTCGCACATCGATTTAC   (SEQ ID NO:121)

TCTCTCAAATCGGTTTATCCTGTTTCCGATCGCTGTTACGGTGAGTATGATCGGCGTTAT

GCCTCTAGGCTTACCACCAAAGGTATTGGACATCTGGTCCGCAAGGGTACTGGTGGAAGA

TCGTCTGTTAGTGGGATAGTTGCTACAGTATTCGGAGCTACTGGTTTCCTTGGGCGTTAC

TTGGTGCAACAGCTTGCTAAAACGGGTTCACAAGTGCTAGTACCATTTAGAGGTTCCGAA

GATTCGCCCCGTCATCTCAAACTGATGGGCGATTTGGGGCAGATTGTTCCCATGAAATAT

AATCCTAGAGATGAAAACTCAATTAAGGCAGTCATGGCCAAGGCAAATGTTGTGATTAAT

CTCATAGGAAGGGAATATGAAACCAGAAATTATAGTTTTGAGGAAGTGAACCATCATATG

GCTGAACAACTTGCAAAGATTTCCAAAGAACATGGTGGAATCATGAGATTTATACAACTG

TCGTGTTTAGGTGCATCTAAATCATCTCCATGTAGGATGCTTCAAGCCAAGGCTGCTGCA

GAAGAATCCATCTTACGTGAATTGCCTGAGGCCACAATACTGCGACCTGCAGTGATGGTT

GGTACAGAAGATCGGATCTTGAACCCATGGGCTCAGTTCGCTAAAAAATATAACTTTCTT

CCAATGATCGGGGGTGGTTCTACTAAGATTCAGCCTGTGTATGTTGCTGATGTCGCCTCT
```

-continued

```
GCAGTTGTTGCGGCATTAAGTGATGACGGTAGTAGCATGGGAAAAGTGTATGAACTTGGT

GGGCCTGATGTTTATACACTGCATCAATTGGCTGAACTTATGTATGAAACGATTCGAGAA

TGGCCTCATTATAACGTTCCTTTCCCTATTGCTAAGGCGATCTCAACACCTCGAGAAGTA

TTTCTTAATAAAGTTCCCTTCCCGTTACCCTCACCAATCATCTTCAATTTGGATGTGATT

AATGCTCTTTCTTCAGATACTCTCGTCTCAAAAGATGCTCTGACATTCAATGATCTTGAG

CTFFGTGCCACATAAGGTGAAGGGATATCCTATTGAGTACCTTATCCAGTATCGCAAGGG

TGGACCCAATTACGGCTCTACAGTCAGTGAAAGAGTGACTCCAGAGTCTTATCCTTGA
```

Deduced Amino Acid Sequence of Osw26
MQTVSRRLARENLSSRTSIYSLKSLYPVSDRCYGEYDRRYASTLTTKGIGHLVRKGTGGR (SEQ ID NO:122)

SSVSGIVATVFGATGFLGRYLVQQLAKTGSQVLVPFRGSEDSPRHLKLMGDLGQIVPMKY

NPRDENSIKAVMAKANVVINLIGREYETRNYSFEEVNHHMAEQLAKISKEHGGIMRFIQL

SCLGASKSSPSRMLQAKAAAEESILRELPEATILRPAVMVGTEDRILNPWAQFAKKYNFL

PMIGGGSTKIQPVYVADVASAVVAALSDDGSSMGKVYELGGPDVYTLHQLAELMYETIRE

WPHYVNVPFPIAKAISTPREVFLNKVPFPLPSPIIFNLDVINALSSDTLVSKDALTFNDL

ELVPHKVKGYPIEYLIQYRKGGPNYGSTVSERVTPESYP

Nucleic Acid Sequence of Osw20 Suppression Construct
ATGGAGTGTAGTTCAGTGAGTGTACTAGGAATATTACTGGTATTCCTCTCCTTCATAACC (SEQ ID NO:123)

```
TTGTCACCATCTCCGGGCAGAATCTTCCGGCGGTGGGTTTGTTCACTTTCGGAGATTCCA

ACTCGACGCTGGAAATAAAAAGTTCCTCACAAGTGCTCCACTTCCTCAAAACTTTTGGCC

TTACGGTAAATCTCGAGATGACCCTAAGGGCAAGTTTTCTGATGGCAAAATTGTCCCGGA

CTTTATTGCAAAATTCATGGGATACCACACGATTTACCGCCGGCGCTAAAACCCGGCAC

CGATGTGTCACGAGGAGCCAGCTTCGCCGTCGGGTCCGCTTCCATTCTTGGATCTCCAAA

AGATTCTTTGGCTCTGAATCAACAAGTGAGGAAATTCAATCAGATGATATCAAATTGGAA

AGTGGATTACATTCAGAAATCAGTGTTTATGATTAGCATTGGTATGGAAGATTACTACAA

CTTTACCAAAAACAATCCTAATGCTGAAGTTTCTGCTCAACAAGCTTTCGTTACTTCTGT

CACTAACCGGTTTAAGAGTGATATCAACTTGTTGTATTCATCTGGAGCTAGTAAATTCGT

CGTACACTTGCTAGCGCCATTAGGTTGTTTACCGATCGCAAGACAAGAATTTAAAACCGG

TAACAATTGTTACGAGAAACTCGATGATTTGGCCAAACAACACAACGCTAAAATTGGACC

GATTTTGAACGAAATGGCGGAAACTAAACCGGATTTCGAATTCACCGTTTTCGATTTACT

ACAACGTTATTCTTCGCAGGACACAAAGAAACATGAACTACCGGTTTTCCGTGACGAATA

TATCGTGTTGCGGTGTTGGGAGGCATTATGCATATGGTTGTGGTTTACCTAACGTGCACT

CGAAGTTATGCGAATATCAAAGATCCTACCTTTACTTCGACGCACGTCATAACACAGAGA

AAGCACAAGAAGCGTTTGCTCATCTTATCTTTGGAGCTGACCCAAATGTTATCCAACCTA

TGAATGTTCGTGAGCTCATGGTGTATCCTGTTAATGAGCCTATGCGTGAGTTTTGGGAGG

ATCCAATGGATGAGAAGTTATCGTTAGTCCAATACTAGAGGAGCTTGTTGAGCAGAAACT

TCAGCATTAGGATTGTTTTTGGTAAAGTTGTAGTAATCTTCCATACCAATGCTAATCATA

AACACTGATTTCTGAATGTAATCCACTTTCCAATTTGATATCATCTGATTGAATTTCCTC

ACTTGTTGATTCAGAGCCAAAGAATCTTTTGGAGATCCAAGAATGGAAGCGGACCCGACG

GCGAAGCTGGCTCCTCGTGAGACATCGGTGCCGGGTTTTAGCGCCGGCGGTAAATCGTGT

GGTATCCCCATGAATTTTGCAATAAAGTCCGGGACAATTTTGCCATCAGAAAACTTGCCC

TTAGGGTCATCTCGAGATTTACCGTAAGGCCAAAAGTTTTGAGGAAGTGGAGCACTTGTG
```

-continued

AGGAACTTTTTATTTCCAGCGTCGAAGTTGGAATCTCCGAAAGTGAACAAACCCACCGCC

GGAAGATTCTGCCCGGAGATGGTGACAAGGTTATGAAGGAGAGGAAATACCAGTAATATT

CCTAGTACACTCACTGAACTACACTCCATGGC

---

We claim:

1. An isolated lipid metabolism protein (LMP) nucleic acid comprising a polynucleotide sequence selected from the group consisting of:
   a) the full-length polynucleotide as shown in SEQ ID NO:19;
   b) a polynucleotide sequence encoding the full-length polypeptide as shown in SEQ ID NO:20;
   c) a polynucleotide sequence encoding a polypeptide having at least 95% identity to the polypeptide of SEQ ID NO:20, wherein expression of said polynucleotide in a plant results in an increase in total fatty acids in seed of said plant; and
   d) a polynucleotide sequence complementary to the full-length polynucleotide sequence of SEQ ID NO: 19.

2. The isolated LMP nucleic acid of claim 1, wherein the polynucleotide sequence encodes the full-length polypeplide sequence as shown in SEQ ID NO:20.

3. An expression vector comprising an LMP nucleic acid, wherein the nucleic acid comprises a polynucleotide selected from the group consisting of
   a) the polynucleotide of SEQ ID NO:19;
   b) a polynucleotide encoding the polypeptide of SEQ ID NO:20; and
   c) a polynucleotide encoding a polypeptide having at least 95% identity to the polypeptide of SEQ ID NO:20, wherein expression of said polynucleotide in a plant results in an increase in total fatty acids in seed of said plant.

4. The expression vector of claim 3, wherein the LMP nucleic acid is operatively linked to a heterologous promoter selected from the group consisting of a seed-specific promoter, a root-specific promoter, and a non-tissue-specific promoter.

5. A method of producing a transgenic plant having an increased level of total fatty acids in the seeds of said plant, said method comprising the steps of transforming a plant cell with the expression vector of claim 3 and generating from the plant cell a transgenic plant having an increased level of total fatty acids in the seeds.

6. The method of claim 5, wherein the increased level of total fatty acids is due to the overexpression of the LMP nucleic acid, wherein said nucleic acid is operatively linked to a promoter selected from the group consisting of: constitutive promoters, inducible promoters, tissue-specific promoters, seed-specific promoters, and root-specific promoters.

7. A method of increasing the level of total fatty acids in the seed of a plant comprising increasing the expression of an LMP nucleic acid in the plant, by transforming the plant with the expression vector of claim 3.

8. The isolated LMP nucleic acid of claim 1, wherein the polynucleotide sequence is shown in SEQ ID NO:19.

9. The isolated LMP nucleic acid of claim 1, wherein the nucleic acid comprises a polynucleotide sequence encoding a polypeptide having at least 95% identity to the polvpeptide of SEQ ID NO:20, wherein expression of said polynucleotide in a plant results in an increase in total fatty acids in seed of said plant or a polynucleotide sequence that encodes the full-length polypeptide sequence of SEQ ID NO:20.

10. A transgenic plant cell comprising the expression vector of claim 3.

11. A transgenic plant comprising the expression vector of claim 3.

12. The transgenic plant of claim 11, wherein the plant is a dicotyledonous plant.

13. The transgenic plant of claim 11, wherein the plant is a monocotyledonous plant.

14. The transgenic plant of claim 11, wherein the plant is selected from the group consisting of rapeseed, canola, linseed, soybean, sunflower, maize, oat, rye, barley, wheat, sugarbeet, tagetes, cotton, oil palm, coconut palm, flax, castor and peanut.

15. A seed produced by the transgenic plant of claim 11, wherein the plant is true breeding for an increased level of total fatty acids in the seeds of the plant as compared to the seeds of a control plant, and wherein the control plant is of the same ecotype as the transgenic plant but has not been transformed with the LMP nucleic acid.

16. The method of claim 5, wherein the polynucleotide sequence is shown in SEQ ID NO:19.

17. The method of claim 5, wherein the polynucleotide sequence encodes the full-length polypeptide sequence as shown in SEQ ID NO:20.

18. The method of claim 5, wherein the nucleic acid comprises a polynucleotide sequence encoding a polypeptide having at least 95% identity to the polypeptide of SEQ ID NO:20, wherein expression of said polynucleotide in a plant results in an increase in total fatty acids in seed of said plant or a polynucleotide sequence that encodes the full-length polypeptide sequence of SEQ ID NO:20.

19. The method of claim 7, wherein the nucleic acid comprises the full-length polynucleotide sequence as defined in SEQ ID NO:19.

20. The method of claim 7, wherein the nucleic acid comprises a polynucleotide sequence encoding a polvpeptide having at least 95% identity to the polypeptide of SEQ ID NO:20, wherein expression of said polynucleotide in a plant results in an increase in total fatty acids in seed of said plant or a polynucleotide sequence that encodes the full-length polypeptide sequence of SEQ ID NO:20.

* * * * *

UNITED STATES PATENT AND TRADEMARK OFFICE
CERTIFICATE OF CORRECTION

| | |
|---|---|
| PATENT NO. | : 7,238,856 B2 |
| APPLICATION NO. | : 11/021619 |
| DATED | : July 3, 2007 |
| INVENTOR(S) | : Oliver Oswald et al. |

It is certified that error appears in the above-identified patent and that said Letters Patent is hereby corrected as shown below:

On the Title Page:

In the References Cited, in Page 2 under OTHER PUBLICATIONS,

Left Column,

Starting with Hurry et al., 2000, "The Plant Journal, 27(3) 383-396" should read -- The Plant Journal 24(3) 383-396 --.

Please insert -- 2001 -- after Merlot et al.

Right Column,

Starting with Ohlrogge et al., 2000, "Biochem. Sci. Trans." should read -- Biochem. Soc. Trans. --.

"Parveez, et al., 1000" should read -- Parveez, et al., 2000 --.

"Taipalensee et al." should read -- Taipalensuu et al. --.

In the Claims,

In Claim 2, in column 191, on line 52, "polynucleotide sequence encodes the full-length polypeplide" should read -- polynucleotide sequence encodes the full-length polypeptide --.

In Claim 9, in column 192, on line 58, "a polypeptide having at least 95% identity to the polvpeptide" should read -- a polypeptide having at least 95% identity to the polypeptide --.

UNITED STATES PATENT AND TRADEMARK OFFICE
CERTIFICATE OF CORRECTION

PATENT NO.       : 7,238,856 B2
APPLICATION NO.  : 11/021619
DATED            : July 3, 2007
INVENTOR(S)      : Oliver Oswald et al.

It is certified that error appears in the above-identified patent and that said Letters Patent is hereby corrected as shown below:

In Claim 20, in column 194, on line 12 to line 13, "a polynucleotide sequence encoding a polvpep-tide" should read -- a polynucleotide sequence encoding a polypep-tide --.

Signed and Sealed this

First Day of April, 2008

JON W. DUDAS
*Director of the United States Patent and Trademark Office*

SEQUENCE LISTING

<160> NUMBER OF SEQ ID NOS: 123

<210> SEQ ID NO 1
<211> LENGTH: 2976
<212> TYPE: DNA
<213> ORGANISM: Arabidopsis thaliana

<400> SEQUENCE: 1

| | | | | |
|---|---|---|---|---|
| atggcaacgg | gggctgagaa | ccaatggctt | aaaggaagag tgaaggctgt tacctccgga | 60 |
| gactgcttag | tgatcacggc | tttgagccac | aacagagctg acctccacc ggaaaagacc | 120 |
| attactttt | cttctcttat | ggcacctaag | atggctcgca gaggaggtat agatgagcct | 180 |
| tttgcatggg | aaagcaaaga | attttgagg | aaactttgca taggaaagga ggttgcattc | 240 |
| aaagtggatt | acaaggtgga | agctattgct | ggaagagaat ttggctctgt tttccttggc | 300 |
| aacgagaatc | ttgctaagct | tgttgttaaa | actggttggg caaaggttag ggagccaggt | 360 |
| cagcagaatc | aggacaaggt | tagtccttac | attaaagagt tgctacagct tgaagagctg | 420 |
| gccaagcagg | aaggatatgg | tcgttggagc | aaggttcctg tgctgctga ggcatctatc | 480 |
| agaaatcttc | ctccttctgc | cattggggat | tctgctggct ttgatgccat gggccttta | 540 |
| gctgcaaaca | agggcaagcc | tatggaaggt | attgtagagc aagtgcgtga tggaagtact | 600 |
| attcgggttt | atcttcttcc | agagttccag | tttgtgcaag tatttgttgc gggagtccag | 660 |
| gctccatcaa | tgggaaggcg | aaccacaaat | ggaagtgttg ttgagacagt tccagatgag | 720 |
| ccgaatggag | atgtttctgc | tgagtcacga | ggtcctctaa cgacagctca gagacttgct | 780 |
| gcctctgcag | catcgtctgt | cgaggttttcc | tctgatccat ttgcaactga agccaagtac | 840 |
| tttaccgaac | accgtgttct | tagtagagat | gttcgcattg ttcttgaagg cgttgacaaa | 900 |
| tcaacaatc | tgattggttc | agttcattat | tctgatgggg aaacagttaa agacttgggg | 960 |
| ttggagctcg | ttgaaaatgg | tcttgctaaa | tttgttgaat ggagtgccaa catgatggag | 1020 |
| gaggaagcta | agaaaaagtt | gaaagctgca | gaacttcaat gcaagaaaga taaggttaaa | 1080 |
| atgtgggcaa | actacgttcc | tccagctaca | aactctaagg caattcatga ccagaacttt | 1140 |
| acggaaaagg | tagtggaagt | ggtgagtggg | gattgtctaa tagttgccga tgatgctgtt | 1200 |
| ccatttggga | gtccagcagc | agagagacgg | gtctgtcttt cgagtatcag atctccaaaa | 1260 |
| atgggcaacc | cacgtagaga | agagaaacca | gctccttatg ctcgggaagc aagagaattt | 1320 |
| ctgagacaac | gacttattgg | caaacaggtt | attgttcaaa tggaatattc aaggaaagtc | 1380 |
| acccaaggag | atggtcctac | cacatctgga | gctgctgata ggttcatgga ttttggctca | 1440 |
| gtgttccttc | catctgctgc | caaagccgat | tctgatgaag tgactgcacc acctgctgca | 1500 |
| gcaattgctg | gcagtcagcc | ggttggtgtg | aatattgctg agctcgttct tgtccgtggt | 1560 |
| tttgaaaatg | tggttagaca | tagagatttt | gaagagcgat caaaccatta tgatgctctt | 1620 |
| ctggctgctg | aagctcgtgc | tctggctgga | agaaaggaa tccattctgc aaaagaatct | 1680 |
| ccagccatgc | acatcacaga | cctaactgtg | tcggcagcta agaaagctaa agatttcctg | 1740 |

-continued

```
ccatccctgc aaagaatcag gagaataccc gctgttgtgg aatatgtcct cagcggacat      1800
cggtttaagc tttatatccc aaagataaca tgtagcatag ccttttcatt ctctggtgtc      1860
agatgtcctg gccgtggcga accttattca gaagaagcta tctctgtaat gagacgtagg      1920
atcatgcaga gagatgttga gattgaagtt gaaaccgtgg atagaaccgg tactttcttg      1980
ggatccatgt gggaatcgag gacaaacgtg gctacagttc tgcttgaagc tggcttagca      2040
aaaatgcaga ctagctttgg tgcagacagg atcgccgaag cacatcttct tgaacaggca      2100
gagagatctg ctaaaaacca gaaactgaag atttgggaaa actatgttga aggagaagaa      2160
gtctcaaacg gaaatactaa caccgtagaa accaggcaaa aggagacctt aaaggttgtt      2220
gttacagaag tacttggagg tggtcggttc tatgttcaat ctgctggaga tcagaaaata      2280
gcttcgattc agaaccagct tgcatcattg agtattaaag acgctcccat tatcggatcc      2340
tttaatccaa agagaggtga catcgtcctt gcacagttta gccttgataa ctcctggaac      2400
cgtgcaatga ttgtgacagc accccgagca gcggttcaat ccccagatga aaaattcgaa      2460
gtgttctaca tcgattatgg aaaccaagag acagttccat acagcgcaat cagaccaata      2520
gacccttcgg tatctgcagc accagggctc gctcagctct gcagacttgc ctacataaag      2580
gttccaagct tggaagacga ctttggtcct gaagcgggag agtatttgca tactgtaact      2640
ctgggtagtg gtaaagagtt caaagcagtg atagaagaaa gagacacatc tggaggcaaa      2700
gtcaaagggc aaggcactgg aactgaattc gttgtcactc tcattgctgt tgatgatgag      2760
atctctgtaa atgctgcaat gcttcaggaa ggaatagcga gaatggagaa acgtcagaaa      2820
tgggggcaca aaggcaaaca agctgctctt gatgctttag agaagttcca agaggaagct      2880
cgcaagtcga gaattggaat ctggcagtac ggtgacattg agtccgatga tgaggacact      2940
ggtccggcca gaaagcctgc tggtggtcgc cggtaa                                2976
```

<210> SEQ ID NO 2
<211> LENGTH: 991
<212> TYPE: PRT
<213> ORGANISM: Arabidopsis thaliana

<400> SEQUENCE: 2

```
Met Ala Thr Gly Ala Glu Asn Gln Trp Leu Lys Gly Arg Val Lys Ala
 1               5                  10                  15

Val Thr Ser Gly Asp Cys Leu Val Ile Thr Ala Leu Ser His Asn Arg
             20                  25                  30

Ala Gly Pro Pro Pro Glu Lys Thr Ile Thr Phe Ser Ser Leu Met Ala
         35                  40                  45

Pro Lys Met Ala Arg Arg Gly Gly Ile Asp Glu Pro Phe Ala Trp Glu
     50                  55                  60

Ser Lys Glu Phe Leu Arg Lys Leu Cys Ile Gly Lys Glu Val Ala Phe
 65                  70                  75                  80

Lys Val Asp Tyr Lys Val Glu Ala Ile Ala Gly Arg Glu Phe Gly Ser
                 85                  90                  95

Val Phe Leu Gly Asn Glu Asn Leu Ala Lys Leu Val Lys Thr Gly
            100                 105                 110

Trp Ala Lys Val Arg Glu Pro Gly Gln Gln Asn Gln Asp Lys Val Ser
        115                 120                 125

Pro Tyr Ile Lys Glu Leu Leu Gln Leu Glu Glu Leu Ala Lys Gln Glu
    130                 135                 140

Gly Tyr Gly Arg Trp Ser Lys Val Pro Gly Ala Ala Glu Ala Ser Ile
145                 150                 155                 160
```

-continued

```
Arg Asn Leu Pro Pro Ser Ala Ile Gly Asp Ser Ala Gly Phe Asp Ala
            165                 170                 175
Met Gly Leu Leu Ala Ala Asn Lys Gly Lys Pro Met Glu Gly Ile Val
        180                 185                 190
Glu Gln Val Arg Asp Gly Ser Thr Ile Arg Val Tyr Leu Leu Pro Glu
    195                 200                 205
Phe Gln Phe Val Gln Val Phe Ala Gly Val Gln Ala Pro Ser Met
210                 215                 220
Gly Arg Arg Thr Thr Asn Gly Ser Val Val Glu Thr Val Pro Asp Glu
225                 230                 235                 240
Pro Asn Gly Asp Val Ser Ala Glu Ser Arg Gly Pro Leu Thr Thr Ala
            245                 250                 255
Gln Arg Leu Ala Ala Ser Ala Ala Ser Ser Val Glu Val Ser Ser Asp
        260                 265                 270
Pro Phe Ala Thr Glu Ala Lys Tyr Phe Thr Glu His Arg Val Leu Ser
    275                 280                 285
Arg Asp Val Arg Ile Val Leu Glu Gly Val Asp Lys Phe Asn Asn Leu
290                 295                 300
Ile Gly Ser Val His Tyr Ser Asp Gly Glu Thr Val Lys Asp Leu Gly
305                 310                 315                 320
Leu Glu Leu Val Glu Asn Gly Leu Ala Lys Phe Val Glu Trp Ser Ala
            325                 330                 335
Asn Met Met Glu Glu Ala Lys Lys Lys Leu Lys Ala Ala Glu Leu
        340                 345                 350
Gln Cys Lys Lys Asp Lys Val Lys Met Trp Ala Asn Tyr Val Pro Pro
    355                 360                 365
Ala Thr Asn Ser Lys Ala Ile His Asp Gln Asn Phe Thr Gly Lys Val
370                 375                 380
Val Glu Val Val Ser Gly Asp Cys Leu Ile Val Ala Asp Asp Ala Val
385                 390                 395                 400
Pro Phe Gly Ser Pro Ala Ala Glu Arg Arg Val Cys Leu Ser Ser Ile
            405                 410                 415
Arg Ser Pro Lys Met Gly Asn Pro Arg Arg Glu Glu Lys Pro Ala Pro
        420                 425                 430
Tyr Ala Arg Glu Ala Arg Glu Phe Leu Arg Gln Arg Leu Ile Gly Lys
    435                 440                 445
Gln Val Ile Val Gln Met Glu Tyr Ser Arg Lys Val Thr Gln Gly Asp
    450                 455                 460
Gly Pro Thr Thr Ser Gly Ala Ala Asp Arg Phe Met Asp Phe Gly Ser
465                 470                 475                 480
Val Phe Leu Pro Ser Ala Ala Lys Ala Asp Ser Asp Glu Val Thr Ala
            485                 490                 495
Pro Pro Ala Ala Ala Ile Ala Gly Ser Gln Pro Val Gly Val Asn Ile
        500                 505                 510
Ala Glu Leu Val Leu Val Arg Gly Phe Gly Asn Val Val Arg His Arg
    515                 520                 525
Asp Phe Glu Glu Arg Ser Asn His Tyr Asp Ala Leu Leu Ala Ala Glu
    530                 535                 540
Ala Arg Ala Leu Ala Gly Lys Lys Gly Ile His Ser Ala Lys Glu Ser
545                 550                 555                 560
Pro Ala Met His Ile Thr Asp Leu Thr Val Ser Ala Ala Lys Lys Ala
            565                 570                 575
```

```
Lys Asp Phe Leu Pro Ser Leu Gln Arg Ile Arg Arg Ile Pro Ala Val
            580                 585                 590

Val Glu Tyr Val Leu Ser Gly His Arg Phe Lys Leu Tyr Ile Pro Lys
        595                 600                 605

Ile Thr Cys Ser Ile Ala Phe Ser Phe Ser Gly Val Arg Cys Pro Gly
    610                 615                 620

Arg Gly Glu Pro Tyr Ser Glu Glu Ala Ile Ser Val Met Arg Arg
625                 630                 635                 640

Ile Met Gln Arg Asp Val Glu Ile Glu Val Glu Thr Val Asp Arg Thr
                645                 650                 655

Gly Thr Phe Leu Gly Ser Met Trp Glu Ser Arg Thr Asn Val Ala Thr
            660                 665                 670

Val Leu Leu Glu Ala Gly Leu Ala Lys Met Gln Thr Ser Phe Gly Ala
        675                 680                 685

Asp Arg Ile Ala Glu Ala His Leu Leu Glu Gln Ala Glu Arg Ser Ala
    690                 695                 700

Lys Asn Gln Lys Leu Lys Ile Trp Glu Asn Tyr Val Glu Gly Glu Glu
705                 710                 715                 720

Val Ser Asn Gly Asn Thr Asn Thr Val Glu Thr Arg Gln Lys Glu Thr
                725                 730                 735

Leu Lys Val Val Val Thr Glu Val Leu Gly Gly Arg Phe Tyr Val
            740                 745                 750

Gln Ser Ala Gly Asp Gln Lys Ile Ala Ser Ile Gln Asn Gln Leu Ala
        755                 760                 765

Ser Leu Ser Ile Lys Asp Ala Pro Ile Ile Gly Ser Phe Asn Pro Lys
    770                 775                 780

Arg Gly Asp Ile Val Leu Ala Gln Phe Ser Leu Asp Asn Ser Trp Asn
785                 790                 795                 800

Arg Ala Met Ile Val Thr Ala Pro Arg Ala Val Gln Ser Pro Asp
                805                 810                 815

Glu Lys Phe Glu Val Phe Tyr Ile Asp Tyr Gly Asn Gln Glu Thr Val
            820                 825                 830

Pro Tyr Ser Ala Ile Arg Pro Ile Asp Pro Ser Val Ser Ala Ala Pro
        835                 840                 845

Gly Leu Ala Gln Leu Cys Arg Leu Ala Tyr Ile Lys Val Pro Ser Leu
    850                 855                 860

Glu Asp Asp Phe Gly Pro Glu Ala Gly Glu Tyr Leu His Thr Val Thr
865                 870                 875                 880

Leu Gly Ser Gly Lys Glu Phe Lys Ala Val Ile Glu Glu Arg Asp Thr
                885                 890                 895

Ser Gly Gly Lys Val Lys Gly Gln Gly Thr Gly Thr Glu Phe Val Val
            900                 905                 910

Thr Leu Ile Ala Val Asp Asp Glu Ile Ser Val Asn Ala Ala Met Leu
        915                 920                 925

Gln Glu Gly Ile Ala Arg Met Glu Lys Arg Gln Lys Trp Gly His Lys
    930                 935                 940

Gly Lys Gln Ala Ala Leu Asp Ala Leu Glu Lys Phe Gln Glu Glu Ala
945                 950                 955                 960

Arg Lys Ser Arg Ile Gly Ile Trp Gln Tyr Gly Asp Ile Glu Ser Asp
                965                 970                 975

Asp Glu Asp Thr Gly Pro Ala Arg Lys Pro Ala Gly Gly Arg Arg
            980                 985                 990
```

<210> SEQ ID NO 3
<211> LENGTH: 1014
<212> TYPE: DNA
<213> ORGANISM: Arabidopsis thaliana

<400> SEQUENCE: 3

```
atggcaacca tggctaggtc gtttctgcag gcgatatcga aggatgaggc ggtggctcct     60
ccgcttagag ttgttcagat cgaaggactg gctgtactaa agataatcaa acactgcaag   120
gagttttcac cgacccttgt cactggacag cttcttggac ttgatgttgg tagcgtcctc   180
gaagttacca attgttttcc tttcccggtc agggatgatg atgaagaaat tgaagctgat   240
ggtgctaatt atcagcttga tgatgagaga tgtctgaggg aggttaatgt tgacaacaac   300
actgttggct ggtatcaatc tacagttctt ggttcgtatc agactgtgga actgattgag   360
accttcatga attaccagga gaatatcaag aggtgtgtgt gcatcatata tgatccctct   420
aaagctgatc taggcgtctt agctttgaag gctttgaagc tttcagattc ctttatggag   480
ttgtaccgag gtgaaacttt actggcgaga agttgagag agaaaaattt ctcctggatg   540
gatattttg aggaaatacc tatcaaggtt tcaaattctg cccttgtcag tgcctttatg   600
accgaactgg agactgatac acctgtctca cagggcgatt atgatcgtct acactcatca   660
accactcctt tccttgagaa caatatggag ttttttgatta aatgcatgga tgatttatct   720
atggaacagc aaaagttcca gtattactac cggaacctgt ctcgtcagca agcacaacag   780
caagcctggc tccagaagag aagaacggaa acatggctc gtaaatcagc tggagaggag   840
cctttaccag aagaggatcc ttcaaaccca atctttaagg cgatccctga accatctagg   900
ctagagagtt tcctcatcac aaaccaagtc tcaaacttct gtggccaaat caatggagtg   960
gctggccaga acttcagcag gctttacctg accaaagcat gcacgacaa ctga         1014
```

<210> SEQ ID NO 4
<211> LENGTH: 337
<212> TYPE: PRT
<213> ORGANISM: Arabidopsis thaliana

<400> SEQUENCE: 4

```
Met Ala Thr Met Ala Arg Ser Phe Leu Gln Ala Ile Ser Lys Asp Glu
1               5                   10                  15
Ala Val Ala Pro Pro Leu Arg Val Val Gln Ile Glu Gly Leu Ala Val
            20                  25                  30
Leu Lys Ile Ile Lys His Cys Lys Glu Phe Ser Pro Thr Leu Val Thr
        35                  40                  45
Gly Gln Leu Leu Gly Leu Asp Val Gly Ser Val Leu Glu Val Thr Asn
    50                  55                  60
Cys Phe Pro Phe Pro Val Arg Asp Asp Asp Glu Glu Ile Glu Ala Asp
65                  70                  75                  80
Gly Ala Asn Tyr Gln Leu Asp Asp Glu Met Met Arg Cys Leu Arg Glu Val Asn
                85                  90                  95
Val Asp Asn Asn Thr Val Gly Trp Tyr Gln Ser Thr Val Leu Gly Ser
            100                 105                 110
Tyr Gln Thr Val Glu Leu Ile Glu Thr Phe Met Asn Tyr Gln Glu Asn
        115                 120                 125
Ile Lys Arg Cys Val Cys Ile Ile Tyr Asp Pro Ser Lys Ala Asp Leu
    130                 135                 140
Gly Val Leu Ala Leu Lys Ala Leu Lys Leu Ser Asp Ser Phe Met Glu
145                 150                 155                 160
```

```
Leu Tyr Arg Gly Gly Asn Phe Thr Gly Glu Lys Leu Arg Glu Lys Asn
                165                 170                 175
Phe Ser Trp Met Asp Ile Phe Glu Glu Ile Pro Ile Lys Val Ser Asn
            180                 185                 190
Ser Ala Leu Val Ser Ala Phe Met Thr Glu Leu Glu Thr Asp Thr Pro
        195                 200                 205
Val Ser Gln Gly Asp Tyr Asp Arg Leu His Ser Ser Thr Thr Pro Phe
    210                 215                 220
Leu Glu Asn Asn Met Glu Phe Leu Ile Lys Cys Met Asp Asp Leu Ser
225                 230                 235                 240
Met Glu Gln Gln Lys Phe Gln Tyr Tyr Tyr Arg Asn Leu Ser Arg Gln
                245                 250                 255
Gln Ala Gln Gln Gln Ala Trp Leu Gln Lys Arg Arg Thr Glu Asn Met
            260                 265                 270
Ala Arg Lys Ser Ala Gly Glu Glu Pro Leu Pro Glu Glu Asp Pro Ser
        275                 280                 285
Asn Pro Ile Phe Lys Ala Ile Pro Glu Pro Ser Arg Leu Glu Ser Phe
    290                 295                 300
Leu Ile Thr Asn Gln Val Ser Asn Phe Cys Gly Gln Ile Asn Gly Val
305                 310                 315                 320
Ala Gly Gln Asn Phe Ser Arg Leu Tyr Leu Thr Lys Ala Leu His Asp
                325                 330                 335
Asn

<210> SEQ ID NO 5
<211> LENGTH: 2496
<212> TYPE: DNA
<213> ORGANISM: Arabidopsis thaliana

<400> SEQUENCE: 5
atggcgcaac ccctcgtgaa gaaagacgat gatcacgacg atgagttgga gtattctcca      60
ttcatgggaa ttgagaaagg agcggttctt caagaggcta gagtctttaa tgaccctcag     120
gttgatccta gacgatgctc ccaggtcatt acgaagcttc tttatttgct taaccaaggg     180
gagtcattca ccaaggttga agcaacggaa gttttctttt cagttacaaa gcttttttcaa    240 tcaaaagaca cgggtttgag gagaatggtc tacttgatca ttaaggagtt atctccatca     300
tctgatgagg ttatcatcgt aacaagctct ctgatgaagg atatgaatag taaaattgat     360
atgtatcgag caaatgctat ccgtgtcctc tgccggataa tagacggaac ccttctcact     420
cagattgagc gatacttgaa acaagccatt gtggataaga tcccgttgt tcaagtgca      480 gctttagtca gtgggcttca cttgctcaag acaaacccag aaattgttaa agatggagc      540 aatgaagttc aagaaggtat tcaatccaga tcagcccttg ttcagttcca tgccctagct     600
ttgctccatc agatacgcca aaatgatcgc ttggctgtta gcaaattggt tggtagcttg     660 accagggggat ctgtccgctc tcccttggct cagtgtcttt tgatacaacg tccgttctat     720 gaattttttgg agagttgcct gcgccataag gcagaaatgg tgatccttga ggctgccagg     780
gcaattactg agcttgatgg tgtgacaagc cgagaactga ctccagcaat cactgttctt     840
cagctctttt tgagttcccc cagaccagtt ttgagatttg ccgctgtccg gactctgaac     900
aaggttgcaa tgactcatcc tatggctgtc accaactgca acattgatat ggagagttta     960
atctctgatc aaaatagaag cattgctaca ctcgcaataa ccacactatt gaaacagggg    1020
aacgaatcaa gtgtagaacg tttgatgaag cagataacta attttatgtc agatattgct    1080
```

```
gatgagttca aaattgtggt cgtggacgca ataagatcgt tgtgtgtgaa attcccactg   1140
aaatacagat ccttgatgac cttcttaagc aacattctta gggaagaagg tggatttgag   1200
tataaaagag caatagtaga ttctattgtg accattatca gagatattcc ggatgcaaag   1260
gaaagtggac tgcttcatct atgtgaattc attgaagatt gtgaattcac atatctttca   1320
acacagatcc ttcattttct gggaattgag gggcctaaca cctcagatcc aagcaagtat   1380
atacgatata tatataatcg tgtgcatcta gaaaacgcca ctgtccgggc tgctgctgtt   1440
tccacacttg caaagtttgg gtttatggtt gaatccttga agccccggat tactgttcta   1500
ttgaagcgtt gcatctatga cagtgatgat gaggtccgtg ataggggcaac actatatttg   1560 agtgagccct ctgaagaagc ttttgatatc aactccgtac ctaaggaagt taaatctcag   1620 cccctttgcag agaagaaagc ccagggtaaa agcccactg tcttggtgc accaccagct   1680 gcacctgctt ctggttttga tggctatgaa agacttctct catccattcc agagtttgcc   1740
gcctttggaa aacttttcaa gtcttcttta cctgtggagc taactgaagc agaaacagaa   1800
tacgctgtca atgttgttaa gcatatcttt gacagtcatg tggtgtttca gtacaactgc   1860
actaacacaa taccagagca gttgttggag agggtactga acattgaagc tgaggaattc   1920
agtgaagtaa cttcaaaggc cctaaactca cttccttacg attcacccgg tcaagccttt   1980
gtggtttttg agaagccagc tggggtccct gctgttggaa agttctccaa cacattgact   2040
ttcgttgtta aggaggtaca tgttgaccca agcacaggtg aagcagaaga tgatggagta   2100
gaagatgagt accagctaga ggatcttgag gttgtagctg gagattacat ggtgaaagtg   2160
ggtgtctcca atttcaggaa tgcgtgggaa agcatggatg aagaagatga gcgtgtagac   2220
gaatatggcc ttggccaaag agagagtttg ggagaagctg taaaggctgt catggatctt   2280
cttggcatgc agacttgtga ggggacggag acaattccgc tcaatgcaag gtcacacacg   2340
tgtctattgt caggtgtgta cataggcaac gtgaaagtgt tagtgagggc acagtttgga   2400
atggacagct caaaggacat tgcaatgaag ctgacagtta gagctgaaga cgtttctgtc   2460
gccgaggcca ttcacgagat tgttgccagc ggctaa                             2496
```

<210> SEQ ID NO 6
<211> LENGTH: 886
<212> TYPE: PRT
<213> ORGANISM: Arabidopsis thaliana

<400> SEQUENCE: 6

```
Met Ala Gln Pro Leu Val Lys Lys Asp Asp His Asp Asp Glu Leu
1               5                   10                  15

Glu Tyr Ser Pro Phe Met Gly Ile Glu Lys Gly Ala Val Leu Gln Glu
                20                  25                  30

Ala Arg Val Phe Asn Asp Pro Gln Val Asp Pro Arg Arg Cys Ser Gln
            35                  40                  45

Val Ile Thr Lys Leu Leu Tyr Leu Leu Asn Gln Gly Glu Ser Phe Thr
        50                  55                  60

Lys Val Glu Ala Thr Glu Val Phe Phe Ser Val Thr Lys Leu Phe Gln
65                  70                  75                  80

Ser Lys Asp Thr Gly Leu Arg Arg Met Val Tyr Leu Ile Ile Lys Glu
                85                  90                  95

Leu Ser Pro Ser Ser Asp Glu Val Ile Ile Val Thr Ser Ser Leu Met
                100                 105                 110

Lys Asp Met Asn Ser Lys Ile Asp Met Tyr Arg Ala Asn Ala Ile Arg
            115                 120                 125
```

```
Val Leu Cys Arg Ile Ile Asp Gly Thr Leu Leu Thr Gln Ile Glu Arg
    130                 135                 140

Tyr Leu Lys Gln Ala Ile Val Asp Lys Asn Pro Val Val Ser Ser Ala
145                 150                 155                 160

Ala Leu Val Ser Gly Leu His Leu Leu Lys Thr Asn Pro Glu Ile Val
                165                 170                 175

Lys Arg Trp Ser Asn Glu Val Gln Glu Gly Ile Gln Ser Arg Ser Ala
            180                 185                 190

Leu Val Gln Phe His Ala Leu Ala Leu Leu His Gln Ile Arg Gln Asn
        195                 200                 205

Asp Arg Leu Ala Val Ser Lys Leu Val Gly Ser Leu Thr Arg Gly Ser
    210                 215                 220

Val Arg Ser Pro Leu Ala Gln Cys Leu Leu Ile Arg Tyr Thr Ser Gln
225                 230                 235                 240

Val Ile Arg Asp Met Ala Asn His Gly Gln Ser Gly Glu Arg Pro Phe
                245                 250                 255

Tyr Glu Phe Leu Glu Ser Cys Leu Arg His Lys Ala Glu Met Val Ile
            260                 265                 270

Leu Glu Ala Ala Arg Ala Ile Thr Glu Leu Asp Gly Val Thr Ser Arg
        275                 280                 285

Glu Leu Thr Pro Ala Ile Thr Val Leu Gln Leu Phe Leu Ser Ser Pro
    290                 295                 300

Arg Pro Val Leu Arg Phe Ala Ala Val Arg Thr Leu Asn Lys Val Ala
305                 310                 315                 320

Met Thr His Pro Met Ala Val Thr Asn Cys Asn Ile Asp Met Glu Ser
                325                 330                 335

Leu Ile Ser Asp Gln Asn Arg Ser Ile Ala Thr Leu Ala Ile Thr Thr
            340                 345                 350

Leu Leu Lys Thr Gly Asn Glu Ser Ser Val Glu Arg Leu Met Lys Gln
        355                 360                 365

Ile Thr Asn Phe Met Ser Asp Ile Ala Asp Glu Phe Lys Ile Val Val
    370                 375                 380

Val Asp Ala Ile Arg Ser Leu Cys Val Lys Phe Pro Leu Lys Tyr Arg
385                 390                 395                 400

Ser Leu Met Thr Phe Leu Ser Asn Ile Leu Arg Glu Glu Gly Gly Phe
                405                 410                 415

Glu Tyr Lys Arg Ala Ile Val Asp Ser Ile Val Thr Ile Ile Arg Asp
            420                 425                 430

Ile Pro Asp Ala Lys Glu Ser Gly Leu Leu His Leu Cys Glu Phe Ile
        435                 440                 445

Glu Asp Cys Glu Phe Thr Tyr Leu Ser Thr Gln Ile Leu His Phe Leu
    450                 455                 460

Gly Ile Glu Gly Pro Asn Thr Ser Asp Pro Ser Lys Tyr Ile Arg Tyr
465                 470                 475                 480

Ile Tyr Asn Arg Val His Leu Glu Asn Ala Thr Val Arg Ala Ala Ala
                485                 490                 495

Val Ser Thr Leu Ala Lys Phe Gly Phe Met Val Glu Ser Leu Lys Pro
            500                 505                 510

Arg Ile Thr Val Leu Leu Lys Arg Cys Ile Tyr Asp Ser Asp Asp Glu
        515                 520                 525

Val Arg Asp Arg Ala Thr Leu Tyr Leu Ser Val Leu Gly Gly Asp Gly
    530                 535                 540
```

```
Thr Val Asp Thr Asp Lys Glu Ser Lys Asp Phe Leu Phe Gly Ser Leu
545                 550                 555                 560

Glu Val Pro Leu Val Asn Met Glu Thr Ser Leu Lys Asn Tyr Glu Pro
                565                 570                 575

Ser Glu Glu Ala Phe Asp Ile Asn Ser Val Pro Lys Glu Val Lys Ser
            580                 585                 590

Gln Pro Leu Ala Glu Lys Lys Ala Gln Gly Lys Lys Pro Thr Gly Leu
        595                 600                 605

Gly Ala Pro Pro Ala Ala Pro Ala Ser Gly Phe Asp Gly Tyr Glu Arg
    610                 615                 620

Leu Leu Ser Ser Ile Pro Glu Phe Ala Ala Phe Gly Lys Leu Phe Lys
625                 630                 635                 640

Ser Ser Leu Pro Val Glu Leu Thr Glu Ala Glu Thr Glu Tyr Ala Val
                645                 650                 655

Asn Val Val Lys His Ile Phe Asp Ser His Val Phe Gln Tyr Asn
            660                 665                 670

Cys Thr Asn Thr Ile Pro Glu Gln Leu Leu Glu Arg Val Asn Val Ile
        675                 680                 685

Val Asp Ala Ser Glu Ala Glu Phe Ser Glu Val Thr Ser Lys Ala
    690                 695                 700

Leu Asn Ser Leu Pro Tyr Asp Ser Pro Gly Gln Ala Phe Val Val Phe
705                 710                 715                 720

Glu Lys Pro Ala Gly Val Pro Ala Val Gly Lys Phe Ser Asn Thr Leu
                725                 730                 735

Thr Phe Val Val Lys Glu Val Asp Pro Ser Thr Gly Glu Ala Glu Asp
            740                 745                 750

Asp Gly Val Glu Asp Glu Tyr Gln Leu Glu Asp Leu Glu Val Val Ala
        755                 760                 765

Gly Asp Tyr Met Val Lys Val Gly Val Ser Asn Phe Arg Asn Ala Trp
    770                 775                 780

Glu Ser Met Asp Glu Glu Asp Glu Arg Val Asp Glu Tyr Gly Leu Gly
785                 790                 795                 800

Gln Arg Glu Ser Leu Gly Glu Ala Val Lys Ala Val Met Asp Leu Leu
                805                 810                 815

Gly Met Gln Thr Cys Glu Gly Thr Glu Thr Ile Pro Leu Asn Ala Arg
            820                 825                 830

Ser His Thr Cys Leu Leu Ser Gly Val Tyr Ile Gly Asn Val Lys Val
        835                 840                 845

Leu Val Arg Ala Gln Phe Gly Met Asp Ser Ser Lys Asp Ile Ala Met
    850                 855                 860

Lys Leu Thr Val Arg Ala Glu Asp Val Ser Val Ala Glu Ala Ile His
865                 870                 875                 880

Glu Ile Val Ala Ser Gly
                885

<210> SEQ ID NO 7
<211> LENGTH: 1131
<212> TYPE: DNA
<213> ORGANISM: Arabidopsis thaliana

<400> SEQUENCE: 7
atgccgatta gccggagagt tctgacgccg atcaccgccg ctccggttat cttagccgtc    60 cttttgcttct tcttttggtc atcaatcatc gggccggaca atttaaaggg cacgaaacac   120
gtccttcaag atgctaagac cattcctctt cccgtcgatg gaccagagag cctagagttc   180
```

-continued

```
gatccacaag gtgaaggccc ttacgttggc gtcaccgacg gtcgcattct caaatggcgc      240
ggtgaagaac tcggctgggt cgatttcgcc tacacttctc ctcacagaga taactgttcg      300
agtcatgagg tagtaccaag ttgtgggaga ccattgggac ttagcttcga gaggaaaaca      360
ggagatttgt acatatgtga tggttacttt ggggtcatga aggtcggacc agagggaggc      420
ctgggcgagt tagttgttga tgaagccgaa ggtcgtaaag ttatgtttgc aaccaaggg       480 gatatagacg aagaggaaga tatttctac ttcaatgata gcagcgatac ataccatttc      540
agggacgtat tttacgtgtc tttgtccggg acaaaggttg aagagtaat tagatacgat       600 atgaagaaga aagaggccaa agttattatg gacaaacttc gtttaccaaa tggtctagct      660
ctaagcaaaa acggttcgtt tgtagtcaca tgcgagagta gtacgaacat ttgccataga      720
atatgggtca aggtcccaa atccggaacc aacgaggttt cgcaacgct ccctggttcc        780 ccggacaata tccggcgtac gccaacaggc gatttctggg tcgcattaca ttgcaaaaag      840
aatttgttca cacgtgcagt tttgattcac acttgggtcg aaggttttt catgaacacg       900 atgaagatgg agactgtaat tcatttcatg aacggaggaa acctcatgg aattgtcgtg      960 aaactctctg gagagacagg agagattctt gagatacttg aggacagtga agggaagacg     1020
gtgaaatatg ttagtgaggc ttatgagaca aaagatggaa agttatggat cggatctgtg     1080
tattggccgg ccgtttgggt tcttgataca tcggtttatg attccatatg a             1131
```

<210> SEQ ID NO 8
<211> LENGTH: 376
<212> TYPE: PRT
<213> ORGANISM: Arabidopsis thaliana

<400> SEQUENCE: 8

```
Met Pro Ile Ser Arg Arg Val Leu Thr Pro Ile Thr Ala Ala Pro Val
1               5                   10                  15

Ile Leu Ala Val Leu Cys Phe Phe Trp Ser Ser Ile Ile Gly Pro
            20                  25                  30

Asp Asn Leu Lys Gly Thr Lys His Val Leu Gln Asp Ala Lys Thr Ile
        35                  40                  45

Pro Leu Pro Val Asp Gly Pro Glu Ser Leu Glu Phe Asp Pro Gln Gly
    50                  55                  60

Glu Gly Pro Tyr Val Gly Val Thr Asp Gly Arg Ile Leu Lys Trp Arg
65                  70                  75                  80

Gly Glu Glu Leu Gly Trp Val Asp Phe Ala Tyr Thr Ser Pro His Arg
                85                  90                  95

Asp Asn Cys Ser Ser His Glu Val Val Pro Ser Cys Gly Arg Pro Leu
            100                 105                 110

Gly Leu Ser Phe Glu Arg Lys Thr Gly Asp Leu Tyr Ile Cys Asp Gly
        115                 120                 125

Tyr Phe Gly Val Met Lys Val Gly Pro Glu Gly Gly Leu Ala Glu Leu
    130                 135                 140

Val Val Asp Glu Ala Glu Gly Arg Lys Val Met Phe Ala Asn Gln Gly
145                 150                 155                 160

Asp Ile Asp Glu Glu Glu Asp Ile Phe Tyr Phe Asn Asp Ser Ser Asp
                165                 170                 175

Thr Tyr His Phe Arg Asp Val Phe Tyr Val Ser Leu Ser Gly Thr Lys
            180                 185                 190

Val Gly Arg Val Ile Arg Tyr Asp Met Lys Lys Lys Glu Ala Lys Val
        195                 200                 205
```

```
Ile Met Asp Lys Leu Arg Leu Pro Asn Gly Leu Ala Leu Ser Lys Asn
    210                 215                 220

Gly Ser Phe Val Val Thr Cys Glu Ser Ser Thr Asn Ile Cys His Arg
225                 230                 235                 240

Ile Trp Val Lys Gly Pro Lys Ser Gly Thr Asn Glu Val Phe Ala Thr
                245                 250                 255

Leu Pro Gly Ser Pro Asp Asn Ile Arg Arg Thr Pro Thr Gly Asp Phe
            260                 265                 270

Trp Val Ala Leu His Cys Lys Lys Asn Leu Phe Thr Arg Ala Val Leu
        275                 280                 285

Ile His Thr Trp Val Gly Arg Phe Phe Met Asn Thr Met Lys Met Glu
    290                 295                 300

Thr Val Ile His Phe Met Asn Gly Gly Lys Pro His Gly Ile Val Val
305                 310                 315                 320

Lys Leu Ser Gly Glu Thr Gly Glu Ile Leu Glu Ile Leu Glu Asp Ser
                325                 330                 335

Glu Gly Lys Thr Val Lys Tyr Val Ser Glu Ala Tyr Glu Thr Lys Asp
            340                 345                 350

Gly Lys Leu Trp Ile Gly Ser Val Tyr Trp Pro Ala Val Trp Val Leu
        355                 360                 365

Asp Thr Ser Val Tyr Asp Ser Ile
370                 375

<210> SEQ ID NO 9
<211> LENGTH: 1113
<212> TYPE: DNA
<213> ORGANISM: Arabidopsis thaliana

<400> SEQUENCE: 9
atgcccatta atcagaaaat tccgacttgg tttgccgttc cggctgtttt tgctgtcttg      60
tccgtaatct cgtatcaaac cttaattgtg ccggaaaatt tagagggcgc caaaaatgta    120
ttgacaatgg ctaagaccat accaattcct gtcgctggac cggagagcat tgagtttgac    180
ccaaaaggag aaggtcctta tgctgcggtc gtggacggcc gtattctcaa gtggcgcggc    240
gatgatctcg gctgggttga ttttgcctac acatctcctc acagagggaa ctgttcaaaa    300
actgaagtag tgcctacttg tggaaggcca ttaggactta ctttcgagaa gaaaacggga    360
gatttgtaca tatgtgatgg ttacttgggg ctcatgaaag ttggaccaga gggaggcttg    420
gccgagttaa ttgttgatga agccgaaggt cgtaaagtta tgtttgctaa ccaagggat     480 atagacgaag aggaagatgt cttttacttc aatgatagta gtgacaagta tcatttcagg    540
gacgtatttt tcgtggctgt cagtggggag cggtcgggaa gagtgatcag atacgataag    600
aagacgaaag aagccaaagt tatcatggac aatctcgttt gtaacaacgg tttggctcta    660
aacaaagacc ggtcttttct aattacatgc gagtccggca caagtcttgt ccaccgatac    720
tggattaaag gtcccaaagc cgggactcgt gatatctttg cgaaggtccc aggttaccct    780
gacaacatcc ggctgacatc aactggagac ttttggattg gtttacactg caagaaaaat    840 ctgatagga gattgattgt gaagtacaaa tggcttggga aattggtaga aagacaatg      900 aaactggagt acgtgattgc ttttattaac ggatttaaac cgcacggagt cgccgtgaaa    960
atctccggcg agacgggaga ggtacttgag ttacttgagg acaaagaagg aaagacaatg   1020
aagtatgtaa gcgaggctta tgaaagagat gatggaaagt tgtggtttgg gtctgtttac   1080
tggccagccg tttgggttct tgatcgcaaa tga                                 1113
```

<210> SEQ ID NO 10
<211> LENGTH: 370
<212> TYPE: PRT
<213> ORGANISM: Arabidopsis thaliana

<400> SEQUENCE: 10

```
Met Pro Ile Asn Gln Lys Ile Pro Thr Trp Phe Ala Val Pro Ala Val
 1               5                  10                  15

Phe Ala Val Leu Ser Val Ile Ser Tyr Gln Thr Leu Ile Val Pro Glu
            20                  25                  30

Asn Leu Glu Gly Ala Lys Asn Val Leu Thr Met Ala Lys Thr Ile Pro
        35                  40                  45

Ile Pro Val Ala Gly Pro Glu Ser Ile Glu Phe Asp Pro Lys Gly Glu
    50                  55                  60

Gly Pro Tyr Ala Ala Val Val Asp Gly Arg Ile Leu Lys Trp Arg Gly
65                  70                  75                  80

Asp Asp Leu Gly Trp Val Asp Phe Ala Tyr Thr Ser Pro His Arg Gly
                85                  90                  95

Asn Cys Ser Lys Thr Glu Val Val Pro Thr Cys Gly Arg Pro Leu Gly
            100                 105                 110

Leu Thr Phe Glu Lys Lys Thr Gly Asp Leu Tyr Ile Cys Asp Gly Tyr
        115                 120                 125

Leu Gly Leu Met Lys Val Gly Pro Glu Gly Gly Leu Ala Glu Leu Ile
    130                 135                 140

Val Asp Glu Ala Glu Gly Arg Lys Val Met Phe Ala Asn Gln Gly Asp
145                 150                 155                 160

Ile Asp Glu Glu Glu Asp Val Phe Tyr Phe Asn Asp Ser Ser Asp Lys
                165                 170                 175

Tyr His Phe Arg Asp Val Phe Phe Val Ala Val Ser Gly Glu Arg Ser
            180                 185                 190

Gly Arg Val Ile Arg Tyr Asp Lys Lys Thr Lys Glu Ala Lys Val Ile
        195                 200                 205

Met Asp Asn Leu Val Cys Asn Asn Gly Leu Ala Leu Asn Lys Asp Arg
    210                 215                 220

Ser Phe Leu Ile Thr Cys Glu Ser Gly Thr Ser Leu Val His Arg Tyr
225                 230                 235                 240

Trp Ile Lys Gly Pro Lys Ala Gly Thr Arg Asp Ile Phe Ala Lys Val
                245                 250                 255

Pro Gly Tyr Pro Asp Asn Ile Arg Leu Thr Ser Thr Gly Asp Phe Trp
            260                 265                 270

Ile Gly Leu His Cys Lys Lys Asn Leu Ile Gly Arg Leu Ile Val Lys
        275                 280                 285

Tyr Lys Trp Leu Gly Lys Leu Val Glu Lys Thr Met Lys Leu Glu Tyr
    290                 295                 300

Val Ile Ala Phe Ile Asn Gly Phe Lys Pro His Gly Val Ala Val Lys
305                 310                 315                 320

Ile Ser Gly Glu Thr Gly Glu Val Leu Glu Leu Leu Glu Asp Lys Glu
                325                 330                 335

Gly Lys Thr Met Lys Tyr Val Ser Glu Ala Tyr Glu Arg Asp Asp Gly
            340                 345                 350

Lys Leu Trp Phe Gly Ser Val Tyr Trp Pro Ala Val Trp Val Leu Asp
        355                 360                 365

Arg Lys
```

-continued

```
<210> SEQ ID NO 11
<211> LENGTH: 1119
<212> TYPE: DNA
<213> ORGANISM: Arabidopsis thaliana

<400> SEQUENCE: 11
atggagtgta gttcagtgag tgtactagga atattactgg tatttcctct ccttcataac    60
cttgtcacca tctccgggca gaatcttccg gcggtgggtt tgttcacttt cggagattcc   120
aacttcgacg ctggaaataa aaagttcctc acaagtgctc cacttcctca aaacttttgg   180
ccttacggta aatctcgaga tgaccctaag ggcaagtttt ctgatggcaa aattgtcccg   240
gactttattg caaaattcat ggggatacca cacgatttac cgccggcgct aaaacccggc   300
accgatgtgt cacgaggagc cagcttcgcc gtcgggtccg cttccattct tggatctcca   360
aaagattctt ggctctgaa tcaacaagtg aggaaattca atcagatgat atcaaattgg   420
aaagtggatt acattcagaa atcagtgttt atgattagca ttggtatgga agattactac   480
aactttacca aaaacaatcc taatgctgaa gtttctgctc aacaagcttt cgttacttct   540
gtcactaacc ggtttaagag tgatatcaac ttgttgtatt catctggagc tagtaaattc   600
gtcgtacact tgctagcgcc attaggttgt ttaccgatcg caagacaaga atttaaaacc   660
ggtaacaatt gttacgagaa actcgatgat ttggccaaac aacacaacgc taaaattgga   720
ccgattttga cgaaatggc ggaaactaaa ccggatttcc aattcaccgt tttcgatttc   780
tacaacgtta ttcttcgcag gacacaaaga aacatgaact accggttttc cgtgacgaat   840
atatcgtgtt gcggtgttgg gacgcattat gcatatggtt gtggtttacc taacgtgcac   900
tcgaagttat gcgaatatca aagatcctac ctttacttcg acgcacgtca taacacagag   960
aaagcacaag aagcgtttgc tcatcttatc tttggagctg acccaaatgt tatccaacct  1020
atgaatgttc gtgagctcat ggtgtatcct gttaatgagc ctatgcgtga gttttgggag  1080
gatccaatgg atgagaagtt atcgttagtc caatactag                         1119

<210> SEQ ID NO 12
<211> LENGTH: 372
<212> TYPE: PRT
<213> ORGANISM: Arabidopsis thaliana

<400> SEQUENCE: 12

Met Glu Cys Ser Ser Val Ser Val Leu Gly Ile Leu Leu Val Phe Pro
1               5                   10                  15

Leu Leu His Asn Leu Val Thr Ile Ser Gly Gln Asn Leu Pro Ala Val
            20                  25                  30

Gly Leu Phe Thr Phe Gly Asp Ser Asn Phe Asp Ala Gly Asn Lys Lys
        35                  40                  45

Phe Leu Thr Ser Ala Pro Leu Pro Gln Asn Phe Trp Pro Tyr Gly Lys
    50                  55                  60

Ser Arg Asp Asp Pro Lys Gly Lys Phe Ser Asp Gly Lys Ile Val Pro
65                  70                  75                  80

Asp Phe Ile Ala Lys Phe Met Gly Ile Pro His Asp Leu Pro Ala
                85                  90                  95

Leu Lys Pro Gly Thr Asp Val Ser Arg Gly Ala Ser Phe Ala Val Gly
            100                 105                 110

Ser Ala Ser Ile Leu Gly Ser Pro Lys Asp Ser Leu Ala Leu Asn Gln
        115                 120                 125
```

```
Gln Val Arg Lys Phe Asn Gln Met Ile Ser Asn Trp Lys Val Asp Tyr
    130                 135                 140

Ile Gln Lys Ser Val Phe Met Ile Ser Ile Gly Met Glu Asp Tyr Tyr
145                 150                 155                 160

Asn Phe Thr Lys Asn Asn Pro Asn Ala Glu Val Ser Ala Gln Gln Ala
                165                 170                 175

Phe Val Thr Ser Val Thr Asn Arg Phe Lys Ser Asp Ile Asn Leu Leu
            180                 185                 190

Tyr Ser Ser Gly Ala Ser Lys Phe Val Val His Leu Leu Ala Pro Leu
        195                 200                 205

Gly Cys Leu Pro Ile Ala Arg Gln Glu Phe Lys Thr Gly Asn Asn Cys
    210                 215                 220

Tyr Glu Lys Leu Asn Asp Leu Ala Lys Gln His Asn Ala Lys Ile Gly
225                 230                 235                 240

Pro Ile Leu Asn Glu Met Ala Glu Thr Lys Pro Asp Phe Gln Phe Thr
                245                 250                 255

Val Phe Asp Phe Tyr Asn Val Ile Leu Arg Arg Thr Gln Arg Asn Met
            260                 265                 270

Asn Tyr Arg Phe Ser Val Thr Asn Ile Ser Cys Cys Gly Val Gly Thr
        275                 280                 285

His Tyr Ala Tyr Gly Cys Gly Leu Pro Asn Val His Ser Lys Leu Cys
    290                 295                 300

Glu Tyr Gln Arg Ser Tyr Leu Tyr Phe Asp Ala Arg His Asn Thr Glu
305                 310                 315                 320

Lys Ala Gln Glu Ala Phe Ala His Leu Ile Phe Gly Ala Asp Pro Asn
                325                 330                 335

Val Ile Gln Pro Met Asn Val Arg Glu Leu Met Val Tyr Pro Val Asn
            340                 345                 350

Glu Pro Met Arg Glu Phe Trp Glu Asp Pro Met Asp Gly Lys Leu Ser
        355                 360                 365

Leu Val Gln Tyr
    370

<210> SEQ ID NO 13
<211> LENGTH: 447
<212> TYPE: DNA
<213> ORGANISM: Helianthus annuus

<400> SEQUENCE: 13
atggttgaaa ccttgtttga agacatattt agggttgatc agcttgatcc agatggcaag    60
aagtttgaca agttaatcg cattgaagca aggagcgatc agttagatat gtacatgcag    120
ctggatgtga atacagaggt ttatcctatg catgtcggtg ataagtttat gatggtttta    180
gcatctacct taaatttgga tggaactccc gacagtggct ttttactcc gggtggcaga    240 aagtctctcg ctgacaaatt tgagtatgtg atgcacggca aattgtacag gatatctgag    300
gaagggtccg gagccaatgt taaagcggac atttatgttt cattcggcgg tttattaatg    360
ttgttgaggg gcgatccctc aattgcagct aaatttgagc ttgatcagag gttattcatc    420
cttatgagga aggtggataa ggcctag                                       447

<210> SEQ ID NO 14
<211> LENGTH: 148
<212> TYPE: PRT
<213> ORGANISM: Helianthus annuus
```

<400> SEQUENCE: 14

| | | | | | | | | | | | | | | | |
|---|---|---|---|---|---|---|---|---|---|---|---|---|---|---|---|
|Met|Val|Glu|Thr|Leu|Phe|Glu|Asp|Ile|Phe|Arg|Val|Asp|Gln|Leu|Asp|
|1| | |  |5| | | | |10| | | | |15| |

Pro Asp Gly Lys Lys Phe Asp Lys Val Asn Arg Ile Glu Ala Arg Ser
          20                25              30

Asp Gln Leu Asp Met Tyr Met Gln Leu Asp Val Asn Thr Glu Val Tyr
        35               40              45

Pro Met His Val Gly Asp Lys Phe Met Met Val Leu Ala Ser Thr Leu
50               55                60

Asn Leu Asp Gly Thr Pro Asp Ser Gly Phe Phe Thr Pro Gly Gly Arg
65               70               75             80

Lys Ser Leu Ala Asp Lys Phe Glu Tyr Val Met His Gly Lys Leu Tyr
        85               90              95

Arg Ile Ser Glu Glu Gly Ser Gly Ala Asn Val Lys Ala Asp Ile Tyr
          100            105           110

Val Ser Phe Gly Gly Leu Leu Met Leu Leu Arg Gly Asp Pro Ser Ile
       115              120             125

Ala Ala Lys Phe Glu Leu Asp Gln Arg Leu Phe Ile Leu Met Arg Lys
    130               135             140

Val Asp Lys Ala
145

<210> SEQ ID NO 15
<211> LENGTH: 675
<212> TYPE: DNA
<213> ORGANISM: Helianthus annuus

<400> SEQUENCE: 15

```
atggttgatg ctgagaaacg gcttttggcg aatgcactga agaccccga caatcagcat      60
tttgtgttac tttctgacag ctgtgtaccg ttgcacaact ttgactatat ttacaactat     120
cttatgtaca caaatgtcag cttcattgac agctttgagg atcctggtcc acatggaagt     180
ggtcggtact cggatcatat gttacctgaa gtcgaaaaaa aattctttag gaagggtgct     240
cagtggttca cgatgaagcg tcaacatgcc atcatagtta tggcggataa tctctactat     300
acaaagttca gagattattg taggccgggt atggacgggc gcaattgcta tgcagatgaa     360
cattatttgc caacattttt ccatatgttt gatcctactg ggattgcaaa ctggtcggtg     420
acacacgttg actggtcaga acgaaaatgg cacccgaaat catacgatct gaaggacgtt     480
tcttaccagc tcatcaaaaa tctctcgtct atcactgaaa gtgttcacga aacgagcgat     540
agaaagaggg taactacagt tacgccgtgt atgtggaatg gtatgaaccg gccgtgttac     600
ttatttgcaa gaaaattcct gcccgagacg ttagacactt tgattgacct tttccctcgt     660
tacacgacaa tatga                                                     675
```

<210> SEQ ID NO 16
<211> LENGTH: 377
<212> TYPE: PRT
<213> ORGANISM: Helianthus annuus

<400> SEQUENCE: 16

Met Gly Lys Lys Asp Met Pro Lys Arg Ser His Leu Lys Lys Pro Thr
1               5               10              15

Trp Ile Ile Ile Leu Val Ser Leu Val Cys Val Phe Leu Val Val Gly
          20                25             30

Tyr Val Tyr Pro Pro Arg Asp Ser Thr Ala Cys Tyr Ile Phe Ser Ser

```
                35                  40                  45
Ser Ser Cys Lys Lys Ile Ser Arg Trp Leu Pro Pro Glu Arg Glu
     50                  55                  60

Leu Ser Asp Lys Glu Ile Ala Ser Arg Val Val Thr Lys Asn Leu Leu
 65                  70                  75                  80

Asn Thr Pro Pro Ile Lys Thr Lys Asn Pro Lys Ile Ala Phe Met Phe
                 85                  90                  95

Leu Ser Pro Gly Ser Leu Ala Phe Glu Arg Leu Trp Asp Lys Phe Phe
                100                 105                 110

Gln Gly His Glu Gly Arg Phe Ser Ile His Ile His Ala Ser Arg Val
                115                 120                 125

Lys Pro Val His Ser Ser Arg Tyr Phe Gln Asn Arg Glu Ile Arg Ser
            130                 135                 140

Asp Lys Val Asp Trp Gly Lys Ile Ser Met Val Asp Ala Glu Lys Arg
145                 150                 155                 160

Leu Leu Ala Asn Ala Leu Lys Asp Pro Asp Asn Gln His Phe Val Leu
                165                 170                 175

Leu Ser Asp Ser Cys Val Pro Leu His Asn Phe Asp Tyr Ile Tyr Asn
                180                 185                 190

Tyr Leu Met Tyr Thr Asn Val Ser Phe Ile Asp Ser Phe Glu Asp Pro
            195                 200                 205

Gly Pro His Gly Ser Gly Arg Tyr Ser Asp His Met Leu Pro Glu Val
            210                 215                 220

Glu Lys Lys Phe Phe Arg Lys Gly Ala Gln Trp Phe Thr Met Lys Arg
225                 230                 235                 240

Gln His Ala Ile Ile Val Met Ala Asp Asn Leu Tyr Tyr Thr Lys Phe
                245                 250                 255

Arg Asp Tyr Cys Arg Pro Gly Met Asp Gly Arg Asn Cys Tyr Ala Asp
                260                 265                 270

Glu His Tyr Leu Pro Thr Phe Phe His Met Phe Asp Pro Thr Gly Ile
            275                 280                 285

Ala Asn Trp Ser Val Thr His Val Asp Trp Ser Glu Arg Lys Trp His
290                 295                 300

Pro Lys Ser Tyr Asp Leu Lys Asp Val Ser Tyr Gln Leu Ile Lys Asn
305                 310                 315                 320

Leu Ser Ser Ile Thr Glu Ser Val His Glu Thr Ser Asp Arg Lys Arg
                325                 330                 335

Val Thr Thr Val Thr Pro Cys Met Trp Asn Gly Met Asn Arg Pro Cys
                340                 345                 350

Tyr Leu Phe Ala Arg Lys Phe Leu Pro Glu Thr Leu Asp Thr Leu Ile
            355                 360                 365

Asp Leu Phe Pro Arg Tyr Thr Thr Ile
            370                 375
```

<210> SEQ ID NO 17
<211> LENGTH: 594
<212> TYPE: DNA
<213> ORGANISM: Helianthus annuus

<400> SEQUENCE: 17

| | | | | |
|---|---|---|---|---|
| atgatattat cgtttcgtgg acaagttgaa ttattggcaa acatccttta cggttgccgt | | | | 60 |
| gtcatacaga gggtattaga gcattcaacg gacgaagtac aaagccgatt catagtggac | | | | 120 |
| gagatcttgg agaatgttta tgttcttgca caagatcagt atggcaatta tgtaactcag | | | | 180 |

```
tatgtgttgg aggcggagaa accagaggtg agaagccaga tagtagacaa attgttgggc     240
catatagtgc gattaagcca acacaaatat gcctcaaatg ttgtcgaaaa atgtttggaa     300
tatggtgatg aagctataag aaaaatccta attgaagaga ttattgaatg tgctgatggc     360
aatgataact tattggtgtt ggtgaaagac caatatgcaa attatgtggt ccaaaaggtt     420
cttcaaatat gtagcgacca ccaacggaaa gtgttgctta gtcgtatgaa aggtcatctg     480
aatttgttga agacatatac ttatgggaaa catatcgttg ctcgctttga acaattgtat     540
ggtgaagaaa ttgcggcgtt gggttcaaac atgagcgatg gcaaatctgt atag          594
```

<210> SEQ ID NO 18
<211> LENGTH: 197
<212> TYPE: PRT
<213> ORGANISM: Helianthus annuus

<400> SEQUENCE: 18

```
Met Ile Leu Ser Phe Arg Gly Gln Val Glu Leu Leu Ala Lys His Pro
1               5                   10                  15

Tyr Gly Cys Arg Val Ile Gln Arg Val Leu Glu His Ser Thr Asp Glu
            20                  25                  30

Val Gln Ser Arg Phe Ile Val Asp Glu Ile Leu Glu Asn Val Tyr Val
        35                  40                  45

Leu Ala Gln Asp Gln Tyr Gly Asn Tyr Val Thr Gln Tyr Val Leu Glu
    50                  55                  60

Ala Glu Lys Pro Glu Val Arg Ser Gln Ile Val Asp Lys Leu Leu Gly
65                  70                  75                  80

His Ile Val Arg Leu Ser Gln His Lys Tyr Ala Ser Asn Val Val Glu
                85                  90                  95

Lys Cys Leu Glu Tyr Gly Asp Glu Ala Ile Arg Lys Ile Leu Ile Glu
            100                 105                 110

Glu Ile Ile Glu Cys Ala Asp Gly Asn Asp Asn Leu Leu Val Leu Val
        115                 120                 125

Lys Asp Gln Tyr Ala Asn Tyr Val Val Gln Lys Val Leu Gln Ile Cys
    130                 135                 140

Ser Asp His Gln Arg Lys Val Leu Leu Ser Arg Met Lys Gly His Leu
145                 150                 155                 160

Asn Leu Leu Lys Thr Tyr Thr Tyr Gly Lys His Ile Val Ala Arg Phe
                165                 170                 175

Glu Gln Leu Tyr Gly Glu Glu Ile Ala Ala Leu Gly Ser Asn Met Ser
            180                 185                 190

Asp Gly Lys Ser Val
        195
```

<210> SEQ ID NO 19
<211> LENGTH: 780
<212> TYPE: DNA
<213> ORGANISM: Helianthus annuus

<400> SEQUENCE: 19

```
atgaaccgga tgatcgaagc gtggaatgcg attccggatg tgccggagtc acattcttct      60
aaaggtgata tggcagaaga atctgatcat atacaaaatc caccaaaaac accttatata     120
atgagtaagc gaactacaac gagaagaaat tcgcttgaga atagcagcag gaaaactgtt     180
ccagccatgt tcagtaagct ggatcgcaag aaacccgtta atcagaaact cgacactgct     240
gaggttcata tgaaacacga acaaaacgg gccgttttta gtgaaatttc tgatgaaaag     300
```

```
atgcaagaat ctcgatataa tgaagataga tcgagttcca aagttgtggg gagcaatggc      360
ggattgaata ccaactctgt tgaacaagaa tccgaggact tatctttgat ccgcaatcaa      420
cttgctcaaa tcgagaccca acaatccaat ttatatgatc tcctcgagaa atttatcggg      480
agctcgctga acgggatgca atctctggag tctcgtgtgc gcggtgtaga gtcaacactc      540
gacgagattt catttgactt agcaaagtca actggacagg tgtcgaatcc ggaacccacc      600
ttgtgttgta agttaccagg tgcagatctt attagctcta aactctggaa gaaatcagaa      660
atccaacagt acccatctgt caagaacaag gatcttgaat cattcaactt tcaaaccacc      720
ggattccatc tccgtgccgg gctaattaag aacccattgg ccgaggtgca ccaaatatga      780
```

<210> SEQ ID NO 20
<211> LENGTH: 259
<212> TYPE: PRT
<213> ORGANISM: Helianthus annuus

<400> SEQUENCE: 20

```
Met Asn Arg Met Ile Glu Ala Trp Asn Ala Ile Pro Asp Val Pro Glu
1               5                   10                  15

Ser His Ser Ser Lys Gly Asp Met Ala Glu Glu Ser Asp His Ile Gln
            20                  25                  30

Asn Pro Pro Lys Thr Pro Tyr Ile Met Ser Lys Arg Thr Thr Thr Arg
        35                  40                  45

Arg Asn Ser Leu Glu Asn Ser Ser Arg Lys Thr Val Pro Ala Met Phe
    50                  55                  60

Ser Lys Leu Asp Arg Lys Lys Pro Val Asn Gln Lys Leu Asp Thr Ala
65                  70                  75                  80

Glu Val His Met Lys His Glu Thr Lys Arg Ala Val Phe Ser Glu Ile
                85                  90                  95

Ser Asp Glu Lys Met Gln Glu Ser Arg Tyr Asn Glu Asp Arg Ser Ser
            100                 105                 110

Ser Lys Val Val Gly Ser Asn Gly Gly Leu Asn Thr Asn Ser Val Glu
        115                 120                 125

Gln Glu Ser Glu Asp Leu Ser Leu Ile Arg Asn Gln Leu Ala Gln Ile
    130                 135                 140

Glu Thr Gln Gln Ser Asn Leu Tyr Asp Leu Leu Glu Lys Phe Ile Gly
145                 150                 155                 160

Ser Ser Leu Asn Gly Met Gln Ser Leu Glu Ser Arg Val Arg Gly Val
                165                 170                 175

Glu Ser Thr Leu Asp Glu Ile Ser Phe Asp Leu Ala Lys Ser Thr Gly
            180                 185                 190

Gln Val Ser Asn Pro Glu Pro Thr Leu Cys Cys Lys Leu Pro Gly Ala
        195                 200                 205

Asp Leu Ile Ser Ser Lys Leu Trp Lys Lys Ser Glu Ile Gln Gln Tyr
    210                 215                 220

Pro Ser Val Lys Asn Lys Asp Leu Glu Ser Phe Asn Phe Gln Thr Thr
225                 230                 235                 240

Gly Phe His Leu Arg Ala Gly Leu Ile Lys Asn Pro Leu Ala Glu Val
                245                 250                 255

His Gln Ile
```

<210> SEQ ID NO 21
<211> LENGTH: 915
<212> TYPE: DNA
<213> ORGANISM: Helianthus annuus -continued

```
<400> SEQUENCE: 21
atgcagaccg tttctcggag attagctcgt gaaaatttga gctctcgcac atcgatttac     60
tctctcaaat cgctttatcc tgtttccgat cgctgttacg gtgagtatga tcggcgttat    120
gcctctacgc ttaccaccaa aggtattgga catctggtcc gcaagggtac tggtggaaga    180
tcgtctgtta gtgggatagt tgctacagta ttcggagcta ctggtttcct gggcgttac     240 ttggtgcaac agcttgctaa aacgggttca caagtgctag taccatttag aggttccgaa    300
gattcgcccc gtcatctcaa actgatgggc gatttgggc agattgttcc catgaaatat    360
aatcctagag atgaaaactc aattaaggca gtcatggcca aggcaaatgt tgtgattaat    420
ctcataggaa gggaatatga aaccagaaat tatagttttg aggaagtgaa ccatcatatg    480
gctgaacaac ttgcaaagat tccaaagaa catggtggaa tcatgagatt tatacaactg    540
tcgtgtttag gtgcatctaa atcatctcca tctaggatgc ttcaagccaa ggctgctgca    600
gaagaatcca tcttacgtga attgcctgag gccacaatac tgcgacctgc agtgatggtt    660
ggtacagaag atcggatctt gaacccatgg gckcagatcg ctaaaaaata taactttctt    720
ccaatgatcg gggswgrytc tactaagatt cagccatggt atgttgctga tgtcgcctct    780
gcagttgttg cggcactaag tgatgacggg agtagcacgg aaaaagagta tgacactatg    840
gtgggcctga tagtttatac actgcatcaa ctggctgaac ttatgtatca aacgattcga    900
gaatggactc attga                                                      915

<210> SEQ ID NO 22
<211> LENGTH: 304
<212> TYPE: PRT
<213> ORGANISM: Helianthus annuus
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (245)..(246)
<223> OTHER INFORMATION: Xaa can be any naturally occurring amino acid

<400> SEQUENCE: 22

Met Gln Thr Val Ser Arg Arg Leu Ala Arg Glu Asn Leu Ser Ser Arg
1               5                   10                  15

Thr Ser Ile Tyr Ser Leu Lys Ser Leu Tyr Pro Val Ser Asp Arg Cys
            20                  25                  30

Tyr Gly Glu Tyr Asp Arg Arg Tyr Ala Ser Thr Leu Thr Thr Lys Gly
        35                  40                  45

Ile Gly His Leu Val Arg Lys Gly Thr Gly Gly Arg Ser Ser Val Ser
    50                  55                  60

Gly Ile Val Ala Thr Val Phe Gly Ala Thr Gly Phe Leu Gly Arg Tyr
65                  70                  75                  80

Leu Val Gln Gln Leu Ala Lys Thr Gly Ser Gln Val Leu Val Pro Phe
                85                  90                  95

Arg Gly Ser Glu Asp Ser Pro Arg His Leu Lys Leu Met Gly Asp Leu
            100                 105                 110

Gly Gln Ile Val Pro Met Lys Tyr Asn Pro Arg Asp Glu Asn Ser Ile
        115                 120                 125

Lys Ala Val Met Ala Lys Ala Asn Val Val Ile Asn Leu Ile Gly Arg
    130                 135                 140

Glu Tyr Glu Thr Arg Asn Tyr Ser Phe Glu Glu Val Asn His His Met
```

```
        145                 150                 155                 160
Ala Glu Gln Leu Ala Lys Ile Ser Lys Glu His Gly Gly Ile Met Arg
                165                 170                 175
Phe Ile Gln Leu Ser Cys Leu Gly Ala Ser Lys Ser Pro Ser Arg
            180                 185                 190
Met Leu Gln Ala Lys Ala Ala Glu Glu Ser Ile Leu Arg Glu Leu
            195                 200                 205
Pro Glu Ala Thr Ile Leu Arg Pro Ala Val Met Val Gly Thr Glu Asp
    210                 215                 220
Arg Ile Leu Asn Pro Trp Ala Gln Xaa Ala Lys Lys Tyr Asn Phe Leu
225                 230                 235                 240
Pro Met Ile Gly Xaa Xaa Ser Thr Lys Ile Gln Pro Trp Tyr Val Ala
                245                 250                 255
Asp Val Ala Ser Ala Val Val Ala Ala Leu Ser Asp Asp Gly Ser Ser
            260                 265                 270
Thr Glu Lys Glu Tyr Asp Thr Met Val Gly Leu Ile Val Tyr Thr Leu
            275                 280                 285
His Gln Leu Ala Glu Leu Met Tyr Gln Thr Ile Arg Glu Trp Thr His
    290                 295                 300
```

<210> SEQ ID NO 23
<211> LENGTH: 1521
<212> TYPE: DNA
<213> ORGANISM: Arabidopsis thaliana

<400> SEQUENCE: 23

```
atgaagatat actctagaac ggttgctgtt tcactcattg tgtcattcct cctgtgtttc      60
tctgcctttg ctgagcgcaa tgacgggacc ttcagagttg gactgaaaaa actcaagttg     120
gattcgaaaa atcggcttgc agcacgcgtc gaatccaagc aagaaaagcc cctgagagct     180
tacagacttg gagattctgg agatgctgat gttgttgtgc ttaagaatta tctagatgct     240
cagtactatg gtgagatcgc cattggtact ccacctcaga agttcactgt ggttttttgac    300
actgggagct ctaacctctg ggtgccatca tcaaaatgct atttctcact tgcatgtctc     360
ttgcatccca atacaagtc gtctcgttca agcacatatg agaagaatgg aaaagctgcc      420
gcaattcatt acggcactgg agcaattgct ggtttttta gtaatgatgc tgtcacagtt      480
ggcgatttag ttgtcaagga tcaggagttt atcgaggcaa ccaaggagcc tggtataaca     540
tttgttgtag ctaaatttga tggtatcctt ggtcttggat ccaagagat ctctgttgga      600
aaagctgctc ctgtttggta caacatgctc aagcaaggcc ttatcaagga gccggttttt    660
tcatttggc ttaaccgtaa tgcagatgaa gaagaaggtg gtgaacttgt atttggaggt      720
gttgatccaa atcatttcaa gggcaaacat acatatgttc ctgtgacaca aaagggctac     780
tggcagtttg acatgggtga tgttcttatt ggcggtgcac ccactgggtt ctgtgaaagt     840
ggctgttctg cgatagcaga ttctggtaca tctttgcttg ccggtccaac gactataatc     900
accatgataa accatgctat tggagcagct ggagttgtta ccagcagtg caagactgtt      960
gtggatcaat acgggcagac cattttggat ttacttttgt ctgagaccca accgaagaaa    1020
atctgctcgc agattggtct gtgtactttt gatggtaccc gtggtgtcag tatgggcatt    1080
gagtcggtgg tggacaagga aaacgccaaa ttgtctaatg tgttggaga tgctgcgtgt     1140
tctgcatgtg agatggctgt tgtgtggatc cagagccagt tgaggcaaaa catgactcaa    1200
gagcgcatat tgaactacgt caacgagcta tgtgaacgcc tccccagccc aatgggagag    1260
```

-continued

```
tctgcagttg actgtgcaca actgtcaaca atgcccactg tttcacttac cattggaggc    1320
aaagtatttg atcttgctcc agaagagtat gttctgaaag ttggtgaggg acctgtggca    1380
cagtgcatca gtggttttat tgctcttgac gttgctccac ctcgtggacc tctctggatc    1440
ttgggagatg tgttcatggg caaataccac accgtatttg actttggtaa cgaacaggtc    1500
gggtttgcag aggcagccta a                                               1521
```

<210> SEQ ID NO 24
<211> LENGTH: 506
<212> TYPE: PRT
<213> ORGANISM: Arabidopsis thaliana

<400> SEQUENCE: 24

```
Met Lys Ile Tyr Ser Arg Thr Val Ala Val Ser Leu Ile Val Ser Phe
1               5                   10                  15

Leu Leu Cys Phe Ser Ala Phe Ala Glu Arg Asn Asp Gly Thr Phe Arg
            20                  25                  30

Val Gly Leu Lys Lys Leu Lys Leu Asp Ser Lys Asn Arg Leu Ala Ala
        35                  40                  45

Arg Val Glu Ser Lys Gln Glu Lys Pro Leu Arg Ala Tyr Arg Leu Gly
    50                  55                  60

Asp Ser Gly Asp Ala Asp Val Val Leu Lys Asn Tyr Leu Asp Ala
65                  70                  75                  80

Gln Tyr Tyr Gly Glu Ile Ala Ile Gly Thr Pro Pro Gln Lys Phe Thr
                85                  90                  95

Val Val Phe Asp Thr Gly Ser Ser Asn Leu Trp Val Pro Ser Ser Lys
            100                 105                 110

Cys Tyr Phe Ser Leu Ala Cys Leu Leu His Pro Lys Tyr Lys Ser Ser
        115                 120                 125

Arg Ser Ser Thr Tyr Glu Lys Asn Gly Lys Ala Ala Ala Ile His Tyr
    130                 135                 140

Gly Thr Gly Ala Ile Ala Gly Phe Phe Ser Asn Asp Ala Val Thr Val
145                 150                 155                 160

Gly Asp Leu Val Val Lys Asp Gln Glu Phe Ile Glu Ala Thr Lys Glu
                165                 170                 175

Pro Gly Ile Thr Phe Val Val Ala Lys Phe Asp Gly Ile Leu Gly Leu
            180                 185                 190

Gly Phe Gln Glu Ile Ser Val Gly Lys Ala Ala Pro Val Trp Tyr Asn
        195                 200                 205

Met Leu Lys Gln Gly Leu Ile Lys Glu Pro Val Phe Ser Phe Trp Leu
    210                 215                 220

Asn Arg Asn Ala Asp Glu Glu Gly Glu Leu Val Phe Gly Gly
225                 230                 235                 240

Val Asp Pro Asn His Phe Lys Gly Lys His Thr Tyr Val Pro Val Thr
                245                 250                 255

Gln Lys Gly Tyr Trp Gln Phe Asp Met Gly Asp Val Leu Ile Gly Gly
            260                 265                 270

Ala Pro Thr Gly Phe Cys Glu Ser Gly Cys Ser Ala Ile Ala Asp Ser
        275                 280                 285

Gly Thr Ser Leu Leu Ala Gly Pro Thr Thr Ile Ile Thr Met Ile Asn
    290                 295                 300

His Ala Ile Gly Ala Ala Gly Val Val Ser Gln Gln Cys Lys Thr Val
305                 310                 315                 320

Val Asp Gln Tyr Gly Gln Thr Ile Leu Asp Leu Leu Leu Ser Glu Thr
```

-continued

```
                325                 330                 335
Gln Pro Lys Lys Ile Cys Ser Gln Ile Gly Leu Cys Thr Phe Asp Gly
            340                 345                 350
Thr Arg Gly Val Ser Met Gly Ile Glu Ser Val Val Asp Lys Glu Asn
        355                 360                 365
Ala Lys Leu Ser Asn Gly Val Gly Asp Ala Ala Cys Ser Ala Cys Glu
    370                 375                 380
Met Ala Val Val Trp Ile Gln Ser Gln Leu Arg Gln Asn Met Thr Gln
385                 390                 395                 400
Glu Arg Ile Leu Asn Tyr Val Asn Glu Leu Cys Glu Arg Leu Pro Ser
                405                 410                 415
Pro Met Gly Glu Ser Ala Val Asp Cys Ala Gln Leu Ser Thr Met Pro
            420                 425                 430
Thr Val Ser Leu Thr Ile Gly Gly Lys Val Phe Asp Leu Ala Pro Glu
        435                 440                 445
Glu Tyr Val Leu Lys Val Gly Glu Gly Pro Val Ala Gln Cys Ile Ser
    450                 455                 460
Gly Phe Ile Ala Leu Asp Val Ala Pro Pro Arg Gly Pro Leu Trp Ile
465                 470                 475                 480
Leu Gly Asp Val Phe Met Gly Lys Tyr His Thr Val Phe Asp Phe Gly
                485                 490                 495
Asn Glu Gln Val Gly Phe Ala Glu Ala Ala
            500                 505
```

<210> SEQ ID NO 25
<211> LENGTH: 1542
<212> TYPE: DNA
<213> ORGANISM: Arabidopsis thaliana

<400> SEQUENCE: 25

| | | | | | |
|---|---|---|---|---|---|
| atgggagtat | actcgagagc | ggttgcgttt | tcgggctttg | tgtcgtttct | gctgtttttc | 60 |
| actgcttatt | ctaagagaaa | tgatggaaca | ttcagagttg | gcctgaaaaa | actgaagttg | 120 |
| gatcctaaca | accgactcgc | aacacgcttt | ggttccaagc | aagaagaggc | cttgagatct | 180 |
| tctttgcgtt | cgtacaacaa | caatcttggt | ggtgattctg | gagatgctga | tattgtcccg | 240 |
| ctcaagaatt | acttggatgc | tcagtactat | ggtgagattc | tattggtac | tccaccgcag | 300 |
| aagttcactg | tcattttga | taccggaagc | tctaaccttt | gggtgccatc | aggaaaatgt | 360 |
| tttttctcgc | tgtcttgtta | ctttcatgct | aagtacaagt | cctcgcgatc | aagcacatat | 420 |
| aagaagagtg | aaaacgtgc | cgcaatccat | tacggctcag | gatcaatctc | tggtttcttt | 480 |
| agttatgatg | ctgtcacggt | tggtgatttg | gttgtcaaag | atcaggagtt | tattgagaca | 540 |
| accagtgagc | tggtttaac | attcctggtg | gctaagtttg | atggtcttct | tggtcttggg | 600 |
| ttccaagaga | tcgctgttgg | aaacgctact | cctgtttggt | acaatatgct | caagcaaggc | 660 |
| cttataaaga | ggccggtctt | tcattttgg | cttaaccgtg | atccaaagag | tgaagaaggc | 720 |
| ggtgaaatcg | tattcggagg | tgttgatcca | aagcatttta | gaggagaaca | tacatttgtt | 780 |
| cctgtgacac | aaaggggtta | ctggcagttc | gacatgggtg | aggttctcat | tgccggtgaa | 840 |
| tctactggat | attgtggaag | tggttgttct | gcgatagcag | attctggaac | atcgttactt | 900 |
| gcgggtccaa | cggctgtggt | tgccatgata | aataaggcta | ttggagcatc | tggagttgtt | 960 |
| agccagcagt | gcaagactgt | tgttgaccag | tatggacaaa | ccattttgga | tttacttttg | 1020 |
| gctgagactc | aaccaaagaa | gatttgctca | caaattggtc | tttgcgctta | cgatggcacc | 1080 |

```
catgggtca gtatggggat tgaatcggtg gtggacaagg aaaacacaag atcatctagt    1140
ggtcttcgag acgcggttg tcctgcatgt gaaatggcgg ttgtgtggat acagagccaa    1200
ttgaggcaga acatgactca agagaggata gtgaactaca ttaatgagat atgcgagcgc    1260
atgcctagtc caaatggaga gtctgctgtt gactgctcac aactttctaa aatgcctact    1320
gtttcattca ccattggaga caaagtcttt gatcttgctc ccgaagagta cgtactgaag    1380
attggggaag gaccagtggc acaatgtatt agcggcttta ccgcacttga tatccctcca    1440
cctcgtggac ctctctggat acttggagat gtgtttatgg gaaaatacca cactgtcttt    1500
gacttcggaa acgagcaggt tggcttcgca gaagccgtgt ga                      1542
```

<210> SEQ ID NO 26
<211> LENGTH: 513
<212> TYPE: PRT
<213> ORGANISM: Arabidopsis thaliana

<400> SEQUENCE: 26

```
Met Gly Val Tyr Ser Arg Ala Val Ala Phe Ser Gly Phe Val Ser Phe
1               5                   10                  15

Leu Leu Phe Phe Thr Ala Tyr Ser Lys Arg Asn Asp Gly Thr Phe Arg
            20                  25                  30

Val Gly Leu Lys Lys Leu Lys Leu Asp Pro Asn Asn Arg Leu Ala Thr
        35                  40                  45

Arg Phe Gly Ser Lys Gln Glu Glu Ala Leu Arg Ser Ser Leu Arg Ser
    50                  55                  60

Tyr Asn Asn Asn Leu Gly Gly Asp Ser Gly Asp Ala Asp Ile Val Pro
65                  70                  75                  80

Leu Lys Asn Tyr Leu Asp Ala Gln Tyr Tyr Gly Glu Ile Ala Ile Gly
                85                  90                  95

Thr Pro Pro Gln Lys Phe Thr Val Ile Phe Asp Thr Gly Ser Ser Asn
            100                 105                 110

Leu Trp Val Pro Ser Gly Lys Cys Phe Phe Ser Leu Ser Cys Tyr Phe
        115                 120                 125

His Ala Lys Tyr Lys Ser Ser Arg Ser Ser Thr Tyr Lys Lys Ser Gly
    130                 135                 140

Lys Arg Ala Ala Ile His Tyr Gly Ser Gly Ser Ile Ser Gly Phe Phe
145                 150                 155                 160

Ser Tyr Asp Ala Val Thr Val Gly Asp Leu Val Val Lys Asp Gln Glu
                165                 170                 175

Phe Ile Glu Thr Thr Ser Glu Pro Gly Leu Thr Phe Leu Val Ala Lys
            180                 185                 190

Phe Asp Gly Leu Leu Gly Leu Gly Phe Gln Glu Ile Ala Val Gly Asn
        195                 200                 205

Ala Thr Pro Val Trp Tyr Asn Met Leu Lys Gln Gly Leu Ile Lys Arg
    210                 215                 220

Pro Val Phe Ser Phe Trp Leu Asn Arg Asp Pro Lys Ser Glu Glu Gly
225                 230                 235                 240

Gly Glu Ile Val Phe Gly Gly Val Asp Pro Lys His Phe Arg Gly Glu
                245                 250                 255

His Thr Phe Val Pro Val Thr Gln Arg Gly Tyr Trp Gln Phe Asp Met
            260                 265                 270

Gly Glu Val Leu Ile Ala Gly Glu Ser Thr Gly Tyr Cys Gly Ser Gly
        275                 280                 285

Cys Ser Ala Ile Ala Asp Ser Gly Thr Ser Leu Leu Ala Gly Pro Thr
```

```
                        290                     295                     300
Ala Val Val Ala Met Ile Asn Lys Ala Ile Gly Ala Ser Gly Val Val
305                     310                     315                     320
Ser Gln Gln Cys Lys Thr Val Val Asp Gln Tyr Gly Gln Thr Ile Leu
                325                     330                     335
Asp Leu Leu Leu Ala Glu Thr Gln Pro Lys Lys Ile Cys Ser Gln Ile
                340                     345                     350
Gly Leu Cys Ala Tyr Asp Gly Thr His Gly Val Ser Met Gly Ile Glu
                355                     360                     365
Ser Val Val Asp Lys Glu Asn Thr Arg Ser Ser Gly Leu Arg Asp
370                     375                     380
Ala Gly Cys Pro Ala Cys Glu Met Ala Val Val Trp Ile Gln Ser Gln
385                     390                     395                     400
Leu Arg Gln Asn Met Thr Gln Glu Arg Ile Val Asn Tyr Ile Asn Glu
                405                     410                     415
Ile Cys Glu Arg Met Pro Ser Pro Asn Gly Glu Ser Ala Val Asp Cys
                420                     425                     430
Ser Gln Leu Ser Lys Met Pro Thr Val Ser Phe Thr Ile Gly Asp Lys
                435                     440                     445
Val Phe Asp Leu Ala Pro Glu Glu Tyr Val Leu Lys Ile Gly Glu Gly
        450                     455                     460
Pro Val Ala Gln Cys Ile Ser Gly Phe Thr Ala Leu Asp Ile Pro Pro
465                     470                     475                     480
Pro Arg Gly Pro Leu Trp Ile Leu Gly Asp Val Phe Met Gly Lys Tyr
                485                     490                     495
His Thr Val Phe Asp Phe Gly Asn Glu Gln Val Gly Phe Ala Glu Ala
                500                     505                     510
Val

<210> SEQ ID NO 27
<211> LENGTH: 1527
<212> TYPE: DNA
<213> ORGANISM: Arabidopsis thaliana

<400> SEQUENCE: 27
atgggaacta ggttccaatc attcttgctc gtgttcttgc tttcatgttt aatcctcata    60
tcaactgcct cgtgtgagcg aaatggtgat ggaacgatta gaattggatt gaagaagagg   120
aaactagacc ggagcaacag gctagcttct cagctttttt tgaaaaaccg agggtctcat   180
tggtctccca aacactattt tcgcctgaac gatgaaaatg cggatatggt tccgctgaaa   240
aactatttgg atgctcaata ctatggtgac attaccattg gtactcctcc tcagaagttc   300
actgtgatct tgatactgg tagctccaat ctctggatac catctactaa atgttaccta   360
tcggttgctt gttatttcca ctccaagtac aaggctagcc agtcatcgtc atatagaaag   420
aacggaaaac ccgcgtctat ccgctatggg acgggtgcta tttctggtta ctttagcaat   480
gatgatgtta agttggtga tattgttgtg aaagagcagg aattcataga ggctactagt   540
gagcctggta acattcttg ctagcaaag tttgatggta tcctcggttt gggtttcaaa   600
gagatttctg taggaaactc aactccggtt tggtataaca tggtagaaaa aggtttagtt   660
aaggaaccga ttttttcgtt ctggcttaac cgtaacccga agatccaga aggcggtgag   720
attgttttcg gtggagtcga cccgaagcac ttcaaaggag agcatacttt tgttcctgtg   780
acacataaag gttactggca gtttgacatg ggtgatctcc aaattgctgg caaaccaacc   840
```

```
ggatattgtg ctaaaggttg ttctgctatt gctgattccg gaacttctct gctcaccggt    900
ccatcgactg tcatcacgat gatcaatcac gcgataggag cacaaggaat tgtaagccgt    960
gaatgcaagg ccgtggtgga tcaatacgga aaaccatgt tgaattctct tctagctcag    1020
gaggatccga agaaagtatg ctcacaaatt ggagtctgcg cttatgatgg tacacagagt   1080
gtgagtatgg ggatccggtc agttgtagac gatggaacat cgggtctttt aaaccaagcg   1140
atgtgcagtg cttgcgaaat ggcagccgtg tggatggaga gcgaattgac tcagaatcaa   1200
acacaagaac gcatactcgc ttatgctgct gagctatgtg accatatacc aacccaaaac   1260
caacaatcag cagtggactg tgggagggtt cgtcgatgc ctatagtcac attctcaatt    1320
ggtggcagaa gctttgatct aactcctcaa gaccatatat tcaagatcgg ggaaggagtt   1380
gagtctcagt gcaccagcgg tttcacggca atggatattg ctccgcctcg tggacctctc   1440
tggatcttgg gtgatatctt catgggacca taccacacag tgttcgatta tgggaaagga   1500
agagttggat tcgccaaagc tgcttaa                                       1527
```

<210> SEQ ID NO 28
<211> LENGTH: 508
<212> TYPE: PRT
<213> ORGANISM: Arabidopsis thaliana

<400> SEQUENCE: 28

```
Met Gly Thr Arg Phe Gln Ser Phe Leu Leu Val Phe Leu Leu Ser Cys
1               5                   10                  15

Leu Ile Leu Ile Ser Thr Ala Ser Cys Glu Arg Asn Gly Asp Gly Thr
            20                  25                  30

Ile Arg Ile Gly Leu Lys Lys Arg Lys Leu Asp Arg Ser Asn Arg Leu
        35                  40                  45

Ala Ser Gln Leu Phe Leu Lys Asn Arg Gly Ser His Trp Ser Pro Lys
    50                  55                  60

His Tyr Phe Arg Leu Asn Asp Glu Asn Ala Asp Met Val Pro Leu Lys
65                  70                  75                  80

Asn Tyr Leu Asp Ala Gln Tyr Tyr Gly Asp Ile Thr Ile Gly Thr Pro
                85                  90                  95

Pro Gln Lys Phe Thr Val Ile Phe Asp Thr Gly Ser Ser Asn Leu Trp
            100                 105                 110

Ile Pro Ser Thr Lys Cys Tyr Leu Ser Val Ala Cys Tyr Phe His Ser
        115                 120                 125

Lys Tyr Lys Ala Ser Gln Ser Ser Ser Tyr Arg Lys Asn Gly Lys Pro
    130                 135                 140

Ala Ser Ile Arg Tyr Gly Thr Gly Ala Ile Ser Gly Tyr Phe Ser Asn
145                 150                 155                 160

Asp Asp Val Lys Val Gly Asp Ile Val Val Lys Glu Gln Glu Phe Ile
                165                 170                 175

Glu Ala Thr Ser Glu Pro Gly Ile Thr Phe Leu Leu Ala Lys Phe Asp
            180                 185                 190

Gly Ile Leu Gly Leu Gly Phe Lys Glu Ile Ser Val Gly Asn Ser Thr
        195                 200                 205

Pro Val Trp Tyr Asn Met Val Glu Lys Gly Leu Val Lys Glu Pro Ile
    210                 215                 220

Phe Ser Phe Trp Leu Asn Arg Asn Pro Lys Asp Pro Glu Gly Gly Glu
225                 230                 235                 240

Ile Val Phe Gly Gly Val Asp Pro Lys His Phe Lys Gly Glu His Thr
                245                 250                 255
```

Phe Val Pro Val Thr His Lys Gly Tyr Trp Gln Phe Asp Met Gly Asp
            260                 265                 270

Leu Gln Ile Ala Gly Lys Pro Thr Gly Tyr Cys Ala Lys Gly Cys Ser
        275                 280                 285

Ala Ile Ala Asp Ser Gly Thr Ser Leu Leu Thr Gly Pro Ser Thr Val
    290                 295                 300

Ile Thr Met Ile Asn His Ala Ile Gly Ala Gln Gly Ile Val Ser Arg
305                 310                 315                 320

Glu Cys Lys Ala Val Val Asp Gln Tyr Gly Lys Thr Met Leu Asn Ser
                325                 330                 335

Leu Leu Ala Gln Glu Asp Pro Lys Lys Val Cys Ser Gln Ile Gly Val
            340                 345                 350

Cys Ala Tyr Asp Gly Thr Gln Ser Val Ser Met Gly Ile Arg Ser Val
        355                 360                 365

Val Asp Asp Gly Thr Ser Gly Leu Leu Asn Gln Ala Met Cys Ser Ala
    370                 375                 380

Cys Glu Met Ala Ala Val Trp Met Glu Ser Glu Leu Thr Gln Asn Gln
385                 390                 395                 400

Thr Gln Glu Arg Ile Leu Ala Tyr Ala Ala Glu Leu Cys Asp His Ile
                405                 410                 415

Pro Thr Gln Asn Gln Gln Ser Ala Val Asp Cys Gly Arg Val Ser Ser
            420                 425                 430

Met Pro Ile Val Thr Phe Ser Ile Gly Gly Arg Ser Phe Asp Leu Thr
        435                 440                 445

Pro Gln Asp His Ile Phe Lys Ile Gly Glu Gly Val Glu Ser Gln Cys
    450                 455                 460

Thr Ser Gly Phe Thr Ala Met Asp Ile Ala Pro Arg Gly Pro Leu
465                 470                 475                 480

Trp Ile Leu Gly Asp Ile Phe Met Gly Pro Tyr His Thr Val Phe Asp
                485                 490                 495

Tyr Gly Lys Gly Arg Val Gly Phe Ala Lys Ala Ala
            500                 505

<210> SEQ ID NO 29
<211> LENGTH: 951
<212> TYPE: DNA
<213> ORGANISM: Arabidopsis thaliana

<400> SEQUENCE: 29
atggagaaag gtttgacgat gtcttgtgtt ttggtggtgg ttgcattctt agccatggtt      60
catgtctctg tttcagttcc gttcgtagtg tttcctgaaa tcggaacaca atgttctgat     120
gctccaaatg ctaacttcac acagcttctc agtaacctct ctagctcacc tggcttttgc     180
atagaaattg gcgagggaaa tccaataggc gcttcatggt taataccact acacaacaa     240
gcggaagtag cgtgtgataa ggtgacgcag atggaagagt tgagtcaagg atacaacatt     300
gttggaagag ctcaggggag cttagtggct cgaggcttaa tcgagttctg cgaaggtggg     360
cctcctgttc acaactatat atccttggct ggtcctcatg ctggcaccgc cgatcttctt     420
cggtgtaata cttctggctt aatttgtgac atagcaaatg ggataggcaa ggaaaatccc     480
tacagcgact tgttcaaga taatcttgct cctagtggtt atttcaaaaa ccctaaaaat     540
gtgacagggt acctgaaaga ctgtcagtat ctacctaagc ttaacaatga gagaccatac     600
gaaagaaaca caacttacaa agaccgtttc gcaagtttac agaaccctggt ttttgtcctg     660

-continued

```
tttgagaacg atacggttat tgttccaaaa gagtcatctt ggttcgggtt ttatccggat    720
ggtgacttaa cacatgttct ccctgttcaa gagacaaagc tctatataga agattggata    780
ggtctgaaag cattggttgt tgctggaaaa gtgcagtttg tgaatgtaac cggtgaccac    840
ttaataatgg cggacgaaga tctcgtcaaa tacgtcgtac ctcttctcca ggatcaacag    900
tctgccccac caagactcaa ccgcaagacc aaggagccct gcatccttaa              951
```

<210> SEQ ID NO 30
<211> LENGTH: 316
<212> TYPE: PRT
<213> ORGANISM: Arabidopsis thaliana

<400> SEQUENCE: 30

```
Met Glu Lys Gly Leu Thr Met Ser Cys Val Leu Val Val Ala Phe
1               5                   10                  15

Leu Ala Met Val His Val Ser Val Ser Val Pro Phe Val Val Phe Pro
                20                  25                  30

Glu Ile Gly Thr Gln Cys Ser Asp Ala Pro Asn Ala Asn Phe Thr Gln
            35                  40                  45

Leu Leu Ser Asn Leu Ser Ser Pro Gly Phe Cys Ile Glu Ile Gly
        50                  55                  60

Glu Gly Asn Pro Ile Gly Ala Ser Trp Leu Ile Pro Leu Thr Gln Gln
65                  70                  75                  80

Ala Glu Val Ala Cys Asp Lys Val Thr Gln Met Glu Glu Leu Ser Gln
                85                  90                  95

Gly Tyr Asn Ile Val Gly Arg Ala Gln Gly Ser Leu Val Ala Arg Gly
            100                 105                 110

Leu Ile Glu Phe Cys Glu Gly Gly Pro Pro Val His Asn Tyr Ile Ser
        115                 120                 125

Leu Ala Gly Pro His Ala Gly Thr Ala Asp Leu Leu Arg Cys Asn Thr
    130                 135                 140

Ser Gly Leu Ile Cys Asp Ile Ala Asn Gly Ile Gly Lys Glu Asn Pro
145                 150                 155                 160

Tyr Ser Asp Phe Val Gln Asp Asn Leu Ala Pro Ser Gly Tyr Phe Lys
                165                 170                 175

Asn Pro Lys Asn Val Thr Gly Tyr Leu Lys Asp Cys Gln Tyr Leu Pro
            180                 185                 190

Lys Leu Asn Asn Glu Arg Pro Tyr Glu Arg Asn Thr Thr Tyr Lys Asp
        195                 200                 205

Arg Phe Ala Ser Leu Gln Asn Leu Val Phe Val Leu Phe Glu Asn Asp
    210                 215                 220

Thr Val Ile Val Pro Lys Glu Ser Ser Trp Phe Gly Phe Tyr Pro Asp
225                 230                 235                 240

Gly Asp Leu Thr His Val Leu Pro Val Gln Glu Thr Lys Leu Tyr Ile
                245                 250                 255

Glu Asp Trp Ile Gly Leu Lys Ala Leu Val Val Ala Gly Lys Val Gln
            260                 265                 270

Phe Val Asn Val Thr Gly Asp His Leu Ile Met Ala Asp Glu Asp Leu
        275                 280                 285

Val Lys Tyr Val Pro Leu Leu Gln Asp Gln Gln Ser Ala Pro Pro
    290                 295                 300

Arg Leu Asn Arg Lys Thr Lys Glu Pro Leu His Pro
305                 310                 315
```

<210> SEQ ID NO 31
<211> LENGTH: 1473
<212> TYPE: DNA
<213> ORGANISM: Arabidopsis thaliana

<400> SEQUENCE: 31

| | | |
|---|---|---|
| atgcattggc atggtgtaga gcagccgaga atccgtggt cagatggtcc tgaatacatc | 60 |
| acacaatgcc cgattcgacc cgggtcagat tttttgtaca agtcatatt ttccatcgaa | 120 |
| gacacgactg tttggtggca cgcgcatagc tcttggacac gtgcaactgt acacggtctt | 180 |
| attttcgtat atcctcgccc cccgcaaatc ctccctttc caaaggcaga ccatgaagtc | 240 |
| cccataattt tgggtgagtg gtggaagagg gatgtgagag aggtcgttga ggagttcgta | 300 |
| aggacaggag gggctcctaa tgtgtccgat gctttgacca tcaatggaca tcctggtttc | 360 |
| ttgtatcctt gctctaaatc agatacattt catctcacgg tagagaaggg gaaaacctac | 420 |
| cgcattcgga tggtaaatgc cgcaatgaac ctacctctct ttttcgcaat cgcgaaccac | 480 |
| agcctcaccg tagtctcggc cgatggacac tacatcaaac ctataaaggc tacttatatc | 540 |
| actatatccc ctggcgaaac actagacatg ttattacacg ctgaccaaga ccccgaacgc | 600 |
| acttattaca tggctgccag agcttaccaa agcggaaata tcgatttcaa caactccact | 660 |
| accataggaa tcttaagtta cacctcttca tgcaaagcta aaacatcatc gttttcagga | 720 |
| tattacccaa cccttccttt ttacaatgac acctcagcag cttttggatt ctttaccaag | 780 |
| atcaaatgct tattctccgg tcaagttcct gtccaaatct ctcgtaggat aatcacgacg | 840 |
| gtttcaataa atcttcgcat gtgtcctcaa aactcgtgcg aaggtccaaa tgggtcgaga | 900 |
| ttagcagcga gtatgaacaa catatcgttt gtcacaccaa gtcacgtgga catactaaaa | 960 |
| gcttattact atcacattaa aggcgtttat ggaacgcggt ttccggagtt tccaccgttg | 1020 |
| atttttaatt tcaccgcaga aaatcagcca ttgttttttgg aaactccgag actcgcaacc | 1080 |
| gaggtaaagg tgattgagtt cggtcaagtg gttgagcttg ttattcaagg gactagtttg | 1140 |
| gttggtggtg gactcgatca tcctatgcat ctccatggtt ttagcttcta tgtggttgga | 1200 |
| gtagggttcg ggaactataa cataagtgaa gaagatccgt cgtcgagata taatctctac | 1260 |
| gatccaccgt ataaaaatac aatgaccgtg cctaggaatg gttggatcgc tatcagattc | 1320 |
| gtagctgata atccccgggggt ttggttcatg cactgtcact ggatagaca tcaaacgtgg | 1380 |
| ggtatgaatg ttgtgttcat tgttaagaat ggtagagagc caaatcagca gattctgcct | 1440 |
| ccaccagatg atttgccgcc ttgctatgaa taa | 1473 |

<210> SEQ ID NO 32
<211> LENGTH: 490
<212> TYPE: PRT
<213> ORGANISM: Arabidopsis thaliana

<400> SEQUENCE: 32

Met His Trp His Gly Val Glu Gln Pro Arg Asn Pro Trp Ser Asp Gly
1               5                   10                  15

Pro Glu Tyr Ile Thr Gln Cys Pro Ile Arg Pro Gly Ser Asp Phe Leu
            20                  25                  30

Tyr Lys Val Ile Phe Ser Ile Glu Asp Thr Thr Val Trp Trp His Ala
        35                  40                  45

His Ser Ser Trp Thr Arg Ala Thr Val His Gly Leu Ile Phe Val Tyr
    50                  55                  60

Pro Arg Pro Pro Gln Ile Leu Pro Phe Pro Lys Ala Asp His Glu Val
65                  70                  75                  80

-continued

```
Pro Ile Ile Leu Gly Glu Trp Trp Lys Arg Asp Val Arg Glu Val Val
                 85                  90                  95

Glu Glu Phe Val Arg Thr Gly Gly Ala Pro Asn Val Ser Asp Ala Leu
            100                 105                 110

Thr Ile Asn Gly His Pro Gly Phe Leu Tyr Pro Cys Ser Lys Ser Asp
        115                 120                 125

Thr Phe His Leu Thr Val Glu Lys Gly Lys Thr Tyr Arg Ile Arg Met
    130                 135                 140

Val Asn Ala Ala Met Asn Leu Pro Leu Phe Phe Ala Ile Ala Asn His
145                 150                 155                 160

Ser Leu Thr Val Val Ser Ala Asp Gly His Tyr Ile Lys Pro Ile Lys
                165                 170                 175

Ala Thr Tyr Ile Thr Ile Ser Pro Gly Glu Thr Leu Asp Met Leu Leu
            180                 185                 190

His Ala Asp Gln Asp Pro Glu Arg Thr Tyr Tyr Met Ala Ala Arg Ala
        195                 200                 205

Tyr Gln Ser Gly Asn Ile Asp Phe Asn Asn Ser Thr Thr Ile Gly Ile
    210                 215                 220

Leu Ser Tyr Thr Ser Ser Cys Lys Ala Lys Thr Ser Ser Phe Ser Gly
225                 230                 235                 240

Tyr Tyr Pro Thr Leu Pro Phe Tyr Asn Asp Thr Ser Ala Ala Phe Gly
                245                 250                 255

Phe Phe Thr Lys Ile Lys Cys Leu Phe Ser Gly Gln Val Pro Val Gln
            260                 265                 270

Ile Ser Arg Arg Ile Ile Thr Thr Val Ser Ile Asn Leu Arg Met Cys
    275                 280                 285

Pro Gln Asn Ser Cys Glu Gly Pro Asn Gly Ser Arg Leu Ala Ala Ser
290                 295                 300

Met Asn Asn Ile Ser Phe Val Thr Pro Ser His Val Asp Ile Leu Lys
305                 310                 315                 320

Ala Tyr Tyr His Ile Lys Gly Val Tyr Gly Thr Arg Phe Pro Glu
                325                 330                 335

Phe Pro Pro Leu Ile Phe Asn Phe Thr Ala Glu Asn Gln Pro Leu Phe
            340                 345                 350

Leu Glu Thr Pro Arg Leu Ala Thr Glu Val Lys Val Ile Glu Phe Gly
    355                 360                 365

Gln Val Val Glu Leu Val Ile Gln Gly Thr Ser Leu Val Gly Gly Gly
370                 375                 380

Leu Asp His Pro Met His Leu His Gly Phe Ser Phe Tyr Val Val Gly
385                 390                 395                 400

Val Gly Phe Gly Asn Tyr Asn Ile Ser Glu Glu Asp Pro Ser Ser Arg
                405                 410                 415

Tyr Asn Leu Tyr Asp Pro Pro Tyr Lys Asn Thr Met Thr Val Pro Arg
            420                 425                 430

Asn Gly Trp Ile Ala Ile Arg Phe Val Ala Asp Asn Pro Gly Val Trp
    435                 440                 445

Phe Met His Cys His Leu Asp Arg His Gln Thr Trp Gly Met Asn Val
450                 455                 460

Val Phe Ile Val Lys Asn Gly Arg Glu Pro Asn Gln Gln Ile Leu Pro
465                 470                 475                 480

Pro Pro Asp Asp Leu Pro Pro Cys Tyr Glu
                485                 490
```

<210> SEQ ID NO 33
<211> LENGTH: 1470
<212> TYPE: DNA
<213> ORGANISM: Arabidopsis thaliana

<400> SEQUENCE: 33

| | | | | | |
|---|---|---|---|---|---|
| atgtctgctt | ctgattcctc | ttcctctctt | cccgttactc | ttgacaccat | caaccccaag | 60 |
| gttatcaaat | gtgagtatgc | tgtccgtgga | gaaattgtca | acattgctca | gaaattgcaa | 120 |
| gaagatttga | agactaacaa | ggacgcttat | ccctttgatg | agattatcta | ctgtaatatc | 180 |
| gggaatcctc | aatctcttgg | tcaacagcct | ataacattct | tcagagaggt | tcttgcttta | 240 |
| tgttcctaca | cagccctgtt | ggatgagagt | gcaacacacg | gtttgttcag | ttctgattcg | 300 |
| attgagcgtg | cttggaagat | tctggaccaa | attcccggga | gagcgactgg | tgcttacagc | 360 |
| cacagccagg | gtatcaaggg | gttacgtgat | gcaattgctg | atggaatcga | agcccgtgat | 420 |
| ggtttccctg | ctgatcctaa | tgatatattc | atgacagatg | gtgcaagtcc | aggggttcat | 480 |
| atgatgatgc | aacttctcat | aacttcagag | aaagatggaa | tcctttgtcc | tattcctcag | 540 |
| tatccattgt | actcagcttc | aattgccctt | acggtggaa | ctttggttcc | atactacctt | 600 |
| gatgaagcat | caggatgggg | tcttgaaata | tctgagctga | agaaacaact | tgaagatgct | 660 |
| aggtcaaagg | gcatcactgt | gagagctttg | gctgtcatta | accctggaaa | cccgacaggg | 720 |
| caggttcttt | cggaagaaaa | ccagcgtgac | gttgttaagt | tctgcaagca | agagggttta | 780 |
| gttcttttag | cagacgaggt | ttatcaagag | aatgtctatg | tccctgacaa | aaagttccat | 840 |
| tccttcaaga | agtagcccg | ctctatgggc | tacggtgaga | aggatcttgc | cttagtctct | 900 |
| ttccaatctg | tctccaaagg | gtactatgga | gagtgtggga | aaagaggtgg | ttacatggag | 960 |
| gttactggat | tcacttctga | tgtaagagag | cagatataca | aaatggcttc | tgtgaatctt | 1020 |
| tgttccaaca | tctctggtca | aattcttgct | agcctcatca | tgagcccacc | caagcctggt | 1080 |
| gacgactcct | atgaatcata | catagcagag | aaggatggaa | ttctctcatc | tttggcaaga | 1140 |
| cgtgcaaaga | ctcttgaaga | ggctctgaac | aagctagagg | gagttacatg | caatagagca | 1200 |
| gaaggagcta | tgtatctatt | cccttgcctt | caccttccac | aaaaggcaat | tgcagctgct | 1260 |
| gaggcggaaa | agacagcacc | agacaatttc | tactgcaaac | gccttctaaa | agctactgga | 1320 |
| atagtcgttg | tccctggttc | tggctttaga | caggtacctg | aacatggca | tttcaggtgc | 1380 |
| actatacttc | cccaagagga | taagattcca | gcgattgttg | atcgtctaac | tgcgttccac | 1440 |
| cagagcttca | tggacgagtt | ccgcgactaa | | | | 1470 |

<210> SEQ ID NO 34
<211> LENGTH: 489
<212> TYPE: PRT
<213> ORGANISM: Arabidopsis thaliana

<400> SEQUENCE: 34

Met Ser Ala Ser Asp Ser Ser Ser Leu Pro Val Thr Leu Asp Thr
1               5                   10                  15

Ile Asn Pro Lys Val Ile Lys Cys Glu Tyr Ala Val Arg Gly Glu Ile
                20                  25                  30

Val Asn Ile Ala Gln Lys Leu Gln Glu Asp Leu Lys Thr Asn Lys Asp
            35                  40                  45

Ala Tyr Pro Phe Asp Glu Ile Ile Tyr Cys Asn Ile Gly Asn Pro Gln
        50                  55                  60

Ser Leu Gly Gln Gln Pro Ile Thr Phe Phe Arg Glu Val Leu Ala Leu

```
                65                  70                  75                  80
Cys Ser Tyr Thr Ala Leu Leu Asp Glu Ser Ala Thr His Gly Leu Phe
                    85                  90                  95
Ser Ser Asp Ser Ile Glu Arg Ala Trp Lys Ile Leu Asp Gln Ile Pro
                    100                 105                 110
Gly Arg Ala Thr Gly Ala Tyr Ser His Ser Gln Gly Ile Lys Gly Leu
                    115                 120                 125
Arg Asp Ala Ile Ala Asp Gly Ile Glu Ala Arg Asp Gly Phe Pro Ala
        130                 135                 140
Asp Pro Asn Asp Ile Phe Met Thr Asp Gly Ala Ser Pro Gly Val His
145                 150                 155                 160
Met Met Met Gln Leu Leu Ile Thr Ser Glu Lys Asp Gly Ile Leu Cys
                    165                 170                 175
Pro Ile Pro Gln Tyr Pro Leu Tyr Ser Ala Ser Ile Ala Leu His Gly
                    180                 185                 190
Gly Thr Leu Val Pro Tyr Tyr Leu Asp Glu Ala Ser Gly Trp Gly Leu
                    195                 200                 205
Glu Ile Ser Glu Leu Lys Lys Gln Leu Glu Asp Ala Arg Ser Lys Gly
        210                 215                 220
Ile Thr Val Arg Ala Leu Ala Val Ile Asn Pro Gly Asn Pro Thr Gly
225                 230                 235                 240
Gln Val Leu Ser Glu Glu Asn Gln Arg Asp Val Val Lys Phe Cys Lys
                    245                 250                 255
Gln Glu Gly Leu Val Leu Leu Ala Asp Glu Val Tyr Gln Glu Asn Val
                    260                 265                 270
Tyr Val Pro Asp Lys Lys Phe His Ser Phe Lys Lys Val Ala Arg Ser
                    275                 280                 285
Met Gly Tyr Gly Glu Lys Asp Leu Ala Leu Val Ser Phe Gln Ser Val
        290                 295                 300
Ser Lys Gly Tyr Tyr Gly Glu Cys Gly Lys Arg Gly Gly Tyr Met Glu
305                 310                 315                 320
Val Thr Gly Phe Thr Ser Asp Val Arg Glu Gln Ile Tyr Lys Met Ala
                    325                 330                 335
Ser Val Asn Leu Cys Ser Asn Ile Ser Gly Gln Ile Leu Ala Ser Leu
                    340                 345                 350
Ile Met Ser Pro Pro Lys Pro Gly Asp Ser Tyr Glu Ser Tyr Ile
                    355                 360                 365
Ala Glu Lys Asp Gly Ile Leu Ser Ser Leu Ala Arg Arg Ala Lys Thr
        370                 375                 380
Leu Glu Glu Ala Leu Asn Lys Leu Glu Gly Val Thr Cys Asn Arg Ala
385                 390                 395                 400
Glu Gly Ala Met Tyr Leu Phe Pro Cys Leu His Leu Pro Gln Lys Ala
                    405                 410                 415
Ile Ala Ala Ala Glu Ala Lys Thr Ala Pro Asp Asn Phe Tyr Cys
                    420                 425                 430
Lys Arg Leu Leu Lys Ala Thr Gly Ile Val Val Pro Gly Ser Gly
        435                 440                 445
Phe Arg Gln Val Pro Gly Thr Trp His Phe Arg Cys Thr Ile Leu Pro
        450                 455                 460
Gln Glu Asp Lys Ile Pro Ala Ile Val Asp Arg Leu Thr Ala Phe His
465                 470                 475                 480
Gln Ser Phe Met Asp Glu Phe Arg Asp
                    485
```

<210> SEQ ID NO 35
<211> LENGTH: 519
<212> TYPE: DNA
<213> ORGANISM: Arabidopsis thaliana

<400> SEQUENCE: 35

| | | |
|---|---|---|
| atggcgttcc ctaaggtata cttcgacatg accatcgacg gccagcccgc gggaaggatc | 60 |
| gtgatggagc tgtacaccga taagactccc aggactgccg agaatttcag agctctctgc | 120 |
| accggagaga aggtgttgg cggtaccgga aaaccccttc acttcaaggg atctaagttt | 180 |
| caccgtgtga tccctaactt catgtgccag ggaggagatt tcaccgccgg aacggaaca | 240 |
| ggcggtgagt cgatctacgg gagcaagttc gaggacgaga atttcgagag aagcacacc | 300 |
| ggaccgggga tcctgtcgat ggcgaacgcc ggtgcaaaca cgaacggatc tcagttcttc | 360 |
| atctgcaccg tgaagaccga ttggcttgat gggaagcacg tggtgtttgg caggtcgtg | 420 |
| gaaggcttag acgtggtaaa ggccatcgag aaggttggat catcatctgg aaagccgacg | 480 |
| aagcctgtgg ttgttgccga ttgtggtcag ctctcttag | 519 |

<210> SEQ ID NO 36
<211> LENGTH: 172
<212> TYPE: PRT
<213> ORGANISM: Arabidopsis thaliana

<400> SEQUENCE: 36

Met Ala Phe Pro Lys Val Tyr Phe Asp Met Thr Ile Asp Gly Gln Pro
1               5                   10                  15

Ala Gly Arg Ile Val Met Glu Leu Tyr Thr Asp Lys Thr Pro Arg Thr
            20                  25                  30

Ala Glu Asn Phe Arg Ala Leu Cys Thr Gly Glu Lys Val Gly Gly
        35                  40                  45

Thr Gly Lys Pro Leu His Phe Lys Gly Ser Lys Phe His Arg Val Ile
    50                  55                  60

Pro Asn Phe Met Cys Gln Gly Gly Asp Phe Thr Ala Gly Asn Gly Thr
65                  70                  75                  80

Gly Gly Glu Ser Ile Tyr Gly Ser Lys Phe Glu Asp Glu Asn Phe Glu
                85                  90                  95

Arg Lys His Thr Gly Pro Gly Ile Leu Ser Met Ala Asn Ala Gly Ala
            100                 105                 110

Asn Thr Asn Gly Ser Gln Phe Phe Ile Cys Thr Val Lys Thr Asp Trp
        115                 120                 125

Leu Asp Gly Lys His Val Val Phe Gly Gln Val Glu Gly Leu Asp
    130                 135                 140

Val Val Lys Ala Ile Glu Lys Val Gly Ser Ser Ser Gly Lys Pro Thr
145                 150                 155                 160

Lys Pro Val Val Val Ala Asp Cys Gly Gln Leu Ser
                165                 170

<210> SEQ ID NO 37
<211> LENGTH: 1095
<212> TYPE: DNA
<213> ORGANISM: Arabidopsis thaliana

<400> SEQUENCE: 37

| | | |
|---|---|---|
| atgggtagtg caaaatcagc catgctgatc ctcttagtag caatggtcat cgcatcatgt | 60 |
| gccacggcca ttgatatgtc cgtggtttcc tacgacgata caaccgtct ccatagcgtt | 120 |

```
ttcgatgctg aggcctcgtt aatcttcgag tcatggatgg tcaaacatgg gaaagtgtac    180
gggtccgttg ccgagaagga acggcgtttg acgattttg aggacaacct ccgttttatc    240
aataaccgga acgctgagaa tctcagttat cggcttggtt tgaccgggtt tgcggattta    300
tctcttcatg agtataaaga agtttgccac ggggctgatc caagacctcc taggaaccac    360
gtctttatga ctagtagcga ccgatacaag actagtgctg atgatgtgct tcctaagtca    420
gttgattgga gaaacgaagg agcagtgact gaagtcaaag atcaaggcca ttgcaggagt    480
tgttgggctt tctcgactgt gggagcagtg gaaggcttaa acaagatcgt gacgggagag    540
ttagtcactt tgtctgagca agatttgatc aattgtaaca agaaaacaa tggttgcgga    600 ggaggcaaac tcgagactgc ctatgagttc atcatgaaaa atggtggtct tggtaccgac    660
aacgattatc cttacaaagc tgttaacgga gtctgtgatg ccgcctcaa ggaaaacaac    720 aagaatgtta tgattgatgg gtatgaaaat ttgcccgcaa acgacgaatc tgctctcatg    780
aaagcggttg ctcaccagcc tgtgactgcc gttatcgatt ccagtagccg agagtttcag    840
ctttatgaat cgggagtgtt tgatggctcg tgtggaacaa acctaaacca tggagttgtt    900
gtggtcgggt atggaactga gaatggtcgt gactactggc tcgtgaaaaa ctctaggggc    960
attacatggg gagaagctgg ctacatgaag atggctcgaa acattgccaa tccaagaggc   1020
ttatgtggca ttgcaatgcg agcttcatac cctctaaaga actcctttc taccgataaa   1080 agctccatcg cctaa                                                     1095

<210> SEQ ID NO 38
<211> LENGTH: 364
<212> TYPE: PRT
<213> ORGANISM: Arabidopsis thaliana

<400> SEQUENCE: 38

Met Gly Ser Ala Lys Ser Ala Met Leu Ile Leu Leu Val Ala Met Val
1               5                   10                  15

Ile Ala Ser Cys Ala Thr Ala Ile Asp Met Ser Val Val Ser Tyr Asp
            20                  25                  30

Asp Asn Asn Arg Leu His Ser Val Phe Asp Ala Glu Ala Ser Leu Ile
        35                  40                  45

Phe Glu Ser Trp Met Val Lys His Gly Lys Val Tyr Gly Ser Val Ala
    50                  55                  60

Glu Lys Glu Arg Arg Leu Thr Ile Phe Glu Asp Asn Leu Arg Phe Ile
65                  70                  75                  80

Asn Asn Arg Asn Ala Glu Asn Leu Ser Tyr Arg Leu Gly Leu Thr Gly
                85                  90                  95

Phe Ala Asp Leu Ser Leu His Glu Tyr Lys Glu Val Cys His Gly Ala
            100                 105                 110

Asp Pro Arg Pro Arg Asn His Val Phe Met Thr Ser Ser Asp Arg
        115                 120                 125

Tyr Lys Thr Ser Ala Asp Asp Val Leu Pro Lys Ser Val Asp Trp Arg
    130                 135                 140

Asn Glu Gly Ala Val Thr Glu Val Lys Asp Gln Gly His Cys Arg Ser
145                 150                 155                 160

Cys Trp Ala Phe Ser Thr Val Gly Ala Val Glu Gly Leu Asn Lys Ile
                165                 170                 175

Val Thr Gly Glu Leu Val Thr Leu Ser Glu Gln Asp Leu Ile Asn Cys
            180                 185                 190
```

```
Asn Lys Glu Asn Asn Gly Cys Gly Gly Gly Lys Leu Glu Thr Ala Tyr
            195                 200                 205

Glu Phe Ile Met Lys Asn Gly Gly Leu Gly Thr Asp Asn Asp Tyr Pro
        210                 215                 220

Tyr Lys Ala Val Asn Gly Val Cys Asp Gly Arg Leu Lys Glu Asn Asn
225                 230                 235                 240

Lys Asn Val Met Ile Asp Gly Tyr Glu Asn Leu Pro Ala Asn Asp Glu
                245                 250                 255

Ser Ala Leu Met Lys Ala Val Ala His Gln Pro Val Thr Ala Val Ile
            260                 265                 270

Asp Ser Ser Arg Glu Phe Gln Leu Tyr Glu Ser Gly Val Phe Asp
        275                 280                 285

Gly Ser Cys Gly Thr Asn Leu Asn His Gly Val Val Val Gly Tyr
        290                 295                 300

Gly Thr Glu Asn Gly Arg Asp Tyr Trp Leu Val Lys Asn Ser Arg Gly
305                 310                 315                 320

Ile Thr Trp Gly Glu Ala Gly Tyr Met Lys Met Ala Arg Asn Ile Ala
                325                 330                 335

Asn Pro Arg Gly Leu Cys Gly Ile Ala Met Arg Ala Ser Tyr Pro Leu
            340                 345                 350

Lys Asn Ser Phe Ser Thr Asp Lys Ser Ser Ile Ala
            355                 360

<210> SEQ ID NO 39
<211> LENGTH: 516
<212> TYPE: DNA
<213> ORGANISM: Arabidopsis thaliana

<400> SEQUENCE: 39
atgactaatc ccatgatcat ggttatgctg ttgttgtttc ttgtgatgtc gactagagca      60
gacgaagagc tgattaagac agagtgtaat cacacagaat accaaaacgt atgcctcttc     120
tgtcttgaag ccgatccaat ctccttcaat atcgaccgtg ctggacttgt caacatcatt     180
atacactgtc tcggatctca acttgatgtt cttatcaaca ccgtcacgag tctaaagttg     240
atgaaaggag agggtgaagc aaatgagaat gttctgaaag attgcgtcac aggctttgcg     300
attgcacaat tacgacttca aggagccaac atcgatttga taacccttaa ttacgataaa     360
gcgtacgaat tggtgaaaac tgcgttaaac tatcctcgga cttgcgaaga aaatctccaa     420
aaactcaagt tcaaagattc atctgatgtt tatgacgata tcttggcata tagccaactc     480
acctctgttg ctaagacgtt gatccaccgt ctctag                                516

<210> SEQ ID NO 40
<211> LENGTH: 171
<212> TYPE: PRT
<213> ORGANISM: Arabidopsis thaliana

<400> SEQUENCE: 40

Met Thr Asn Pro Met Ile Met Val Met Leu Leu Leu Phe Leu Val Met
1               5                   10                  15

Ser Thr Arg Ala Asp Glu Glu Leu Ile Lys Thr Glu Cys Asn His Thr
                20                  25                  30

Glu Tyr Gln Asn Val Cys Leu Phe Cys Leu Glu Ala Asp Pro Ile Ser
            35                  40                  45

Phe Asn Ile Asp Arg Ala Gly Leu Val Asn Ile Ile His Cys Leu
        50                  55                  60
```

```
Gly Ser Gln Leu Asp Val Leu Ile Asn Thr Val Thr Ser Leu Lys Leu
 65                  70                  75                  80

Met Lys Gly Glu Gly Glu Ala Asn Glu Asn Val Leu Lys Asp Cys Val
                 85                  90                  95

Thr Gly Phe Ala Ile Ala Gln Leu Arg Leu Gln Gly Ala Asn Ile Asp
            100                 105                 110

Leu Ile Thr Leu Asn Tyr Asp Lys Ala Tyr Glu Leu Val Lys Thr Ala
        115                 120                 125

Leu Asn Tyr Pro Arg Thr Cys Glu Glu Asn Leu Gln Lys Leu Lys Phe
    130                 135                 140

Lys Asp Ser Ser Asp Val Tyr Asp Asp Ile Leu Ala Tyr Ser Gln Leu
145                 150                 155                 160

Thr Ser Val Ala Lys Thr Leu Ile His Arg Leu
                165                 170
```

<210> SEQ ID NO 41
<211> LENGTH: 702
<212> TYPE: DNA
<213> ORGANISM: Arabidopsis thaliana

<400> SEQUENCE: 41

```
atggtttctt cttctttaac caagcttgtg ttctttggtt gtctcctcct gctcacattc    60
acggacaaac ttgtggctgg aaaatctggc aaagtgaagc tcaatcttta ctacgaatca   120
ctttgtcccg gttgtcagga attcatcgtc gatgacctag gtaaaatctt tgactacgat   180
ctctacacaa tcactgatct caagctgttt ccatttggta atgccgaact ctccgataat   240
ctgactgtca cttgccagca tggtgaagag gaatgcaaac taaacgccct tgaagcttgc   300
gcattaagaa cttggcccga tcagaaatca caatactcgt tcatacggtg cgtcgaaagc   360
gatacgaaag gctgggaatc atgtgttaaa aactctggac gtgagaaagc aatcaatgat   420
tgttacaatg gtgatctttc tagaaagctg atacttgggt acgcaaccaa aaccaagaat   480
ttgaagccgc cacatgaata cgtaccatgg gtcacactca acggcaagcc actcgatgac   540
agcgtacaaa gtacggatga tctcgtagct caaatctgca atgcatacaa aggaaagact   600
actctcccaa aagtttgcaa ttcatccgcc tcaatgtcta agtcgcctga gaggaaatgg   660
aagcttcaag tctcttatgc caataaagct accaattatt aa                     702
```

<210> SEQ ID NO 42
<211> LENGTH: 233
<212> TYPE: PRT
<213> ORGANISM: Arabidopsis thaliana

<400> SEQUENCE: 42

```
Met Val Ser Ser Ser Leu Thr Lys Leu Val Phe Phe Gly Cys Leu Leu
 1               5                  10                  15

Leu Leu Thr Phe Thr Asp Asn Leu Val Ala Gly Lys Ser Gly Lys Val
                 20                  25                  30

Lys Leu Asn Leu Tyr Tyr Glu Ser Leu Cys Pro Gly Cys Gln Glu Phe
            35                  40                  45

Ile Val Asp Asp Leu Gly Lys Ile Phe Asp Tyr Asp Leu Tyr Thr Ile
        50                  55                  60

Thr Asp Leu Lys Leu Phe Pro Phe Gly Asn Ala Glu Leu Ser Asp Asn
 65                  70                  75                  80

Leu Thr Val Thr Cys Gln His Gly Glu Glu Glu Cys Lys Leu Asn Ala
                 85                  90                  95
```

```
Leu Glu Ala Cys Ala Leu Arg Thr Trp Pro Asp Gln Lys Ser Gln Tyr
            100                 105                 110

Ser Phe Ile Arg Cys Val Glu Ser Asp Thr Lys Gly Trp Glu Ser Cys
        115                 120                 125

Val Lys Asn Ser Gly Arg Glu Lys Ala Ile Asn Asp Cys Tyr Asn Gly
    130                 135                 140

Asp Leu Ser Arg Lys Leu Ile Leu Gly Tyr Ala Thr Lys Thr Lys Asn
145                 150                 155                 160

Leu Lys Pro Pro His Glu Tyr Val Pro Trp Val Thr Leu Asn Gly Lys
                165                 170                 175

Pro Leu Asp Asp Ser Val Gln Ser Thr Asp Leu Val Ala Gln Ile
                180                 185                 190

Cys Asn Ala Tyr Lys Gly Lys Thr Thr Leu Pro Lys Val Cys Asn Ser
            195                 200                 205

Ser Ala Ser Met Ser Lys Ser Pro Glu Arg Lys Trp Lys Leu Gln Val
        210                 215                 220

Ser Tyr Ala Asn Lys Ala Thr Asn Tyr
225                 230
```

```
<210> SEQ ID NO 43
<211> LENGTH: 591
<212> TYPE: DNA
<213> ORGANISM: Arabidopsis thaliana

<400> SEQUENCE: 43
atggccggag ttttcaaaac ggttacgttt cttgttttgg ttttcgctgc cgttgttgtc      60
ttcgcggagg actacgatgt tggtgatgat acggaatgga cgagacctat ggaccccgag     120
ttctatacta cttgggctac cggtaaaact ttccgtgtag cgacgagct cgaatttgat      180 ttcgctgctg ggaggcatga tgtggcagtt gtatcagaag ctgcatttga aaactgtgag     240
aaagagaaac ccattagcca catgaccgtt cctccggtca aaattatgct aaacaccact     300
ggaccacaat actttatctg caccgtcggt gaccattgtc gttttggtca aaactttcc      360 atcactgtag ttgctgctgg tgcaactgga ggtgctactc ctggtgccgg tgctacccca     420
gcacctggat caaccccaag tactggagga accactcctc ccactgcggg tgggaccaca     480 acacttcag ctctagcgg aaccactact ccagctggaa atgccgcttc ctcattaggt       540
ggtgctactt ttctggtcgc ttttgtttct gctgttgttg ctctcttttg a              591

<210> SEQ ID NO 44
<211> LENGTH: 196
<212> TYPE: PRT
<213> ORGANISM: Arabidopsis thaliana

<400> SEQUENCE: 44

Met Ala Gly Val Phe Lys Thr Val Thr Phe Leu Val Leu Val Phe Ala
1               5                   10                  15

Ala Val Val Val Phe Ala Glu Asp Tyr Asp Val Gly Asp Asp Thr Glu
            20                  25                  30

Trp Thr Arg Pro Met Asp Pro Glu Phe Tyr Thr Thr Trp Ala Thr Gly
        35                  40                  45

Lys Thr Phe Arg Val Gly Asp Glu Leu Glu Phe Asp Phe Ala Ala Gly
    50                  55                  60

Arg His Asp Val Ala Val Val Ser Glu Ala Ala Phe Glu Asn Cys Glu
65                  70                  75                  80

Lys Glu Lys Pro Ile Ser His Met Thr Val Pro Pro Val Lys Ile Met
```

-continued

```
                85                  90                  95
Leu Asn Thr Thr Gly Pro Gln Tyr Phe Ile Cys Thr Val Gly Asp His
            100                 105                 110
Cys Arg Phe Gly Gln Lys Leu Ser Ile Thr Val Ala Ala Gly Ala
        115                 120                 125
Thr Gly Gly Ala Thr Pro Gly Ala Gly Ala Thr Pro Ala Pro Gly Ser
    130                 135                 140
Thr Pro Ser Thr Gly Gly Thr Thr Pro Pro Thr Ala Gly Gly Thr Thr
145                 150                 155                 160
Thr Pro Ser Gly Ser Ser Gly Thr Thr Thr Pro Ala Gly Asn Ala Ala
                165                 170                 175
Ser Ser Leu Gly Gly Ala Thr Phe Leu Val Ala Phe Val Ser Ala Val
            180                 185                 190
Val Ala Leu Phe
        195
```

<210> SEQ ID NO 45
<211> LENGTH: 459
<212> TYPE: DNA
<213> ORGANISM: Arabidopsis thaliana

<400> SEQUENCE: 45

| | | | | | | |
|---|---|---|---|---|---|---|
| atggcgtcaa | agcaactgag | cagagaagag | cttgatgaga | aggcgaagca | aggagagacc | 60 |
| gtcgtcccag | gtggcaccgg | tggccacagc | ctcgaagctc | aagagcatct | tgctgaagga | 120 |
| aggagcaagg | gagggcagac | gaggaaggag | cagctaggca | tgaaggttta | tcaggagatc | 180 |
| ggtcacaaag | gtggagaggc | gaggaaggag | cagttagggc | acgagggtta | tcaggagatg | 240 |
| ggtcacaaag | gtggagaggc | gaggaaggag | cagctagggc | acgagggtta | tcaggagatg | 300 |
| ggacacaaag | gaggagaggc | gaggaaggag | cagctagggc | acgagggtta | taaggagatg | 360 |
| ggacgtaaag | gaggactcag | tacgatggaa | aaatctggtg | gagagcgtgc | ggaggaagaa | 420 |
| gggattgaga | tcgatgagtc | aaagttcacc | aacaagtga | | | 459 |

<210> SEQ ID NO 46
<211> LENGTH: 152
<212> TYPE: PRT
<213> ORGANISM: Arabidopsis thaliana

<400> SEQUENCE: 46

```
Met Ala Ser Lys Gln Leu Ser Arg Glu Glu Leu Asp Glu Lys Ala Lys
1               5                   10                  15
Gln Gly Glu Thr Val Val Pro Gly Gly Thr Gly Gly His Ser Leu Glu
                20                  25                  30
Ala Gln Glu His Leu Ala Glu Gly Arg Ser Lys Gly Gly Gln Thr Arg
            35                  40                  45
Lys Glu Gln Leu Gly His Glu Gly Tyr Gln Glu Ile Gly His Lys Gly
        50                  55                  60
Gly Glu Ala Arg Lys Glu Gln Leu Gly His Glu Gly Tyr Gln Glu Met
65                  70                  75                  80
Gly His Lys Gly Gly Glu Ala Arg Lys Glu Gln Leu Gly His Glu Gly
                85                  90                  95
Tyr Gln Glu Met Gly His Lys Gly Gly Glu Ala Arg Lys Glu Gln Leu
            100                 105                 110
Gly His Glu Gly Tyr Lys Glu Met Gly Arg Lys Gly Gly Leu Ser Thr
        115                 120                 125
```

Met Glu Lys Ser Gly Gly Glu Arg Ala Glu Glu Gly Ile Glu Ile
    130                 135                 140

Asp Glu Ser Lys Phe Thr Asn Lys
145                 150

<210> SEQ ID NO 47
<211> LENGTH: 1191
<212> TYPE: DNA
<213> ORGANISM: Arabidopsis thaliana

<400> SEQUENCE: 47

```
atggcttcgg ttactttctc tgtccccaag ggtttcactg aattctcagg attgcgaagc    60
tcctctgctt ctcttccctt cggcaagaaa cttcttccg atgagttcgt ttccatcgtc    120
tccttccaga cttctgcaat gggaagcagt ggtggataca ggaaaggtgt gactgaggcc   180
aagcttaagg tggccattaa tggattcggt aggatcggga ggaacttcct gagatgttgg   240
catggtcgca aggactctcc tcttgatatc attgccatta atgacactgg tggcgtcaag   300
caggcttcgc atttacttaa atacgactct actctcggaa tctttgatgc tgatgtcaaa   360
ccttctggag agactgcaat ctctgttgat ggaaagatca tccaagttgt ctctaaccga   420
aacccgtctc ttctcccttg aaggagcta ggaattgaca ttgtcatcga aggaaccgga    480
gtgtttgtgg atagagaagg tgcagggaaa cacattgaag ctggtgccaa gaaggttatc    540
attactgctc aggcaaaagg agatattcca acttatgtcg ttggtgtcaa tgcagatgct   600
tacagtcatg atgaacctat catcagcaat gcatcttgca ctaccaactg tcttgctccc   660
tttgtcaaag ttcttgacca gaaattcggt atcataaagg gtacaatgac gactactcac   720
tcttacaccg gtgaccagag gttgctagac gcgagtcacc gtgatctaag gagagcaaga   780
gcagctgctt tgaacattgt tcctacttct acaggagcag ctaaagctgt ggctcttgtg    840
ctccctaacc tcaaaggaaa actcaacggg atcgctctcc gtgtaccaac accaaacgta    900
tcagtggttg atctcgttgt gcaggtctca agaagacat ttgctgagga agtcaacgct    960
gctttcagag attctgcaga gaaagagctt aaaggtatac tcgatgtctg cgatgagcca  1020
ctagtgtccg ttgatttcag atgctcagat ttttcaacga ccattgattc atcactcact  1080
atggttatgg gagatgatat ggttaaggtg attgcttggt atgataatga atggggttac  1140
tcacagagag ttgttgactt ggctgacatt gttgccaaca actggaagtg a           1191
```

<210> SEQ ID NO 48
<211> LENGTH: 396
<212> TYPE: PRT
<213> ORGANISM: Arabidopsis thaliana

<400> SEQUENCE: 48

Met Ala Ser Val Thr Phe Ser Val Pro Lys Gly Phe Thr Glu Phe Ser
1               5                   10                  15

Gly Leu Arg Ser Ser Ala Ser Leu Pro Phe Gly Lys Lys Leu Ser
            20                  25                  30

Ser Asp Glu Phe Val Ser Ile Val Ser Phe Gln Thr Ser Ala Met Gly
        35                  40                  45

Ser Ser Gly Gly Tyr Arg Lys Gly Val Thr Glu Ala Lys Leu Lys Val
    50                  55                  60

Ala Ile Asn Gly Phe Gly Arg Ile Gly Arg Asn Phe Leu Arg Cys Trp
65                  70                  75                  80

His Gly Arg Lys Asp Ser Pro Leu Asp Ile Ile Ala Ile Asn Asp Thr
                85                  90                  95

-continued

```
Gly Gly Val Lys Gln Ala Ser His Leu Leu Lys Tyr Asp Ser Thr Leu
             100                 105                 110
Gly Ile Phe Asp Ala Asp Val Lys Pro Ser Gly Glu Thr Ala Ile Ser
         115                 120                 125
Val Asp Gly Lys Ile Ile Gln Val Val Ser Asn Arg Asn Pro Ser Leu
    130                 135                 140
Leu Pro Trp Lys Glu Leu Gly Ile Asp Ile Val Ile Glu Gly Thr Gly
145                 150                 155                 160
Val Phe Val Asp Arg Glu Gly Ala Gly Lys His Ile Glu Ala Gly Ala
                165                 170                 175
Lys Lys Val Ile Ile Thr Ala Pro Gly Lys Gly Asp Ile Pro Thr Tyr
            180                 185                 190
Val Val Gly Val Asn Ala Asp Ala Tyr Ser His Asp Glu Pro Ile Ile
        195                 200                 205
Ser Asn Ala Ser Cys Thr Thr Asn Cys Leu Ala Pro Phe Val Lys Val
    210                 215                 220
Leu Asp Gln Lys Phe Gly Ile Ile Lys Gly Thr Met Thr Thr Thr His
225                 230                 235                 240
Ser Tyr Thr Gly Asp Gln Arg Leu Leu Asp Ala Ser His Arg Asp Leu
                245                 250                 255
Arg Arg Ala Arg Ala Ala Leu Asn Ile Val Pro Thr Ser Thr Gly
            260                 265                 270
Ala Ala Lys Ala Val Ala Leu Val Leu Pro Asn Leu Lys Gly Lys Leu
        275                 280                 285
Asn Gly Ile Ala Leu Arg Val Pro Thr Pro Asn Val Ser Val Val Asp
    290                 295                 300
Leu Val Val Gln Val Ser Lys Lys Thr Phe Ala Glu Glu Val Asn Ala
305                 310                 315                 320
Ala Phe Arg Asp Ser Ala Glu Lys Glu Leu Lys Gly Ile Leu Asp Val
                325                 330                 335
Cys Asp Glu Pro Leu Val Ser Val Asp Phe Arg Cys Ser Asp Phe Ser
            340                 345                 350
Thr Thr Ile Asp Ser Ser Leu Thr Met Val Met Gly Asp Asp Met Val
        355                 360                 365
Lys Val Ile Ala Trp Tyr Asp Asn Glu Trp Gly Tyr Ser Gln Arg Val
    370                 375                 380
Val Asp Leu Ala Asp Ile Val Ala Asn Asn Trp Lys
385                 390                 395
```

<210> SEQ ID NO 49
<211> LENGTH: 1569
<212> TYPE: DNA
<213> ORGANISM: Arabidopsis thaliana

<400> SEQUENCE: 49

| | | |
|---|---|---|
| atggcaaaag aaaatggatt tataggatca atcgatcaag gaaccaccag caccagattc | 60 |
| atcatttacg accacgatgc tcgtcctgtt gcttctcatc aagtcgagtt cactcagttc | 120 |
| tatcccgaag ctggatgggt ggaacacgat ccaatggaga tactggaaag tgtgaaagtg | 180 |
| tgcattgcaa aggctctcga caaagccact gccgatggac acaacgtcga cggtggcttg | 240 |
| aaggccattg gcttacaga tcagagagag actactgttg tttggagcaa atccactggc | 300 |
| cttcctctcc acaaggctat tgtctggatg gatgctcgta ccagctccat ctgcaggaga | 360 |
| ctagagaaag aactctcggg aggaagatcc cattttgtgg agtcttgcgg cttgccaata | 420 |

```
agcacatact tctctgccat gaagctgctt tggctcatgg agaatgtgga tgatgtcaaa      480
gacgctatca agaaagggga tgccatcttt ggcactatcg acacatggtt gatctggaac      540
atgactggcg gtatcaatgg cggccttcat gtcactgatg tcaccaatgc ttcacggaca      600
atgctcatga acctcaaaac cttgagctgg gaccaggaca ctttgaagac acttggcata      660
ccggctgaaa tcttgcccaa gattgtcagc aattcagaag tgattggaga gatctgcaaa      720
ggctggccta ttcccggtat caagattgct ggatgtcttg gtgatcagca tgctgcgatg      780
ttggggcaag cttgcagaaa aggcgaggcg aagagtactt atggcacagg tgctttcatt      840
cttctcaaca ccggagaagt gccaatcaaa tcaggtcatg gtcttctgac cacgttggcc      900
tacaagctcg gtcctcaagc acagacaaac tatgcattgg agggttcgat tgccatagca      960
ggagctgctg ttcagtggct tagagacagc cttgggataa tcaaaagcgc ctctgagatc     1020
gaagatttgg cagcaatggt agattctaca ggaggagtgt actttgtgcc agcgttcaac     1080
ggcttgtttg ctccttggtg gagagaagac gcacgtggtg tgtgcattgg aatcacgagg     1140
ttcaccaaca gtctcacatt gctcgggct gtgctggaga gcatgtgttt ccaggtgaaa     1200
gacgtccttg actccatgaa caaagatgca ggtgaaaagg gttcccttaa taacgggaaa     1260
ggggagttct tgctcagagt tgatggtggt gccacagcta acaaccttct gatgcagatt     1320
caggctgatc tgatgggaag tccggtggtg aggccagtgg acatagagac aacagcatta     1380
ggagcagcct atgcagctgg attagctgtg ggattctgga aggaagcaga catattcgag     1440
tcgggagaga aggcgaagaa ctccaaagtt ttcagacccg ctatggaaga aggaatcagg     1500
aagaagaaag tggcgtcttg gtgcaaagcg gtggaaagaa catttgatct cgctgacctc     1560
tctatctaa                                                              1569
```

<210> SEQ ID NO 50
<211> LENGTH: 522
<212> TYPE: PRT
<213> ORGANISM: Arabidopsis thaliana

<400> SEQUENCE: 50

```
Met Ala Lys Glu Asn Gly Phe Ile Gly Ser Ile Asp Gln Gly Thr Thr
1               5                   10                  15

Ser Thr Arg Phe Ile Ile Tyr Asp His Asp Ala Arg Pro Val Ala Ser
            20                  25                  30

His Gln Val Glu Phe Thr Gln Phe Tyr Pro Glu Ala Gly Trp Val Glu
        35                  40                  45

His Asp Pro Met Glu Ile Leu Glu Ser Val Lys Val Cys Ile Ala Lys
    50                  55                  60

Ala Leu Asp Lys Ala Thr Ala Asp Gly His Asn Val Asp Gly Gly Leu
65                  70                  75                  80

Lys Ala Ile Gly Leu Thr Asp Gln Arg Glu Thr Thr Val Val Trp Ser
                85                  90                  95

Lys Ser Thr Gly Leu Pro Leu His Lys Ala Ile Val Trp Met Asp Ala
            100                 105                 110

Arg Thr Ser Ser Ile Cys Arg Arg Leu Glu Lys Glu Leu Ser Gly Gly
        115                 120                 125

Arg Ser His Phe Val Glu Ser Cys Gly Leu Pro Ile Ser Thr Tyr Phe
    130                 135                 140

Ser Ala Met Lys Leu Leu Trp Leu Met Glu Asn Val Asp Asp Val Lys
145                 150                 155                 160
```

```
Asp Ala Ile Lys Lys Gly Asp Ala Ile Phe Gly Thr Ile Asp Thr Trp
                165                 170                 175

Leu Ile Trp Asn Met Thr Gly Gly Ile Asn Gly Gly Leu His Val Thr
            180                 185                 190

Asp Val Thr Asn Ala Ser Arg Thr Met Leu Met Asn Leu Lys Thr Leu
        195                 200                 205

Ser Trp Asp Gln Asp Thr Leu Lys Thr Leu Gly Ile Pro Ala Glu Ile
210                 215                 220

Leu Pro Lys Ile Val Ser Asn Ser Glu Val Ile Gly Glu Ile Cys Lys
225                 230                 235                 240

Gly Trp Pro Ile Pro Gly Ile Lys Ile Ala Gly Cys Leu Gly Asp Gln
                245                 250                 255

His Ala Ala Met Leu Gly Gln Ala Cys Arg Lys Gly Glu Ala Lys Ser
            260                 265                 270

Thr Tyr Gly Thr Gly Ala Phe Ile Leu Leu Asn Thr Gly Glu Val Pro
        275                 280                 285

Ile Lys Ser Gly His Gly Leu Leu Thr Thr Leu Ala Tyr Lys Leu Gly
290                 295                 300

Pro Gln Ala Gln Thr Asn Tyr Ala Leu Glu Gly Ser Ile Ala Ile Ala
305                 310                 315                 320

Gly Ala Ala Val Gln Trp Leu Arg Asp Ser Leu Gly Ile Ile Lys Ser
                325                 330                 335

Ala Ser Glu Ile Glu Asp Leu Ala Ala Met Val Asp Ser Thr Gly Gly
            340                 345                 350

Val Tyr Phe Val Pro Ala Phe Asn Gly Leu Phe Ala Pro Trp Trp Arg
        355                 360                 365

Glu Asp Ala Arg Gly Val Cys Ile Gly Ile Thr Arg Phe Thr Asn Lys
370                 375                 380

Ser His Ile Ala Arg Ala Val Leu Glu Ser Met Cys Phe Gln Val Lys
385                 390                 395                 400

Asp Val Leu Asp Ser Met Asn Lys Asp Ala Gly Glu Lys Gly Ser Leu
                405                 410                 415

Asn Asn Gly Lys Gly Glu Phe Leu Leu Arg Val Asp Gly Gly Ala Thr
            420                 425                 430

Ala Asn Asn Leu Leu Met Gln Ile Gln Ala Asp Leu Met Gly Ser Pro
        435                 440                 445

Val Val Arg Pro Val Asp Ile Glu Thr Thr Ala Leu Gly Ala Ala Tyr
450                 455                 460

Ala Ala Gly Leu Ala Val Gly Phe Trp Lys Glu Ala Asp Ile Phe Glu
465                 470                 475                 480

Ser Gly Glu Lys Ala Lys Asn Ser Lys Val Phe Arg Pro Ala Met Glu
                485                 490                 495

Glu Gly Ile Arg Lys Lys Val Ala Ser Trp Cys Lys Ala Val Glu
            500                 505                 510

Arg Thr Phe Asp Leu Ala Asp Leu Ser Ile
            515                 520
```

<210> SEQ ID NO 51
<211> LENGTH: 741
<212> TYPE: DNA
<213> ORGANISM: Arabidopsis thaliana

<400> SEQUENCE: 51
atggcggcga aaattcccgg agtgatcgct ttgttcgacg tcgacggtac tctcacagct    60

-continued

```
ccaaggaagg aagctactcc agaattgctc gattttatcc gagaattgcg aaaggtcgtc      120
actattggag tcgtcggtgg atctgatcta agtaagatat ctgagcagct tggcaaaaca      180
gtcacaaacg actatgatta ttgtttctct gagaatggtc ttgtcgccca taaagatggg      240
aaatccattg gaattcagag cctgaagctg caccttggag acgataaact caaggagttg      300
ataaatttca cgctgcacta cattgcagac ctggatattc caattaagag gggaacattt      360
attgaattcc gaaatggaat gctcaatgta tcacccattg gtcgcaactg cagccaagaa      420
gaaagagatg aatttgagag atatgataag gttcaaaaca tccgaccaaa gatggtagct      480
gaacttcgtg agcggtttgc acatcttaac cttactttct caattggggg acagataagc      540
ttcgatgtct tccctaaagg ttgggataag acttactgct tgcaatacct cgaggacttc      600
agtgaaatcc atttcttcgg tgacaagacc tatgagggtg aaatgactat gaaatctat       660 gaatcaccaa aaacaattgg ccattcagtt acgagtccag atgacacagt ggcaaaatgc      720
aaggctctgt tcatgtcttg a                                                741
```

<210> SEQ ID NO 52
<211> LENGTH: 246
<212> TYPE: PRT
<213> ORGANISM: Arabidopsis thaliana
<400> SEQUENCE: 52

```
Met Ala Ala Lys Ile Pro Gly Val Ile Ala Leu Phe Asp Val Asp Gly
  1               5                  10                  15

Thr Leu Thr Ala Pro Arg Lys Glu Ala Thr Pro Glu Leu Leu Asp Phe
             20                  25                  30

Ile Arg Glu Leu Arg Lys Val Val Thr Ile Gly Val Val Gly Gly Ser
         35                  40                  45

Asp Leu Ser Lys Ile Ser Glu Gln Leu Gly Lys Thr Val Thr Asn Asp
     50                  55                  60

Tyr Asp Tyr Cys Phe Ser Glu Asn Gly Leu Val Ala His Lys Asp Gly
 65                  70                  75                  80

Lys Ser Ile Gly Ile Gln Ser Leu Lys Leu His Leu Gly Asp Asp Lys
                 85                  90                  95

Leu Lys Glu Leu Ile Asn Phe Thr Leu His Tyr Ile Ala Asp Leu Asp
            100                 105                 110

Ile Pro Ile Lys Arg Gly Thr Phe Ile Glu Phe Arg Asn Gly Met Leu
        115                 120                 125

Asn Val Ser Pro Ile Gly Arg Asn Cys Ser Gln Glu Glu Arg Asp Glu
    130                 135                 140

Phe Glu Arg Tyr Asp Lys Val Gln Asn Ile Arg Pro Lys Met Val Ala
145                 150                 155                 160

Glu Leu Arg Glu Arg Phe Ala His Leu Asn Leu Thr Phe Ser Ile Gly
                165                 170                 175

Gly Gln Ile Ser Phe Asp Val Phe Pro Lys Gly Trp Asp Lys Thr Tyr
            180                 185                 190

Cys Leu Gln Tyr Leu Glu Asp Phe Ser Glu Ile His Phe Phe Gly Asp
        195                 200                 205

Lys Thr Tyr Glu Gly Gly Asn Asp Tyr Glu Ile Tyr Glu Ser Pro Lys
    210                 215                 220

Thr Ile Gly His Ser Val Thr Ser Pro Asp Asp Thr Val Ala Lys Cys
225                 230                 235                 240

Lys Ala Leu Phe Met Ser
                245
```

-continued

<210> SEQ ID NO 53
<211> LENGTH: 1170
<212> TYPE: DNA
<213> ORGANISM: Arabidopsis thaliana

<400> SEQUENCE: 53

| | | | | | |
|---|---|---|---|---|---|
| atgggttaca | taggagctca | tggtgtagca | gctcttcata | ggtacaaata | cagtggagtg | 60 |
| gatcactctt | atcttgccaa | atacgtcctc | caaccttttt | ggactcgatt | tgtcaaagtc | 120 |
| ttccctctat | ggatgccacc | aaacatgata | acgcttatgg | ggtttatgtt | tctagtcact | 180 |
| tcctccctgc | taggctatat | atattcacct | cagttggatt | ctcctcctcc | acgatgggtt | 240 |
| cacttcgcac | atggtttact | tctcttcttg | tatcagacat | tgatgcggt | tgatgggaag | 300 |
| caagcaagaa | ggacaaattc | tctagccccc | taggagagc | tcttcgatca | tggttgtgac | 360 |
| gcgcttgctt | gtgcgtttga | agccatggca | tttggaagca | ctgcaatgtg | tggaagagat | 420 |
| actttctggt | tctgggttat | ttcagctatt | ccattttatg | gagctacatg | ggaacactat | 480 |
| ttcaccaaca | cacttattct | tccggttatc | aatgggccta | cagagggct | tgcacttata | 540 |
| tttgtcagcc | acttcttcac | agccatcgtc | ggtgctgaat | ggtgggctca | gcagttaggg | 600 |
| cagtcaatac | cattgtttag | ttgggtgcca | tttgtgaatg | agattcaaac | ttctagagca | 660 |
| gtgctataca | tgatgatcgc | ttttgctgtt | ataccaaccg | ttgcattcaa | tgtaacaaat | 720 |
| gtctacaaag | tcgttcgatc | aagaaacggg | agcatggtgt | tagcgttagc | tatgctgtat | 780 |
| cccttcgttg | tcttacttgg | aggagttttg | atatgggatt | acttgtctcc | aatcaatctc | 840 |
| atagcaacat | atcctcactt | agttgtactc | ggaactggac | ttgcatttgg | atttttagtg | 900 |
| ggaagaatga | ttcttgctca | cttgtgtgat | gagcctaaag | gactaaaaac | aaacatgtgc | 960 |
| atgtcactac | tctatcttcc | ctttgcactt | gcaaatgcgc | taaccgcaag | attgaatgct | 1020 |
| ggggttcctc | tagtcgacga | attatgggtt | cttcttggct | actgcatatt | cacagtgtca | 1080 |
| ttatacttgc | actttgcaac | atcagtcatc | catgagatca | ctgaggccct | tggaatctac | 1140 |
| tgctttagga | tcacgcgtaa | agaagcttga | | | | 1170 |

<210> SEQ ID NO 54
<211> LENGTH: 389
<212> TYPE: PRT
<213> ORGANISM: Arabidopsis thaliana

<400> SEQUENCE: 54

Met Gly Tyr Ile Gly Ala His Gly Val Ala Ala Leu His Arg Tyr Lys
1               5                  10                  15

Tyr Ser Gly Val Asp His Ser Tyr Leu Ala Lys Tyr Val Leu Gln Pro
            20                  25                  30

Phe Trp Thr Arg Phe Val Lys Val Phe Pro Leu Trp Met Pro Pro Asn
        35                  40                  45

Met Ile Thr Leu Met Gly Phe Met Phe Leu Val Thr Ser Ser Leu Leu
    50                  55                  60

Gly Tyr Ile Tyr Ser Pro Gln Leu Asp Ser Pro Pro Arg Trp Val
65                  70                  75                  80

His Phe Ala His Gly Leu Leu Leu Phe Leu Tyr Gln Thr Phe Asp Ala
                85                  90                  95

Val Asp Gly Lys Gln Ala Arg Arg Thr Asn Ser Ser Ser Pro Leu Gly
            100                 105                 110

Glu Leu Phe Asp His Gly Cys Asp Ala Leu Ala Cys Ala Phe Glu Ala

```
                115                 120                 125
Met Ala Phe Gly Ser Thr Ala Met Cys Gly Arg Asp Thr Phe Trp Phe
    130                 135                 140

Trp Val Ile Ser Ala Ile Pro Phe Tyr Gly Ala Thr Trp Glu His Tyr
145                 150                 155                 160

Phe Thr Asn Thr Leu Ile Leu Pro Val Ile Asn Gly Pro Thr Glu Gly
                165                 170                 175

Leu Ala Leu Ile Phe Val Ser His Phe Phe Thr Ala Ile Val Gly Ala
            180                 185                 190

Glu Trp Trp Ala Gln Gln Leu Gly Gln Ser Ile Pro Leu Phe Ser Trp
        195                 200                 205

Val Pro Phe Val Asn Glu Ile Gln Thr Ser Arg Ala Val Leu Tyr Met
    210                 215                 220

Met Ile Ala Phe Ala Val Ile Pro Thr Val Ala Phe Asn Val Thr Asn
225                 230                 235                 240

Val Tyr Lys Val Val Arg Ser Arg Asn Gly Ser Met Val Leu Ala Leu
                245                 250                 255

Ala Met Leu Tyr Pro Phe Val Val Leu Leu Gly Gly Val Leu Ile Trp
            260                 265                 270

Asp Tyr Leu Ser Pro Ile Asn Leu Ile Ala Thr Tyr Pro His Leu Val
        275                 280                 285

Val Leu Gly Thr Gly Leu Ala Phe Gly Phe Leu Val Gly Arg Met Ile
    290                 295                 300

Leu Ala His Leu Cys Asp Glu Pro Lys Gly Leu Lys Thr Asn Met Cys
305                 310                 315                 320

Met Ser Leu Leu Tyr Leu Pro Phe Ala Leu Ala Asn Ala Leu Thr Ala
                325                 330                 335

Arg Leu Asn Ala Gly Val Pro Leu Val Asp Glu Leu Trp Val Leu Leu
            340                 345                 350

Gly Tyr Cys Ile Phe Thr Val Ser Leu Tyr Leu His Phe Ala Thr Ser
        355                 360                 365

Val Ile His Glu Ile Thr Glu Ala Leu Gly Ile Tyr Cys Phe Arg Ile
    370                 375                 380

Thr Arg Lys Glu Ala
385

<210> SEQ ID NO 55
<211> LENGTH: 2019
<212> TYPE: DNA
<213> ORGANISM: Arabidopsis thaliana

<400> SEQUENCE: 55
atgtctcctt ctcactccat caattccaac agtgacggca acgcctcctg ttcaacctgc      60
agcacctgct tcgatactac aacctccaca acagatgaag agtatgatgc tttgattaag     120
actaagactt ggagtttagt gcctaaacct gcaggtacaa acattatcaa ttcgatttgg     180
ctttataaac acaagtacaa tgctgatggt tctttgtcaa gatacaaatc gagactcgtt     240
gctaatggaa aatcacaaga acacggagta gatttttatg agacgttcag tccggttgta     300
aagcctgcaa caatccgtgc ggttctaaac tttgcggtgg aacgcgactc gtcggtacat     360
caattagatg ttcaaaacgc gtttcttcat ggcaagctag aagaaactgt ttacatgtat     420
gagccacctg gatttgtcga taacaagaat ccaggatatg tttgcaagct gaataaggcg     480
ttgtatggtt taaacaagc accacgtgct tggaatgctc gatttgcaag ctatgtcaaa     540
```

```
atgatgggtt tcaaacagag taagtgtgat gcttcacttt tcgtatacaa gcaagggaat    600
gacatggctt acttgctgct ctacgttgat gacattatgc taactgcttc ttccccaagt    660
caagaaaaat atgcgaagaa tattattaac atagttgaga tgcaaaactg aagcctagt     720
ctcacatcgg ttgatcttgc gtgtaagctt gaagaaagtg ttggtccaaa aatacaagac    780
ctgacgttat atcgaagttt ggttggggca cttcagtact taacaataac gagaccgaac    840
atatcttatg cagttcaaca aggtctcagt attacaaagt ccccatcaac caaactagtt    900
gccgactcgg acgcagactg ggttgggtgt ccgaatacta aagatcgac ttcggggtat     960
tgtgtttttc ttagggatac actcatctca tggtcgtcta agcgacaagg ttcagtgtca   1020
cgttcaagcg cagaggctga gtacaaagcc gtagcaaatg cagtggtagc aacatgcgaa   1080
gttcgagtca ttcatatccc tgcttctcat caatatgctg acattttcac aaagggtctt   1140
actacttcac tgttcaatcg attcaagtcc agtcttggcg tcattcaacg accgacgaaa   1200
agactgcggg aaggtgattt gttgttcaac agaaaagatg agattcgtac gttcgaggtt   1260
gtctctcgtt atggtcacgg tcctaagctt cttggccggt tttctggcgg tcgaatcgag   1320
gagtttatta atgcccggac gttatcagca gcaaatctac gtgacgcgga agtacctact   1380
cgtgttgcgg ctaagctaag agagtttcat ggtatcaaca tccctggtga tagaaatgtg   1440
ctcatttggg ataggatgag gaattggctt agacaagcca aaagtctgtg tacacctgaa   1500
gatttagcag agtttggtct agacaagatt gaagatgaga tatacttgct ggaacatgag   1560
ctgcaggata gtgtaagca gcaggagata gggttttgtc acaatgattt gcaatatggt    1620
aacattatga ttgatgaaga taccaatgcc attactatca ttgactacga gtacgctagt   1680
tataacccag ttgcatacga cattgcaaat cacttctgcg aaatggcagc aaattacaaa   1740
gttgcaggag aagaggaacg aaggaggttc atccataact acctcagctc ttcaggcgaa   1800
gaaccaaaag aagatgacat aaaacagctc ttgaaggatg ctgagaagta cacattagca   1860
agccatctgt tttggggctt atggggaatc atctctggat atgtaaacaa gatcgacttc   1920
gattacgccg agtactcaag acagagattc aaacaatact ggcttcgaaa acccgagctc   1980
ttactcttct cccaaatgta tatttcaaac accaaatga                          2019
```

<210> SEQ ID NO 56
<211> LENGTH: 672
<212> TYPE: PRT
<213> ORGANISM: Arabidopsis thaliana

<400> SEQUENCE: 56

```
Met Ser Pro Ser His Ser Ile Asn Ser Asn Ser Asp Gly Asn Ala Ser
1               5                   10                  15

Cys Ser Thr Cys Ser Thr Cys Phe Asp Thr Thr Ser Thr Thr Asp
            20                  25                  30

Glu Glu Tyr Asp Ala Leu Ile Lys Thr Lys Thr Trp Ser Leu Val Pro
        35                  40                  45

Lys Pro Ala Gly Thr Asn Ile Ile Asn Ser Ile Trp Leu Tyr Lys His
    50                  55                  60

Lys Tyr Asn Ala Asp Gly Ser Leu Ser Arg Tyr Lys Ser Arg Leu Val
65                  70                  75                  80

Ala Asn Gly Lys Ser Gln Glu His Gly Val Asp Phe Tyr Glu Thr Phe
                85                  90                  95

Ser Pro Val Val Lys Pro Ala Thr Ile Arg Ala Val Leu Asn Phe Ala
            100                 105                 110
```

-continued

```
Val Glu Arg Asp Ser Ser Val His Gln Leu Asp Val Gln Asn Ala Phe
    115                 120                 125
Leu His Gly Lys Leu Glu Thr Val Tyr Met Tyr Glu Pro Pro Gly
    130                 135                 140
Phe Val Asp Asn Lys Asn Pro Gly Tyr Val Cys Lys Leu Asn Lys Ala
145                 150                 155                 160
Leu Tyr Gly Phe Lys Gln Ala Pro Arg Ala Trp Asn Ala Arg Phe Ala
                165                 170                 175
Ser Tyr Val Lys Met Met Gly Phe Lys Gln Ser Lys Cys Asp Ala Ser
            180                 185                 190
Leu Phe Val Tyr Lys Gln Gly Asn Asp Met Ala Tyr Leu Leu Leu Tyr
        195                 200                 205
Val Asp Asp Ile Met Leu Thr Ala Ser Ser Pro Ser Gln Glu Lys Tyr
    210                 215                 220
Ala Lys Asn Ile Ile Asn Ile Val Glu Met Gln Asn Trp Lys Pro Ser
225                 230                 235                 240
Leu Thr Ser Val Asp Leu Ala Cys Lys Leu Glu Glu Ser Val Gly Pro
                245                 250                 255
Lys Ile Gln Asp Leu Thr Leu Tyr Arg Ser Leu Val Gly Ala Leu Gln
            260                 265                 270
Tyr Leu Thr Ile Thr Arg Pro Asn Ile Ser Tyr Ala Val Gln Gln Gly
        275                 280                 285
Leu Ser Ile Thr Lys Ser Pro Ser Thr Lys Leu Val Ala Asp Ser Asp
    290                 295                 300
Ala Asp Trp Val Gly Cys Pro Asn Thr Arg Arg Ser Thr Ser Gly Tyr
305                 310                 315                 320
Cys Val Phe Leu Arg Asp Thr Leu Ile Ser Trp Ser Ser Lys Arg Gln
                325                 330                 335
Gly Ser Val Ser Arg Ser Ser Ala Glu Ala Glu Tyr Lys Ala Val Ala
            340                 345                 350
Asn Ala Val Val Ala Thr Cys Glu Val Arg Val Ile His Ile Pro Ala
        355                 360                 365
Ser His Gln Tyr Ala Asp Ile Phe Thr Lys Gly Leu Thr Thr Ser Leu
    370                 375                 380
Phe Asn Arg Phe Lys Ser Ser Leu Gly Val Ile Gln Arg Pro Thr Lys
385                 390                 395                 400
Arg Leu Arg Glu Gly Asp Leu Leu Phe Asn Arg Lys Asp Glu Ile Arg
                405                 410                 415
Thr Phe Glu Val Val Ser Arg Tyr Gly His Gly Pro Lys Leu Leu Gly
            420                 425                 430
Arg Phe Ser Gly Gly Arg Ile Glu Glu Phe Ile Asn Ala Arg Thr Leu
        435                 440                 445
Ser Ala Ala Asn Leu Arg Asp Ala Glu Val Pro Thr Arg Val Ala Ala
    450                 455                 460
Lys Leu Arg Glu Phe His Gly Ile Asn Ile Pro Gly Asp Arg Asn Val
465                 470                 475                 480
Leu Ile Trp Asp Arg Met Arg Asn Trp Leu Arg Gln Ala Lys Ser Leu
                485                 490                 495
Cys Thr Pro Glu Asp Leu Ala Glu Phe Gly Leu Asp Lys Ile Glu Asp
            500                 505                 510
Glu Ile Tyr Leu Leu Glu His Glu Leu Gln Asp Lys Cys Lys Gln Gln
        515                 520                 525
Glu Ile Gly Phe Cys His Asn Asp Leu Gln Tyr Gly Asn Ile Met Ile
```

-continued

```
                 530                 535                 540
Asp Glu Asp Thr Asn Ala Ile Thr Ile Ile Asp Tyr Glu Tyr Ala Ser
545                 550                 555                 560

Tyr Asn Pro Val Ala Tyr Asp Ile Ala Asn His Phe Cys Glu Met Ala
                565                 570                 575

Ala Asn Tyr Lys Val Ala Gly Glu Glu Arg Arg Phe Ile His
            580                 585                 590

Asn Tyr Leu Ser Ser Gly Glu Glu Pro Lys Glu Asp Asp Ile Lys
                595                 600                 605

Gln Leu Leu Lys Asp Ala Glu Lys Tyr Thr Leu Ala Ser His Leu Phe
            610                 615                 620

Trp Gly Leu Trp Gly Ile Ile Ser Gly Tyr Val Asn Lys Ile Asp Phe
625                 630                 635                 640

Asp Tyr Ala Glu Tyr Ser Arg Gln Arg Phe Lys Gln Tyr Trp Leu Arg
                645                 650                 655

Lys Pro Glu Leu Leu Leu Phe Ser Gln Met Tyr Ile Ser Asn Thr Lys
            660                 665                 670

<210> SEQ ID NO 57
<211> LENGTH: 897
<212> TYPE: DNA
<213> ORGANISM: Arabidopsis thaliana

<400> SEQUENCE: 57
atggcatctg tttactccac cctaacctac tggctcgtcc accacccta cattgccaac       60 ttcacgtgga ccgaaggtga aacactaggc tccaccgttt tctttgtctt tgtcgtcgtc     120 tcccttacc tctccgccac attcctcctc cgatacaccg tcgattcact ccccacactc      180
ggtccccgca ttctcaaacc aatcacagcc gttcacagcc tcattctctt cctcctctcc    240
ttaaccatgg ccgttggttg cactctctcc ctaatctctt cctcggaccc gaaggcgcgt    300
ctcttcgacg ccgtttgttt cccccctcgac gtgaaaccta agggaccgct tttcttttgg    360
gctcaagtct tttacctctc gaagatcctt gagttcgtag acacacttct catcatactc    420
aacaaatcaa tccaacggct ctcgttcctc cacgtctacc accacgcaac ggttgtgatt    480
ttgtgctacc tctggttacg aacacgtcaa tcgatgtttc ctgttgggct cgtgttgaac    540
tcgacggtcc atgtgattat gtacgggtac tatttcctct gcgctatcgg atcgaggccc    600
aagtggaaga agttggtgac gaattttcaa atggttcagt ttgctttcgg catgggvtta    660
ggagccgctt ggatgctccc agagcattat ttcgggtcgg gttgcgccgg gatttggaca    720
gtttatttca atggtgtgtt tactgcttct ctattggctc tcttctacaa cttccactcc    780
aagaactatg agaagactac aacgtcgcct tgtataaga tcgaatcctt tatatttatt     840
cacggagaga ggtgggcaaa taaagcgatt acattatttt ccaagaaaaa cgattaa       897

<210> SEQ ID NO 58
<211> LENGTH: 298
<212> TYPE: PRT
<213> ORGANISM: Arabidopsis thaliana

<400> SEQUENCE: 58

Met Ala Ser Val Tyr Ser Thr Leu Thr Tyr Trp Leu Val His His Pro
1               5                   10                  15

Tyr Ile Ala Asn Phe Thr Trp Thr Glu Gly Glu Thr Leu Gly Ser Thr
            20                  25                  30

Val Phe Phe Val Phe Val Val Val Ser Leu Tyr Leu Ser Ala Thr Phe
```

-continued

```
            35                  40                  45
Leu Leu Arg Tyr Thr Val Asp Ser Leu Pro Thr Leu Gly Pro Arg Ile
 50                  55                  60

Leu Lys Pro Ile Thr Ala Val His Ser Leu Ile Leu Phe Leu Leu Ser
65                  70                  75                  80

Leu Thr Met Ala Val Gly Cys Thr Leu Ser Leu Ile Ser Ser Ser Asp
                85                  90                  95

Pro Lys Ala Arg Leu Phe Asp Ala Val Cys Phe Pro Leu Asp Val Lys
            100                 105                 110

Pro Lys Gly Pro Leu Phe Phe Trp Ala Gln Val Phe Tyr Leu Ser Lys
            115                 120                 125

Ile Leu Glu Phe Val Asp Thr Leu Leu Ile Ile Leu Asn Lys Ser Ile
130                 135                 140

Gln Arg Leu Ser Phe Leu His Val Tyr His His Ala Thr Val Val Ile
145                 150                 155                 160

Leu Cys Tyr Leu Trp Leu Arg Thr Arg Gln Ser Met Phe Pro Val Gly
                165                 170                 175

Leu Val Leu Asn Ser Thr Val His Val Ile Met Tyr Gly Tyr Tyr Phe
            180                 185                 190

Leu Cys Ala Ile Gly Ser Arg Pro Lys Trp Lys Lys Leu Val Thr Asn
            195                 200                 205

Phe Gln Met Val Gln Phe Ala Phe Gly Met Gly Leu Gly Ala Ala Trp
210                 215                 220

Met Leu Pro Glu His Tyr Phe Gly Ser Gly Cys Ala Gly Ile Trp Thr
225                 230                 235                 240

Val Tyr Phe Asn Gly Val Phe Thr Ala Ser Leu Leu Ala Leu Phe Tyr
                245                 250                 255

Asn Phe His Ser Lys Asn Tyr Glu Lys Thr Thr Ser Pro Leu Tyr
            260                 265                 270

Lys Ile Glu Ser Phe Ile Phe Ile His Gly Glu Arg Trp Ala Asn Lys
            275                 280                 285

Ala Ile Thr Leu Phe Ser Lys Lys Asn Asp
            290                 295
```

<210> SEQ ID NO 59
<211> LENGTH: 837
<212> TYPE: DNA
<213> ORGANISM: Arabidopsis thaliana

<400> SEQUENCE: 59

| | | | | | |
|---|---|---|---|---|---|
| atggcatcaa | tttactcctc | tttaacctac | tggctcgtta | accacccta | catctccaat | 60 |
| tttacttgga | tcgaaggtga | aaccctaggc | tccaccgtct | ttttcgtatc | cgtcgtagtc | 120 |
| tccgtttacc | tctccgccac | gttcctcctc | cgatccgcca | tcgattcact | cccatcactc | 180 |
| agtccacgta | tcctcaaacc | gatcacagcc | gtccacagcc | taatcctctg | tctcctctcc | 240 |
| ttagtcatgg | ccgtcggttg | cactctctca | ataacctcat | ctcacgcgtc | ttcagatccg | 300 |
| atggcgcgtt | tccttcacgc | gatttgcttt | cccgtcgacg | ttaaacctaa | cggaccgctt | 360 |
| ttcttctggg | ctcaagtctt | ctacctctcg | aagatcctcg | agttcggaga | cacgatcctc | 420 |
| atcatactcg | gcaaatcaat | ccaacggcta | tccttcctcc | acgtgtacca | ccacgcgacg | 480 |
| gttgtggtca | tgtgttatct | ctggctccga | actcgccaat | cgatgtttcc | gattgcgctc | 540 |
| gtgacgaatt | cgacggtaca | cgtcatcatg | tacggttact | acttcctctg | cgccgttgga | 600 |
| tcgaggccca | agtggaagag | attggtgacg | gattgtcaga | ttgttcagtt | tgttttcagt | 660 |

```
ttcgggttat ccggttggat gctccgagag cacttattcg ggtcgggttg caccgggatt    720
tggggatggt gtttcaacgc tgcatttaat gcttctcttt tggctctctt ttccaacttc    780
cattcaaaga attatgtcaa gaagccaacg agagaggatg gcaaaaaaag cgattag       837
```

<210> SEQ ID NO 60
<211> LENGTH: 278
<212> TYPE: PRT
<213> ORGANISM: Arabidopsis thaliana

<400> SEQUENCE: 60

```
Met Ala Ser Ile Tyr Ser Ser Leu Thr Tyr Trp Leu Val Asn His Pro
1               5                   10                  15

Tyr Ile Ser Asn Phe Thr Trp Ile Glu Gly Glu Thr Leu Gly Ser Thr
            20                  25                  30

Val Phe Phe Val Ser Val Val Ser Val Tyr Leu Ser Ala Thr Phe
        35                  40                  45

Leu Leu Arg Ser Ala Ile Asp Ser Leu Pro Ser Leu Ser Pro Arg Ile
    50                  55                  60

Leu Lys Pro Ile Thr Ala Val His Ser Leu Ile Leu Cys Leu Leu Ser
65                  70                  75                  80

Leu Val Met Ala Val Gly Cys Thr Leu Ser Ile Thr Ser Ser His Ala
                85                  90                  95

Ser Ser Asp Pro Met Ala Arg Phe Leu His Ala Ile Cys Phe Pro Val
            100                 105                 110

Asp Val Lys Pro Asn Gly Pro Leu Phe Phe Trp Ala Gln Val Phe Tyr
        115                 120                 125

Leu Ser Lys Ile Leu Glu Phe Gly Asp Thr Ile Leu Ile Ile Leu Gly
    130                 135                 140

Lys Ser Ile Gln Arg Leu Ser Phe Leu His Val Tyr His Ala Thr
145                 150                 155                 160

Val Val Val Met Cys Tyr Leu Trp Leu Arg Thr Arg Gln Ser Met Phe
                165                 170                 175

Pro Ile Ala Leu Val Thr Asn Ser Thr Val His Val Ile Met Tyr Gly
            180                 185                 190

Tyr Tyr Phe Leu Cys Ala Val Gly Ser Arg Pro Lys Trp Lys Arg Leu
        195                 200                 205

Val Thr Asp Cys Gln Ile Val Gln Phe Val Ser Phe Gly Leu Ser
    210                 215                 220

Gly Trp Met Leu Arg Glu His Leu Phe Gly Ser Gly Cys Thr Gly Ile
225                 230                 235                 240

Trp Gly Trp Cys Phe Asn Ala Ala Phe Asn Ala Ser Leu Leu Ala Leu
                245                 250                 255

Phe Ser Asn Phe His Ser Lys Asn Tyr Val Lys Lys Pro Thr Arg Glu
            260                 265                 270

Asp Gly Lys Lys Ser Asp
        275
```

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61

```
gcggccgcca tgaagatata ctctagaacg                                           30

<210> SEQ ID NO 62
<211> LENGTH: 27
<212> TYPE: DNA
<213> ORGANISM: Artificial Sequence
<220> FEATURE:
<223> OTHER INFORMATION: Primer

<400> SEQUENCE: 62
gatatcttag gctgcctctg caaaccc                                              27

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
gcggccgcca tgggagtata ctcgagagcg                                           30

<210> SEQ ID NO 64
<211> LENGTH: 27
<212> TYPE: DNA
<213> ORGANISM: Artificial Sequence
<220> FEATURE:
<223> OTHER INFORMATION: Primer

<400> SEQUENCE: 64
cccgggtcac acggcttctg cgaagcc                                              27

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
gcggccgcca tgggaactag gttccaatca                                           30

<210> SEQ ID NO 66
<211> LENGTH: 27
<212> TYPE: DNA
<213> ORGANISM: Artificial Sequence
<220> FEATURE:
<223> OTHER INFORMATION: Primer

<400> SEQUENCE: 66
aggcctttaa gcagctttgg cgaatcc                                              27

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
gagcggccgc catggagaaa ggtttgacga t                                         31

<210> SEQ ID NO 68
<211> LENGTH: 31
<212> TYPE: DNA
<213> ORGANISM: Artificial Sequence
```

<220> FEATURE:
<223> OTHER INFORMATION: Primer

<400> SEQUENCE: 68
gagcggccgc cttaaggatg caagggctcc t          31

<210> SEQ ID NO 69
<211> LENGTH: 35
<212> TYPE: DNA
<213> ORGANISM: Artificial Sequence
<220> FEATURE:
<223> OTHER INFORMATION: Primer

<400> SEQUENCE: 69
gagcggccgc catgcattgg catggtgtag agcag       35

<210> SEQ ID NO 70
<211> LENGTH: 31
<212> TYPE: DNA
<213> ORGANISM: Artificial Sequence
<220> FEATURE:
<223> OTHER INFORMATION: Primer

<400> SEQUENCE: 70
gagcggccgc cttattcata gcaaggcggc a          31

<210> SEQ ID NO 71
<211> LENGTH: 32
<212> TYPE: DNA
<213> ORGANISM: Artificial Sequence
<220> FEATURE:
<223> OTHER INFORMATION: Primer

<400> SEQUENCE: 71
gagcggccgc catgtctgct tctgattcct ct         32

<210> SEQ ID NO 72
<211> LENGTH: 31
<212> TYPE: DNA
<213> ORGANISM: Artificial Sequence
<220> FEATURE:
<223> OTHER INFORMATION: Primer

<400> SEQUENCE: 72
gagcggccgc cttagtcgcg gaactcgtcc a          31

<210> SEQ ID NO 73
<211> LENGTH: 34
<212> TYPE: DNA
<213> ORGANISM: Artificial Sequence
<220> FEATURE:
<223> OTHER INFORMATION: Primer

<400> SEQUENCE: 73
gagcggccgc catggcgttc cctaaggtat actt        34

<210> SEQ ID NO 74
<211> LENGTH: 31
<212> TYPE: DNA
<213> ORGANISM: Artificial Sequence
<220> FEATURE:
<223> OTHER INFORMATION: Primer

<400> SEQUENCE: 74
gagcggccgc cctaagagag ctgaccacaa t          31

```
<210> SEQ ID NO 75
<211> LENGTH: 31
<212> TYPE: DNA
<213> ORGANISM: Artificial Sequence
<220> FEATURE:
<223> OTHER INFORMATION: Primer

<400> SEQUENCE: 75
gagcggccgc catgggtagt gcaaaatcag c                              31

<210> SEQ ID NO 76
<211> LENGTH: 31
<212> TYPE: DNA
<213> ORGANISM: Artificial Sequence
<220> FEATURE:
<223> OTHER INFORMATION: Primer

<400> SEQUENCE: 76
gagcggccgc cttaggcgat ggagctttta t                              31

<210> SEQ ID NO 77
<211> LENGTH: 31
<212> TYPE: DNA
<213> ORGANISM: Artificial Sequence
<220> FEATURE:
<223> OTHER INFORMATION: Primer

<400> SEQUENCE: 77
gagcggccgc catgactaat cccatgatca t                              31

<210> SEQ ID NO 78
<211> LENGTH: 31
<212> TYPE: DNA
<213> ORGANISM: Artificial Sequence
<220> FEATURE:
<223> OTHER INFORMATION: Primer

<400> SEQUENCE: 78
gagcggccgc cctagagacg gtggatcaac g                              31

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
gagcggccgc catggtttct tcttctttaa c                              31

<210> SEQ ID NO 80
<211> LENGTH: 31
<212> TYPE: DNA
<213> ORGANISM: Artificial Sequence
<220> FEATURE:
<223> OTHER INFORMATION: Primer

<400> SEQUENCE: 80
gagcggccgc cttaataatt ggtagcttta t                              31

<210> SEQ ID NO 81
<211> LENGTH: 31
<212> TYPE: DNA
<213> ORGANISM: Artificial Sequence
<220> FEATURE:
<223> OTHER INFORMATION: Primer
```

```
<400> SEQUENCE: 81
gagcggccgc catggccgga gttttcaaaa c                               31

<210> SEQ ID NO 82
<211> LENGTH: 31
<212> TYPE: DNA
<213> ORGANISM: Artificial Sequence
<220> FEATURE:
<223> OTHER INFORMATION: Primer

<400> SEQUENCE: 82
gagcggccgc ctcaaaagag agcaacaaca g                               31

<210> SEQ ID NO 83
<211> LENGTH: 31
<212> TYPE: DNA
<213> ORGANISM: Artificial Sequence
<220> FEATURE:
<223> OTHER INFORMATION: Primer

<400> SEQUENCE: 83
gagcggccgc catggcgtca aagcaactga g                               31

<210> SEQ ID NO 84
<211> LENGTH: 31
<212> TYPE: DNA
<213> ORGANISM: Artificial Sequence
<220> FEATURE:
<223> OTHER INFORMATION: Primer

<400> SEQUENCE: 84
gagcggccgc ctcacttgtt ggtgaacttt g                               31

<210> SEQ ID NO 85
<211> LENGTH: 31
<212> TYPE: DNA
<213> ORGANISM: Artificial Sequence
<220> FEATURE:
<223> OTHER INFORMATION: Primer

<400> SEQUENCE: 85
gcggccgcca tggcaacggg ggctgagaac c                               31

<210> SEQ ID NO 86
<211> LENGTH: 27
<212> TYPE: DNA
<213> ORGANISM: Artificial Sequence
<220> FEATURE:
<223> OTHER INFORMATION: Primer

<400> SEQUENCE: 86
aggcctttac cggcgaccac cagcagg                                    27

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
gcggccgcca tggcaaccat ggctaggtcg                                 30

<210> SEQ ID NO 88
```

<211> LENGTH: 28
<212> TYPE: DNA
<213> ORGANISM: Artificial Sequence
<220> FEATURE:
<223> OTHER INFORMATION: Primer

<400> SEQUENCE: 88
aggccttcag ttgtcgtgca atgctttg                                28

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
gcggccgcca tggcgcaacc cctcgtgaag                              30

<210> SEQ ID NO 90
<211> LENGTH: 27
<212> TYPE: DNA
<213> ORGANISM: Artificial Sequence
<220> FEATURE:
<223> OTHER INFORMATION: Primer

<400> SEQUENCE: 90
aggcctttag ccgctggcaa caatctc                                 27

<210> SEQ ID NO 91
<211> LENGTH: 31
<212> TYPE: DNA
<213> ORGANISM: Artificial Sequence
<220> FEATURE:
<223> OTHER INFORMATION: Primer

<400> SEQUENCE: 91
gcggccgcca tgccgattag ccggagagtt c                            31

<210> SEQ ID NO 92
<211> LENGTH: 26
<212> TYPE: DNA
<213> ORGANISM: Artificial Sequence
<220> FEATURE:
<223> OTHER INFORMATION: Primer

<400> SEQUENCE: 92
gatatctcat atggaatcat aaaccg                                  26

<210> SEQ ID NO 93
<211> LENGTH: 31
<212> TYPE: DNA
<213> ORGANISM: Artificial Sequence
<220> FEATURE:
<223> OTHER INFORMATION: Primer

<400> SEQUENCE: 93
gcggccgcca tgcccattaa tcagaaaatt c                            31

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94

```
aggccttcat ttgcgatcaa gaacc                                         25

<210> SEQ ID NO 95
<211> LENGTH: 37
<212> TYPE: DNA
<213> ORGANISM: Artificial Sequence
<220> FEATURE:
<223> OTHER INFORMATION: Primer

<400> SEQUENCE: 95
ctgcaggcgg ccgccatgga gtgtagttca gtgagtg                            37

<210> SEQ ID NO 96
<211> LENGTH: 28
<212> TYPE: DNA
<213> ORGANISM: Artificial Sequence
<220> FEATURE:
<223> OTHER INFORMATION: Primer

<400> SEQUENCE: 96
aggcctctag tattggacta acgataac                                      28

<210> SEQ ID NO 97
<211> LENGTH: 30
<212> TYPE: DNA
<213> ORGANISM: Artificial Sequence
<220> FEATURE:
<223> OTHER INFORMATION: Primer

<400> SEQUENCE: 97
gcggccgcat ggttgaaacc ttgtttgaag                                    30

<210> SEQ ID NO 98
<211> LENGTH: 26
<212> TYPE: DNA
<213> ORGANISM: Artificial Sequence
<220> FEATURE:
<223> OTHER INFORMATION: Primer

<400> SEQUENCE: 98
aggcctctag gccttatcca ccttcc                                        26

<210> SEQ ID NO 99
<211> LENGTH: 30
<212> TYPE: DNA
<213> ORGANISM: Artificial Sequence
<220> FEATURE:
<223> OTHER INFORMATION: Primer

<400> SEQUENCE: 99
gcggccgcat gggcaaaaaa gacatgccta                                    30

<210> SEQ ID NO 100
<211> LENGTH: 28
<212> TYPE: DNA
<213> ORGANISM: Artificial Sequence
<220> FEATURE:
<223> OTHER INFORMATION: Primer

<400> SEQUENCE: 100
aggccttcat attgtcgtgt aacgaggg                                      28

<210> SEQ ID NO 101
<211> LENGTH: 30
<212> TYPE: DNA
```

```
<213> ORGANISM: Artificial Sequence
<220> FEATURE:
<223> OTHER INFORMATION: Primer

<400> SEQUENCE: 101
gcggccgcat gatattatcg tttcgtggac                                               30

<210> SEQ ID NO 102
<211> LENGTH: 28
<212> TYPE: DNA
<213> ORGANISM: Artificial Sequence
<220> FEATURE:
<223> OTHER INFORMATION: Primer

<400> SEQUENCE: 102
aggcctctat acagatttgc catcgctc                                                 28

<210> SEQ ID NO 103
<211> LENGTH: 29
<212> TYPE: DNA
<213> ORGANISM: Artificial Sequence
<220> FEATURE:
<223> OTHER INFORMATION: Primer

<400> SEQUENCE: 103
gcggccgcat gaaccggatg atcgaagcg                                                29

<210> SEQ ID NO 104
<211> LENGTH: 27
<212> TYPE: DNA
<213> ORGANISM: Artificial Sequence
<220> FEATURE:
<223> OTHER INFORMATION: Primer

<400> SEQUENCE: 104
aggccttcat atttggtgca cctcggc                                                  27

<210> SEQ ID NO 105
<211> LENGTH: 28
<212> TYPE: DNA
<213> ORGANISM: Artificial Sequence
<220> FEATURE:
<223> OTHER INFORMATION: Primer

<400> SEQUENCE: 105
gcggccgcat gcagaccgtt tctcggag                                                 28

<210> SEQ ID NO 106
<211> LENGTH: 26
<212> TYPE: DNA
<213> ORGANISM: Artificial Sequence
<220> FEATURE:
<223> OTHER INFORMATION: Primer

<400> SEQUENCE: 106
aggccttcaa ggataagact ctggag                                                   26

<210> SEQ ID NO 107
<211> LENGTH: 29
<212> TYPE: DNA
<213> ORGANISM: Artificial Sequence
<220> FEATURE:
<223> OTHER INFORMATION: Primer

<400> SEQUENCE: 107
gcggccgcat ggcttcggtt actttctct                                                29
```

```
<210> SEQ ID NO 108
<211> LENGTH: 26
<212> TYPE: DNA
<213> ORGANISM: Artificial Sequence
<220> FEATURE:
<223> OTHER INFORMATION: Primer

<400> SEQUENCE: 108
aggccttcac ttccagttgt tggcaa                                    26

<210> SEQ ID NO 109
<211> LENGTH: 28
<212> TYPE: DNA
<213> ORGANISM: Artificial Sequence
<220> FEATURE:
<223> OTHER INFORMATION: Primer

<400> SEQUENCE: 109
gcggccgcat ggcaaaagaa aatggatt                                  28

<210> SEQ ID NO 110
<211> LENGTH: 26
<212> TYPE: DNA
<213> ORGANISM: Artificial Sequence
<220> FEATURE:
<223> OTHER INFORMATION: Primer

<400> SEQUENCE: 110
aggcctttag atagagaggt cagcga                                    26

<210> SEQ ID NO 111
<211> LENGTH: 28
<212> TYPE: DNA
<213> ORGANISM: Artificial Sequence
<220> FEATURE:
<223> OTHER INFORMATION: Primer

<400> SEQUENCE: 111
gcggccgcat ggcggcgaaa attcccgg                                  28

<210> SEQ ID NO 112
<211> LENGTH: 26
<212> TYPE: DNA
<213> ORGANISM: Artificial Sequence
<220> FEATURE:
<223> OTHER INFORMATION: Primer

<400> SEQUENCE: 112
aggccttcaa gacatgaaca gagcct                                    26

<210> SEQ ID NO 113
<211> LENGTH: 29
<212> TYPE: DNA
<213> ORGANISM: Artificial Sequence
<220> FEATURE:
<223> OTHER INFORMATION: Primer

<400> SEQUENCE: 113
gcggccgcat gggttacata ggagctcat                                 29

<210> SEQ ID NO 114
<211> LENGTH: 26
<212> TYPE: DNA
<213> ORGANISM: Artificial Sequence
<220> FEATURE:
```

-continued

<223> OTHER INFORMATION: Primer

<400> SEQUENCE: 114
aggccttcaa gcttctttac gcgtga                                    26

<210> SEQ ID NO 115
<211> LENGTH: 30
<212> TYPE: DNA
<213> ORGANISM: Artificial Sequence
<220> FEATURE:
<223> OTHER INFORMATION: Primer

<400> SEQUENCE: 115
gcggccgcat gtctccttct cactccatca                                30

<210> SEQ ID NO 116
<211> LENGTH: 26
<212> TYPE: DNA
<213> ORGANISM: Artificial Sequence
<220> FEATURE:
<223> OTHER INFORMATION: Primer

<400> SEQUENCE: 116
aggccttcat ttggtgtttg aaatat                                    26

<210> SEQ ID NO 117
<211> LENGTH: 32
<212> TYPE: DNA
<213> ORGANISM: Artificial Sequence
<220> FEATURE:
<223> OTHER INFORMATION: Primer

<400> SEQUENCE: 117
gcggccgcat ggcatctgtt tactccaccc ta                             32

<210> SEQ ID NO 118
<211> LENGTH: 26
<212> TYPE: DNA
<213> ORGANISM: Artificial Sequence
<220> FEATURE:
<223> OTHER INFORMATION: Primer

<400> SEQUENCE: 118
aggcctttaa tcgttttttct tggaaa                                   26

<210> SEQ ID NO 119
<211> LENGTH: 31
<212> TYPE: DNA
<213> ORGANISM: Artificial Sequence
<220> FEATURE:
<223> OTHER INFORMATION: Primer

<400> SEQUENCE: 119
gcggccgcat ggcatcaatt tactcctctt t                              31

<210> SEQ ID NO 120
<211> LENGTH: 26
<212> TYPE: DNA
<213> ORGANISM: Artificial Sequence
<220> FEATURE:
<223> OTHER INFORMATION: Primer

<400> SEQUENCE: 120
aggcctctaa tcgctttttt tgccat                                    26

-continued

```
<210> SEQ ID NO 121
<211> LENGTH: 1200
<212> TYPE: DNA
<213> ORGANISM: Helianthus annuus

<400> SEQUENCE: 121
atgcagaccg tttctcggag attagctcgt gaaaatttga gctctcgcac atcgatttac      60
tctctcaaat cgctttatcc tgtttccgat cgctgttacg gtgagtatga tcggcgttat     120
gcctctacgc ttaccaccaa aggtattgga catctggtcc gcaagggtac tggtggaaga     180
tcgtctgtta gtgggatagt tgctacagta ttcggagcta ctggtttcct tgggcgttac     240
ttggtgcaac agcttgctaa aacgggttca caagtgctag taccatttag aggttccgaa     300
gattcgcccc gtcatctcaa actgatgggc gatttgggc agattgttcc catgaaatat      360
aatcctagag atgaaaactc aattaaggca gtcatggcca aggcaaatgt tgtgattaat     420
ctcataggaa gggaatatga aaccagaaat tatagttttg aggaagtgaa ccatcatatg     480
gctgaacaac ttgcaaagat tccaaagaa catggtggaa tcatgagatt tatacaactg      540
tcgtgtttag gtcatctaa atcatctcca tctaggatgc ttcaagccaa ggctgctgca      600
gaagaatcca tcttacgtga attgcctgag gccacaatac tgcgacctgc agtgatggtt     660
ggtacagaag atcggatctt gaacccatgg gctcagttcg ctaaaaaata aactttctt      720 ccaatgatcg ggggtggttc tactaagatt cagcctgtgt atgttgctga tgtcgcctct     780
gcagttgttg cggcattaag tgatgacggt agtagcatgg aaaagtgta tgaacttggt      840 gggcctgatg tttatacact gcatcaattg gctgaactta tgtatgaaac gattcgagaa     900
tggcctcatt atgttaacgt tccttttccct attgctaagg cgatctcaac acctcgagaa    960
gtatttctta ataaagttcc cttcccgtta ccctcaccaa tcatcttcaa tttggatgtg    1020
attaatgctc tttcttcaga tactctcgtc tcaaaagatg ctctgacatt caatgatctt    1080
gagcttgtgc cacataaggt gaagggatat cctattgagt accttatcca gtatcgcaag    1140
ggtggaccca attcggctc tacagtcagt gaaagagtga ctccagagtc ttatccttga    1200

<210> SEQ ID NO 122
<211> LENGTH: 399
<212> TYPE: PRT
<213> ORGANISM: Helianthus annuus

<400> SEQUENCE: 122

Met Gln Thr Val Ser Arg Arg Leu Ala Arg Glu Asn Leu Ser Ser Arg
  1               5                  10                  15

Thr Ser Ile Tyr Ser Leu Lys Ser Leu Tyr Pro Val Ser Asp Arg Cys
             20                  25                  30

Tyr Gly Glu Tyr Asp Arg Arg Tyr Ala Ser Thr Leu Thr Thr Lys Gly
         35                  40                  45

Ile Gly His Leu Val Arg Lys Gly Thr Gly Gly Arg Ser Ser Val Ser
     50                  55                  60

Gly Ile Val Ala Thr Val Phe Gly Ala Thr Gly Phe Leu Gly Arg Tyr
 65                  70                  75                  80

Leu Val Gln Gln Leu Ala Lys Thr Gly Ser Gln Val Leu Val Pro Phe
                 85                  90                  95

Arg Gly Ser Glu Asp Ser Pro Arg His Leu Lys Leu Met Gly Asp Leu
            100                 105                 110

Gly Gln Ile Val Pro Met Lys Tyr Asn Pro Arg Asp Glu Asn Ser Ile
        115                 120                 125
```

```
Lys Ala Val Met Ala Lys Ala Asn Val Val Ile Asn Leu Ile Gly Arg
    130                 135                 140
Glu Tyr Glu Thr Arg Asn Tyr Ser Phe Glu Glu Val Asn His His Met
145                 150                 155                 160
Ala Glu Gln Leu Ala Lys Ile Ser Lys Glu His Gly Gly Ile Met Arg
                165                 170                 175
Phe Ile Gln Leu Ser Cys Leu Gly Ala Ser Lys Ser Ser Pro Ser Arg
            180                 185                 190
Met Leu Gln Ala Lys Ala Ala Glu Glu Ser Ile Leu Arg Glu Leu
        195                 200                 205
Pro Glu Ala Thr Ile Leu Arg Pro Ala Val Met Val Gly Thr Glu Asp
    210                 215                 220
Arg Ile Leu Asn Pro Trp Ala Gln Phe Ala Lys Lys Tyr Asn Phe Leu
225                 230                 235                 240
Pro Met Ile Gly Gly Gly Ser Thr Lys Ile Gln Pro Val Tyr Val Ala
                245                 250                 255
Asp Val Ala Ser Ala Val Ala Ala Leu Ser Asp Asp Gly Ser Ser
            260                 265                 270
Met Gly Lys Val Tyr Glu Leu Gly Gly Pro Asp Val Tyr Thr Leu His
        275                 280                 285
Gln Leu Ala Glu Leu Met Tyr Glu Thr Ile Arg Glu Trp Pro His Tyr
    290                 295                 300
Val Asn Val Pro Phe Pro Ile Ala Lys Ala Ile Ser Thr Pro Arg Glu
305                 310                 315                 320
Val Phe Leu Asn Lys Val Pro Phe Pro Leu Pro Ser Pro Ile Ile Phe
                325                 330                 335
Asn Leu Asp Val Ile Asn Ala Leu Ser Ser Asp Thr Leu Val Ser Lys
            340                 345                 350
Asp Ala Leu Thr Phe Asn Asp Leu Glu Leu Val Pro His Lys Val Lys
        355                 360                 365
Gly Tyr Pro Ile Glu Tyr Leu Ile Gln Tyr Arg Lys Gly Gly Pro Asn
    370                 375                 380
Tyr Gly Ser Thr Val Ser Glu Arg Val Thr Pro Glu Ser Tyr Pro
385                 390                 395

<210> SEQ ID NO 123
<211> LENGTH: 1653
<212> TYPE: DNA
<213> ORGANISM: Arabidopsis thaliana

<400> SEQUENCE: 123
atggagtgta gttcagtgag tgtactagga atattactgg tatttcctct ccttcataac    60
cttgtcacca tctccgggca gaatcttccg gcggtgggtt tgttcacttt cggagattcc   120
aacttcgacg ctggaaataa aaagttcctc acaagtgctc cacttcctca aaacttttgg   180
ccttacggta aatctcgaga tgaccctaag ggcaagtttt ctgatggcaa aattgtcccg   240
gactttattg caaaattcat ggggatacca cacgatttac cgccggcgct aaaacccggc   300
accgatgtgt cacgaggagc cagcttcgcc gtcgggtccg cttccattct tggatctcca   360
aaagattctt tggctctgaa tcaacaagtg aggaaattca atcagatgat atcaaattgg   420
aaagtggatt acattcagaa atcagtgttt atgattagca ttggtatgga agattactac   480
aactttacca aaaacaatcc taatgctgaa gtttctgctc aacaagcttt cgttacttct   540
gtcactaacc ggtttaagag tgatatcaac ttgttgtatt catctggagc tagtaaattc   600
```

```
                                                              -continued
gtcgtacact tgctagcgcc attaggttgt ttaccgatcg caagacaaga atttaaaacc       660
ggtaacaatt gttacgagaa actcgatgat ttggccaaac aacacaacgc taaaattgga       720
ccgattttga acgaaatggc ggaaactaaa ccggatttcc aattcaccgt tttcgatttc       780
tacaacgtta ttcttcgcag gacacaaaga aacatgaact accggttttc cgtgacgaat       840
atatcgtgtt gcggtgttgg gacgcattat gcatatggtt gtggtttacc taacgtgcac       900
tcgaagttat gcgaatatca aagatcctac ctttacttcg acgcacgtca taacacagag       960
aaagcacaag aagcgtttgc tcatcttatc tttggagctg acccaaatgt tatccaacct      1020
atgaatgttc gtgagctcat ggtgtatcct gttaatgagc ctatgcgtga gttttgggag      1080
gatccaatgg atgagaagtt atcgttagtc caatactaga ggagcttgtt gagcagaaac      1140
ttcagcatta ggattgtttt tggtaaagtt gtagtaatct tccataccaa tgctaatcat      1200
aaacactgat ttctgaatgt aatccacttt ccaatttgat atcatctgat tgaatttcct      1260
cacttgttga ttcagagcca aagaatcttt tggagatcca agaatggaag cggacccgac      1320
ggcgaagctg gctcctcgtg acacatcggt gccgggtttt agcgccggcg gtaaatcgtg      1380
tggtatcccc atgaattttg caataaagtc cgggacaatt ttgccatcag aaaacttgcc      1440
cttagggtca tctcgagatt taccgtaagg ccaaaagttt tgaggaagtg gagcacttgt      1500
gaggaacttt ttatttccag cgtcgaagtt ggaatctccg aaagtgaaca aacccaccgc      1560
cggaagattc tgcccggaga tggtgacaag gttatgaagg agaggaaata ccagtaatat      1620
tcctagtaca ctcactgaac tacactccat ggc                                   1653
```